(12) United States Patent
Nataro

(10) Patent No.: US 7,488,814 B2
(45) Date of Patent: *Feb. 10, 2009

(54) **POLYNUCLEOTIDES ENCODING NOVEL PROTEINS IN ENTEROAGGREGATIVE *ESCHERICHIA COLI* (EAEC) USEFUL FOR DIAGNOSIS AND THERAPY OF EAEC INFECTIONS**

(75) Inventor: James Nataro, Owings Mills, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 333 days.

This patent is subject to a terminal disclaimer.

(21) Appl. No.: 11/408,934

(22) Filed: Apr. 24, 2006

(65) Prior Publication Data

US 2006/0177466 A1 Aug. 10, 2006

Related U.S. Application Data

(60) Continuation of application No. 10/847,391, filed on May 18, 2004, now Pat. No. 7,087,741, which is a division of application No. 10/307,294, filed on Dec. 2, 2002, now Pat. No. 7,141,662.

(60) Provisional application No. 60/398,775, filed on Jul. 26, 2002, provisional application No. 60/334,425, filed on Nov. 30, 2001.

(51) Int. Cl.
*C07H 21/04* (2006.01)
*A61K 39/02* (2006.01)
*C12N 1/21* (2006.01)
*C12N 15/74* (2006.01)
*C07K 14/245* (2006.01)

(52) U.S. Cl. ............ 536/23.7; 435/69.1; 435/69.3; 435/252.33; 435/320.1; 435/488; 530/350; 424/190.01

(58) Field of Classification Search .......... 536/23.7; 435/69.1, 69.3, 252.33, 320.1, 488; 530/350; 424/190.1

See application file for complete search history.

(56) References Cited

U.S. PATENT DOCUMENTS 5,189,151 A 2/1993 Baundry et al.

6,436,055 B1 8/2002 Roe

OTHER PUBLICATIONS

EMBL-EBI printout for Accession No. Q6V4K6 (Jul. 5, 2004).
Schmidt et al, *J. of Clin. Microbiol.*, 33(3):701-705 (1995).
Lai et al, *Microbiology*, 145(Pt. 11):3295-3303 (1999).
GenEmbl Accession No. Z32523 (Oct. 31, 1994).
Nataro et al, *J. of Infectious Diseases*, 171(2):465-468 (1995).
Nataro et al, *J. of Infectious Diseases*, 152(3):560-565 (1985).
Nishi et al, *J. Biolog. Chem.*, 278(46):45680-45689 (2003).
Sheikh et al, *J. Clin. Invest.*, 110(9):1329-1337 (2000).
Nataro et al, *Infect. Immun.*, 61(3):1126-1131 (1993).
Greenspan, *Nature Biotechnology*, 7:936-937 (1999).
Bowie, *Science*, 257:1306-1310 (1990).
Mullins et al, *EMBO. J.*, 8:4065-4071 (1989).
Mullins, *Hypertension*, 22:630-633 (1993).
Hammer, *Cell*, 63:1099-1112 (1990).
Taurog, *J. Immunol..*, 141:4020-4023 (1988).
Mullins et al, *J. Clin. Invest.*, 97(7):1557-1560 (1996).
Houdebine, *J. Biotech.*, 34:269-286 (1994).
Kappell, *Current Opinions in Biotechnology*, 3:548-552 (1992).
Cameron, *Molec. Biol.*, 7:253-265 (1997).
Niemann, *Transg. Res.*, 7:73-75 (1997).
Burgess et al, *J. of Cell Bio.*, 111:2129-2137 (1990).
Lazar et al, *Molecular and CellularBiology*, 8:1247-1251 (1988).
Overbeek, "Factors Affecting Transgenic Animal Production", *Transgenic Animal Technology*, C.A. Pinkert ed., Academic Press, Inc., pp. 96-98 (1994).
Wall, *Theriogenology*, 45:57-68 (1996).
Bork, *Genome Res.*, 10:398-400 (2000).
Tzipori et al, *Infect. and Immunity*, 60(12):5302-5306 (1992).
Elias et al. Organization of Biogenesis Genes for Aggregative Adherence Fimbria II Defines a Virulence Gene Cluster in Enteroaggregative *Escherichia coli*. *J Bacteriol.* Mar. 1999; 181(6): 1779-1785.
Rich et al. Characterization of Enteroaggregative *Escherichia coli* isolates. *FEMS Microbiol Lett.* 1999; 173, 55-61.
Nataro and Kaper. Diarrheagenic *Escherichia coli*. *Clin Microbiol Rev.* Jan. 1998; 11(1): 142-201.

*Primary Examiner*—Robert A Zeman
(74) *Attorney, Agent, or Firm*—Merchant & Gould P.C.

(57) ABSTRACT

Novel proteins and their corresponding nucleotide sequences in enteroaggregative *Escherichia coli* (EAEC) are provided. In particular, Aap and the five gene cluster (aat) of the AA probe region of the pAA plasmid of EAEC 042 have been identified, sequenced, and further characterized. The use of these novel proteins and their corresponding nucleotide sequences for diagnosis, therapy, and prevention of EAEC infections is also provided.

17 Claims, 24 Drawing Sheets

Figure 1

**Nucleotide sequence of *aap* (SEQ ID NO:1)**

```
atgaaaaaaa ttaagtttgt tatcttttct ggcatcttgg gtatcagcct gaatgctttt    60
gcgggtggta gcggttggaa cgcagataat gtggacccgt cccaatgtat aaaacagtct   120
ggagtacagt atacttataa cagcggtgtc tcagtatgta tgcaaggcct taatgaaggg   180
aaagtaaggg gggtgtctgt ctctggggta ttttattata atgatggcac aacaagcaac   240
ttcaaagggg ttgttacccc ctccacacct gtaaatacga accaagacat taacaagaca   300
aataaggttg gagtccaaaa atatcgtgct ctaaccgaat gggttaaa              348
```

Figure 2

Amino acid sequence of Aap (SEQ ID NO:2)

```
Met Lys Lys Ile Lys Phe Val Ile Phe Ser Gly Ile Leu Gly Ile Ser
1               5                   10                  15

Leu Asn Ala Phe Ala Gly Gly Ser Gly Trp Asn Ala Asp Asn Val Asp
            20                  25                  30

Pro Ser Gln Cys Ile Lys Gln Ser Gly Val Gln Tyr Thr Tyr Asn Ser
        35                  40                  45

Gly Val Ser Val Cys Met Gln Gly Leu Asn Glu Gly Lys Val Arg Gly
    50              55                  60

Val Ser Val Ser Gly Val Phe Tyr Tyr Asn Asp Gly Thr Thr Ser Asn
65              70                  75                      80

Phe Lys Gly Val Val Thr Pro Ser Thr Pro Val Asn Thr Asn Gln Asp
            85                  90                  95

Ile Asn Lys Thr Asn Lys Val Gly Val Gln Lys Tyr Arg Ala Leu Thr
        100                 105                 110

Glu Trp Val Lys
        115
```

Figure 9

Nucleotide sequence of pAA of EAEC 042 (SEQ ID NO:3)

```
gagacgtttg gaggtgtatg ggagccgcgt tatccgcagg agcttcataa ggtgattcat    60
acgaccatac cattgaatcg ctgaacagtg tgatccgtca ctcaatcaag aaacacaggg   120
tgttaccgat agatgagtta gtaaaaagcg gtgtcatcca ggtagcgtta cagaaatggg   180
ccatacccct gaagggatgt catcatggcg atgagtcgct ttcttatcaa tgacatccat   240
agtgtcatta taataacgac atttatgcat gccattgaca ttgtcagata ctatatttat   300
gaccaagaac tccatgcagg tccattgcta ttgatatcct cctgagcctc ccgtacaata   360
tcttttatta ggcttaaatc catatttgag gctattttga ttatattatc aaaatcagca   420
tctattacac atgtaactat atcaatcatt atacacctcc ttttctaaa cttttacatg    480
ctaaaacaaa ataaatcaaa aaatagatat tattatagca atagttgatt gctgttctaa   540
ctgaacgcca cgttcaacaa cctgtttgac agcttcaact ttaaactcct caggataaag   600
cttaccatgg gaatatctac ggcagcaggc cagtaatgga ttaagtgata acaggtgtct   660
ggaaatatag gggcaaatcc accgaccccg tactgctcac gcagcttatc caactgtggt   720
atcatttttt ccagaggcgg tcgaacctcg ccttcgcaaa ataagcggaa gcctggcgaa   780
ggatatcgtt actgcggcgc agttcacgat tttcacgctc cagctctttc agacgctgac   840
gttcagcagt ggtgagcccg ccwtcaccgc ccccggtatc ccgctcatgc tggcgaaccc   900
agacacgcag agtctccggt gtacagccaa tctttggggc aatggaacaa attaccgccc   960
attgtgagtc atattcgccc tgactttcca gaaccatacg aatcgccctc tgacggactt  1020
cggggggaaaa cgagtatttt tagtcatcct gtttacctct ttctctggaa gtttagtctc  1080
caggatttcc gggatggttc agtttacgta tgttttggct ggttgatact gttttttgtca 1140
tgtgagtcac ctctgactga gagtctactc atttagccgc gtgtccacta ttgctgggta  1200
agatcaaatc attaatatct ctgcataacg tgcaggagat gctccatagc attaactaca  1260
tatatttata ctaagtttag tcacacagat ttcgattatt atcataaact tatagttata  1320
tatcccttag ttattaatag ttgggtacat tatatagtgt ttccaataac tgtacatgtc  1380
tactcctgta agtgtggctg aggattcttg ggttatcatt caacatgaca actttgcact  1440
attatctaaa tgaggcgctc cttaatatca tagaaaatag aaggcagaat tttgcatttc  1500
ttgttttttt atctcttagc tttataggga taattattac tgactctttg atatacagtg  1560
tttccttaaa agccgaagaa gaactaaaag ttcatagtga caaagtaata tttgtcaaat  1620
tatatcgacc taaaacggta ggatatataa cggaaaaatt cattacggtt agtaaagttc  1680
tttctttctc gaagagcgca ttcctctatg tcagcgatac acctttttcc ggtgaactat  1740
tttcggtgaa cggaattgac aagctgggat taaatacgga atattcgggg gatttaaatg  1800
ataagtacaa tggcaatgtt gctattgtta atgaatctag tccgttttttc agtaagaaac  1860
aaatatttat taatggtgtt ccgtttaaaa ttattggtgt ccgattaaac tcaaaaacgg  1920
attttcttga cagccttgga ttgaaagcaa gccaatcaga tgaacacatt tttattccac  1980
tggaaactat gtttaaagtg aaactcgata acagagtcaa tgctgttaaa atctttcttg  2040
ataacatagt aacaaagaga gatataaaca acgtaaagag agttttatat gacaatgata  2100
taagaaaatt cgatattgtc acatctttaa acgccaagga agctgtggac agagtgttag  2160
agaggttttc attactcact aactctgttt acgtgatatt aactctgtct gcgtccgtga  2220
catgttttat tttatcgaaa cgcagttttt attcgagacg ggtagagtta tcattaaaaa  2280
taatccatgg tacagaaaag aaagagatta cagttctaat tatcattgag tcttaataa   2340
tgctgagcgt atgtcttttt atttcagtca tctatgcagg agtaataatg catattatta  2400
agtatttttt agatgtaaca ataagtatta ggacaacaat gattacaata tcacttgcca  2460
atgtcctatt ggtatttata tctgcaaata tcatttcgg caggctattt ttcagtataa   2520
accctgttaa tgcaataaaa ggaaagatcg agtgagacac atattatact catttcttgc  2580
aataaatgct tatctgtttt cgacacagac tctggcaaaa gactgtatca ttgataattt  2640
ctttcagaaa agcatccagt ttaattctta ttctcttgat atcgaagagt tggatattaa  2700
taaacataac aatataaaaa cgatgttacc agatataaat ataggggttag ggcagtatat 2760
aaacaacaat cagtggttct catctattac agacagcaat ttttatttat cattatccta  2820
taatcttcta tcggcttatg aagcaaaaat gcagaatgat aaattggata ttgctaatta  2880
tttaaaatat attgaaatgc ttagtgagag aaacaactat ataattaatt tgttctcgga  2940
```

Figure 9 (cont.)

```
aatcattaac tataagataa aaaaatctca cctgatgttg atgctcgaga gatatagaaa    3000
gcttaataaa gaatacgaaa ttgcaaagcg taaaatgtca attggattaa tatctgttct    3060
tgatgtagag atgagatata atatattaca aaaaatcagg tttgatattg atgtacttga    3120
ggaggaggaa agtttactgt cagataaaat ctcgagagaa tatcatgttc cagagagtgc    3180
aatcccagac attacatatc ataattaaa agagtgtaaa acagcggatt tctatacatt    3240
attagctgaa aacaaaaaac tcaagattaa ggctgctgat atagataatg atataagaaa    3300
actatcggag atcccatctt tttatttatc atttggatta acacctaaac agggaggtgc    3360
attgggtaat atgagtctca gaaaaatgga ttatagtgct agtctgggta tcagttttcc    3420
tttgatggga ttatttagtt cttcagaaaa tcaaaaagaa aagattattt ctatatctcg    3480
aaccagaaat gaattattga aagaaaatat aaaactagat ctgttggaaa aagagattcg    3540
ccagaaaatt gataaattag agaaaaatct tgcgatgatg aaaaatgaac tagctctgaa    3600
aaaaaggaaa attgagtata taattatcg cgtaaagaat ggacaagacg acgttatcac    3660
ttatttgtct agtgtagaga atttacatga aacagaaaat gaatttcaga aaattggata    3720
tgagattgaa tattatagtt tatatcatta ttttcttctg cagcacattt ccaatacagg    3780
ggaaatgtga taactactat ggtgttctac atggaaataa aaacgtaaaa tataagagtc    3840
cttttgcagg ggttgtaata cttgaggaca tgattgaagg taatgtggtc actgtggaaa    3900
ggaagctatt ttctgtcctg aatcatgagt atactgcaaa gaaagatatt gtggccatga    3960
aaagaaatat ggaagagaaa aaactatcta gattaaaagg agcaaagata catttaacct    4020
ctatgttctc aaaagggtta atttcaagag aaagcttgca tgatatagat gagaaaatca    4080
gcaatactga attgactatt atgggactgg acatagagtc aaagaatctg gaacaactat    4140
taaagttgtc atcaccattt ttgcatactc ctttcattat tcgaaatatc ttcgtaacaa    4200
atgagcagta tgtaaatgca ggcgatgata taatgtctgt agaacttctg gataattttt    4260
atatagatgt taaattcgat ccggtcagta taacaggaaa tataagagac aagagaataa    4320
ggtatcgttc tttggttaat tctctaatgg ggtctgcaac agtagtcaaa aatatccgtg    4380
ccagtggaga atcaactcaa ggtgaagata catcaggtct gcgctctatt acgctgttaa    4440
ttgatgggga ccggaatgaa ttgtcgaatc tattagatac tgcgtttgag attataatag    4500
atgattagag taaaaataca taaaaaacct atagaaaaca gaactatcct gaataatagc    4560
actattgaga taaagagggg atcgttcaat attattactg gcccgtctgg agttggaaag    4620
acttcactgc ttaacattat tggtctatta gataatgcct ttgttggaga gtatgaactt    4680
ttcggtaaaa aagtggaaat aaaagataat agcatcacta catatatcag aagaaaatat    4740
tttggattca tctttcagga ttctctgatt aatgtaaagc aaaatgtctt aagaaatata    4800
ctatgttctg tagattctca aaacataata gccgcaaggg aaagaattaa tgaagtcttg    4860
gtgtctgttg gattgtcaaa tattaataat aatgtatcat ttctctccgg gggagaaaaa    4920
caaagactag cacttgctag ggcattgata aaaaaaccca gtatacttt agcagatgaa    4980
cctactgcta gtctagatat aaagaataaa aaattagtga tgaatatact atctgaatac    5040
aataatcaag gaggaacagt cgttatggta actcatgatc ttgaactaat cgatgagaat    5100
atgactttaa tccaactatt aaatacatag gcttacagtt tatgaaattc gctattgtct    5160
tattgtattt ttttgcctat tatcttgcag caagaaaaag acgagtgagt ctttttttta    5220
ctattctttt atactctatc attttctctg ggatgtattt ttctagtggt tttttagaat    5280
attatggcag ttctaattta tacctttcat ttggattact ctgctataat atgataaccc    5340
ttgtcatata tggtttcctg agttcttatg ggttacttgg agcatgtcta catgcacttt    5400
cattaacctc attatccgcc ttcgggatgt ttataccatt aaatccattg attgttttat    5460
attatgattt tcctagcatc ttaccaagaa cagatattcc tgttttaaat ttattaatat    5520
taaatcttat tcctgcagtt acatttagtc taaaaatatc atttttttctc cgttctctta    5580
tattattatt gttatttccg ctaatatgga aacgccggt taatataact catcccctc    5640
tgaacattgt gattgtacag gttggccttt attttaaaaa agtaggtgtc agaggtaatt    5700
tttatacgga tctcaatgag ttcgtcagaa ataagaaggt tgatctaatt attctctcag    5760
aaaatgtttt tttcggttac aagaatgatt atataaagga aagaactaaa catctcttaa    5820
agcaattaaa agataatcga ctccactaca aatatgggat attaatgaat ctttatggat    5880
atcaagacat taataacgta gtgtctgctt tctggcataa agaagaattt cctctccacc    5940
aaaaagcaa attgatacct tttttgaga agaaaagttt ttataactca ccagaaccat    6000
cgacatcacc ttttctatat tataaaaaga aatataatga gcaggacatc ctggatttca    6060
acaacattaa aatgagtatt catatatgtt atgagggatt attccctgag ggtgaatctc    6120
```

Figure 9 (cont.)

```
gaagaaaaga tatctccatt gttcaatccg attattcatg gttgagtgac aatcacaaat   6180
atgacaacac ccttattaat ggaagtatat tatcgaaatt ctctgtttcg ccgaacactc   6240
ctcttattaa tattcaaaat tatggtggga cagtttttat agacaataat tggaaaattg   6300
atatggactt atttaatagg tcaaaaacgg aacctttttt atttacacag atatgagtaa   6360
tgcactaact ttcagttgaa aatagaagtg ctattatatt aactaatgta tagggaaatt   6420
tttagagata attaaagtaa atattggcgt tgaacaataa cgctaatatc gaggtgaata   6480
tgatttgctg actggcaata taacgaaaga ttaaaactct ctgaaaagag agtttatcat   6540
tagtatggcc acatagaagt tatgtcatag caatataaaa tagcttttat tagcttttaa   6600
aataaaatcc tgatgaatat aagtaagcgg ctcgtcagaa ccgtattgat atttactgag   6660
agctcagatc aactttccaa ggcaacagat cgcgtacccg gtttgtcggc cagtcctgga   6720
tatgctcaat gacgtaacgc agtcattttt ctggctccac attgttcaga cggcatgtgc   6780
cgatcagcga gtacaacacc gccgcatgtt cgccaccgct gtcggaaccc gcaacagcc    6840
agttttccg  gcctacagct actccccgta aggcgttctc tgtaatgttg ttgtcgattt    6900
ccacccagcc atcgttcgca tagtacgtca gtgccggcca ctggttaagt gcgtacgcga   6960
acgccttcgc caactctgag tgtcgtgaca gggtcttcat                         7000
```

Figure 10

Amino acid sequence of AatP (SEQ ID NO:4)

```
Met Thr Thr Leu His Tyr Tyr Leu Asn Glu Ala Leu Leu Asn Ile Ile
1               5                   10                  15

Glu Asn Arg Arg Gln Asn Phe Ala Phe Leu Val Phe Leu Ser Leu Ser
            20              25                  30

Phe Ile Gly Ile Ile Ile Thr Asp Ser Leu Ile Tyr Ser Val Ser Leu
            35              40                  45

Lys Ala Glu Glu Glu Leu Lys Val His Ser Asp Lys Val Ile Phe Val
        50              55                  60

Lys Leu Tyr Arg Pro Lys Thr Val Gly Tyr Ile Thr Glu Lys Phe Ile
65              70                  75                      80

Thr Val Ser Lys Val Leu Ser Phe Ser Lys Ser Ala Phe Leu Tyr Val
                85                  90                  95

Ser Asp Thr Pro Phe Ser Gly Glu Leu Phe Ser Val Asn Gly Ile Asp
            100                 105                 110

Lys Leu Gly Leu Asn Thr Glu Tyr Ser Gly Asp Leu Asn Asp Lys Tyr
            115                 120                 125

Asn Gly Asn Val Ala Ile Val Asn Glu Ser Ser Pro Phe Phe Ser Lys
            130                 135                 140

Lys Gln Ile Phe Ile Asn Gly Val Pro Phe Lys Ile Ile Gly Val Arg
145                 150                 155                 160

Leu Asn Ser Lys Thr Asp Phe Leu Asp Ser Leu Gly Leu Lys Ala Ser
                165                 170                 175

Gln Ser Asp Glu His Ile Phe Ile Pro Leu Glu Thr Met Phe Lys Val
            180                 185                 190

Lys Leu Asp Asn Arg Val Asn Ala Val Lys Ile Phe Leu Asp Asn Ile
            195                 200                 205

Val Thr Lys Arg Asp Ile Asn Asn Val Lys Arg Val Leu Tyr Asp Asn
            210                 215                 220

Asp Ile Arg Lys Phe Asp Ile Val Thr Ser Leu Asn Ala Lys Glu Ala
225                 230                 235                 240

Val Asp Arg Val Leu Glu Arg Phe Ser Leu Leu Thr Asn Ser Val Tyr
                245                 250                 255

Val Ile Leu Thr Leu Ser Ala Ser Val Thr Cys Phe Ile Leu Ser Lys
                260                 265                 270
```

Figure 10 (cont.)

```
Arg Ser Phe Tyr Ser Arg Arg Val Glu Leu Ser Leu Lys Ile Ile His
        275             280                 285

Gly Thr Glu Lys Lys Glu Ile Thr Val Leu Ile Ile Ile Glu Ser Leu
    290             295                 300

Ile Met Leu Ser Val Cys Leu Phe Ile Ser Val Ile Tyr Ala Gly Val
305             310             315                         320

Ile Met His Ile Ile Lys Tyr Phe Leu Asp Val Thr Ile Ser Ile Arg
            325             330                     335

Thr Thr Met Ile Thr Ile Ser Leu Ala Asn Val Leu Leu Val Phe Ile
        340             345                 350

Ser Ala Asn Ile Ile Phe Gly Arg Leu Phe Phe Ser Ile Asn Pro Val
        355             360                 365

Asn Ala Ile Lys Gly Lys Ile Glu
        370             375
```

Figure 11

Amino acid sequence of AatA (SEQ ID NO:5)

```
Val Arg His Ile Leu Tyr Ser Phe Leu Ala Ile Asn Ala Tyr Leu Phe
1            5                   10                  15

Ser Thr Gln Thr Leu Ala Lys Asp Cys Ile Ile Asp Asn Phe Phe Gln
            20                  25                  30

Lys Ser Ile Gln Phe Asn Ser Tyr Ser Leu Asp Ile Glu Glu Leu Asp
            35                  40                  45

Ile Asn Lys His Asn Asn Ile Lys Thr Met Leu Pro Asp Ile Asn Ile
50                      55                  60

Gly Leu Gly Gln Tyr Ile Asn Asn Gln Trp Phe Ser Ser Ile Thr
65                  70                  75                  80

Asp Ser Asn Phe Tyr Leu Ser Leu Ser Tyr Asn Leu Leu Ser Ala Tyr
                85                  90                  95

Glu Ala Lys Met Gln Asn Asp Lys Leu Asp Ile Ala Asn Tyr Leu Lys
            100                 105                 110

Tyr Ile Glu Met Leu Ser Glu Arg Asn Asn Tyr Ile Ile Asn Leu Phe
            115                 120                 125

Ser Glu Ile Ile Asn Tyr Lys Ile Lys Lys Ser His Leu Met Leu Met
        130                 135                 140

Leu Glu Arg Tyr Arg Lys Leu Asn Lys Glu Tyr Glu Ile Ala Lys Arg
145                 150                 155                 160

Lys Met Ser Ile Gly Leu Ile Ser Val Leu Asp Val Glu Met Arg Tyr
                165                 170                 175

Asn Ile Leu Gln Lys Ile Arg Phe Asp Ile Asp Val Leu Glu Glu Glu
            180                 185                 190

Glu Ser Leu Leu Ser Asp Lys Ile Ser Arg Glu Tyr His Val Pro Glu
            195                 200                 205

Ser Ala Ile Pro Asp Ile Thr Tyr His Lys Leu Lys Glu Cys Lys Thr
    210                 215                 220

Ala Asp Phe Tyr Thr Leu Leu Ala Glu Asn Lys Lys Leu Lys Ile Lys
225                 230                 235                 240

Ala Ala Asp Ile Asp Asn Asp Ile Arg Lys Leu Ser Glu Ile Pro Ser
            245                 250                 255

Phe Tyr Leu Ser Phe Gly Leu Thr Pro Lys Gln Gly Gly Ala Leu Gly
            260                 265                 270
```

Figure 11 (cont.)

```
Asn Met Ser Leu Arg Lys Met Asp Tyr Ser Ala Ser Leu Gly Ile Ser
        275             280                 285

Phe Pro Leu Met Gly Leu Phe Ser Ser Ser Glu Asn Gln Lys Glu Lys
    290             295                 300

Ile Ile Ser Ile Ser Arg Thr Arg Asn Glu Leu Leu Lys Glu Asn Ile
305                 310                 315                 320

Lys Leu Asp Leu Leu Glu Lys Glu Ile Arg Gln Lys Ile Asp Lys Leu
                325                 330                 335

Glu Lys Asn Leu Ala Met Met Lys Asn Glu Leu Ala Leu Lys Lys Arg
            340             345                 350

Lys Ile Glu Tyr Ile Asn Tyr Arg Val Lys Asn Gly Gln Asp Asp Val
        355                 360                 365

Ile Thr Tyr Leu Ser Ser Val Glu Asn Leu His Glu Thr Glu Asn Glu
    370             375                 380

Phe Gln Lys Ile Gly Tyr Glu Ile Glu Tyr Tyr Ser Leu Tyr His Tyr
385                 390                 395                 400

Phe Leu Leu Gln His Ile Ser Asn Thr Gly Glu Met
                405             410
```

Figure 12

Amino acid sequence of AatB (SEQ ID NO:6)

```
Met Lys Gln Lys Met Asn Phe Arg Lys Leu Asp Met Arg Leu Asn Ile
1               5                   10                  15

Ile Val Tyr Ile Ile Ile Phe Phe Cys Ser Thr Phe Pro Ile Gln Gly
            20                  25                  30

Lys Cys Asp Asn Tyr Tyr Gly Val Leu His Gly Asn Lys Asn Val Lys
        35                  40                  45

Tyr Lys Ser Pro Phe Ala Gly Val Val Ile Leu Glu Asp Met Ile Glu
    50                  55                  60

Gly Asn Val Val Thr Val Glu Arg Lys Leu Phe Ser Val Leu Asn His
65                  70                  75                  80

Glu Tyr Thr Ala Lys Lys Asp Ile Val Ala Met Lys Arg Asn Met Glu
            85                  90                  95

Glu Lys Lys Leu Ser Arg Leu Lys Gly Ala Lys Ile His Leu Thr Ser
            100                 105                 110

Met Phe Ser Lys Gly Leu Ile Ser Arg Glu Ser Leu His Asp Ile Asp
        115                 120                 125

Glu Lys Ile Ser Asn Thr Glu Leu Thr Ile Met Gly Leu Asp Ile Glu
    130                 135                 140

Ser Lys Asn Leu Glu Gln Leu Leu Lys Leu Ser Ser Pro Phe Leu His
145                 150                 155                 160

Thr Pro Phe Ile Ile Arg Asn Ile Phe Val Thr Asn Glu Gln Tyr Val
                165                 170                 175

Asn Ala Gly Asp Asp Ile Met Ser Val Glu Leu Leu Asp Asn Phe Tyr
            180                 185                 190

Ile Asp Val Lys Phe Asp Pro Val Ser Ile Thr Gly Asn Ile Arg Asp
        195                 200                 205

Lys Arg Ile Arg Tyr Arg Ser Leu Val Asn Ser Leu Met Gly Ser Ala
    210                 215                 220

Thr Val Val Lys Asn Ile Arg Ala Ser Gly Glu Ser Thr Gln Gly Glu
225                 230                 235                 240

Asp Thr Ser Gly Leu Arg Ser Ile Thr Leu Leu Ile Asp Gly Asp Arg
                245                 250                 255

Asn Glu Leu Ser Asn Leu Leu Asp Thr Ala Phe Glu Ile Ile Ile Asp
            260                 265                 270

Asp
```

Figure 13

Amino acid sequence of AatC (SEQ ID NO:7)

```
Met Ile Arg Val Lys Ile His Lys Lys Pro Ile Glu Asn Arg Thr Ile
1           5               10                  15

Leu Asn Asn Ser Thr Ile Glu Ile Lys Glu Gly Ser Phe Asn Ile Ile
            20              25                  30

Thr Gly Pro Ser Gly Val Gly Lys Thr Ser Leu Leu Asn Ile Ile Gly
            35              40                  45

Leu Leu Asp Asn Ala Phe Val Gly Glu Tyr Glu Leu Phe Gly Lys Lys
        50              55              60

Val Glu Ile Lys Asp Asn Ser Ile Thr Thr Tyr Ile Arg Arg Lys Tyr
65              70              75                      80

Phe Gly Phe Ile Phe Gln Asp Ser Leu Ile Asn Val Lys Gln Asn Val
                85              90                  95

Leu Arg Asn Ile Leu Cys Ser Val Asp Ser Gln Asn Ile Ile Ala Ala
            100             105                 110

Arg Glu Arg Ile Asn Glu Val Leu Val Ser Val Gly Leu Ser Asn Ile
        115             120             125

Asn Asn Asn Val Ser Phe Leu Ser Gly Gly Glu Lys Gln Arg Leu Ala
    130             135             140

Leu Ala Arg Ala Leu Ile Lys Lys Pro Ser Ile Leu Leu Ala Asp Glu
145             150             155                 160

Pro Thr Ala Ser Leu Asp Ile Lys Asn Lys Lys Leu Val Met Asn Ile
            165             170                 175

Leu Ser Glu Tyr Asn Asn Gln Gly Gly Thr Val Val Met Val Thr His
            180             185                 190

Asp Leu Glu Leu Ile Asp Glu Asn Met Thr Leu Ile Gln Leu Leu Asn
        195             200             205

Thr
```

Figure 14

Amino acid sequence of AatD (SEQ ID NO:8)

```
Met Lys Phe Ala Ile Val Leu Leu Tyr Phe Phe Ala Tyr Tyr Leu Ala
1               5                   10                  15

Ala Arg Lys Arg Arg Val Ser Leu Phe Phe Thr Ile Leu Leu Tyr Ser
            20                  25                  30

Ile Ile Phe Ser Gly Met Tyr Phe Ser Ser Gly Phe Leu Glu Tyr Tyr
        35                  40                  45

Gly Ser Ser Asn Leu Tyr Leu Ser Phe Gly Leu Leu Cys Tyr Asn Met
    50                  55                  60

Ile Thr Leu Val Ile Tyr Gly Phe Leu Ser Ser Tyr Gly Leu Leu Gly
65                  70                  75                  80

Ala Cys Leu His Ala Leu Ser Leu Thr Ser Leu Ser Ala Phe Gly Met
                85                  90                  95

Phe Ile Pro Leu Asn Pro Leu Ile Val Leu Tyr Tyr Asp Phe Pro Ser
            100                 105                 110

Ile Leu Pro Arg Thr Asp Ile Pro Val Leu Asn Leu Leu Ile Leu Asn
            115                 120                 125

Leu Ile Pro Ala Val Thr Phe Ser Leu Lys Ile Ser Phe Phe Leu Arg
        130                 135                 140

Ser Leu Ile Leu Leu Leu Phe Pro Leu Ile Trp Lys Thr Pro Val
145                 150                 155                 160

Asn Ile Thr His Pro Pro Leu Asn Ile Val Ile Val Gln Val Gly Leu
                165                 170                 175

Tyr Phe Lys Lys Val Gly Val Arg Gly Asn Phe Tyr Thr Asp Leu Asn
            180                 185                 190

Glu Phe Val Arg Asn Lys Lys Val Asp Leu Ile Ile Leu Ser Glu Asn
        195                 200                 205

Val Phe Phe Gly Tyr Lys Asn Asp Tyr Ile Lys Glu Arg Thr Lys His
    210                 215                 220

Leu Leu Lys Gln Leu Lys Asp Asn Arg Leu His Tyr Lys Tyr Gly Ile
225                 230                 235                 240

Leu Met Asn Leu Tyr Gly Tyr Gln Asp Ile Asn Asn Val Val Ser Ala
            245                 250                 255

Phe Trp His Lys Glu Glu Phe Leu Leu His Gln Lys Ser Lys Leu Ile
        260                 265                 270
```

Figure 14 (cont.)

```
Pro Phe Phe Glu Lys Lys Ser Phe Tyr Asn Ser Pro Glu Pro Ser Thr
        275                 280                 285

Ser Pro Phe Leu Tyr Tyr Lys Lys Tyr Asn Glu Gln Asp Ile Leu
290                 295                 300

Asp Phe Asn Asn Ile Lys Met Ser Ile His Ile Cys Tyr Glu Gly Leu
305                 310                 315                 320

Phe Pro Glu Gly Glu Ser Arg Arg Lys Asp Ile Ser Ile Val Gln Ser
                325                 330                 335

Asp Tyr Ser Trp Leu Ser Asp Asn His Lys Tyr Asp Asn Thr Leu Ile
            340                 345                 350

Asn Gly Ser Ile Leu Ser Lys Phe Ser Val Ser Pro Asn Thr Pro Leu
        355                 360                 365

Ile Asn Ile Gln Asn Tyr Gly Gly Thr Val Phe Ile Asp Asn Asn Trp
    370                 375                 380

Lys Ile Asp Met Asp Leu Phe Asn Arg Ser Lys Thr Glu Pro Phe Leu
385                 390                 395                 400

Phe Thr Gln Ile
```

Figure 15

**Nucleotide sequence of *aatP* (SEQ ID NO:9)**

```
atgacaactt tgcactatta tctaaatgag gcgctcctta atatcataga aaatagaagg      60
cagaattttg catttcttgt tttttatct cttagcttta tagggataat tattactgac     120
tctttgatat acagtgtttc cttaaaagcc gaagaagaac taaaagttca tagtgacaaa     180
gtaatatttg tcaaattata tcgacctaaa acggtaggat atataacgga aaaattcatt     240
acggttagta aagttctttc tttctcgaag agcgcattcc tctatgtcag cgatacacct     300
ttttccggtg aactattttc ggtgaacgga attgacaagc tgggattaaa tacggaatat     360
tcggggggatt taaatgataa gtacaatggc aatgttgcta ttgttaatga atctagtccg     420
ttttcagta agaaacaaat atttattaat ggtgttccgt ttaaaattat tggtgtccga     480
ttaaactcaa aaacggattt tcttgacagc cttggattga agcaagcca atcagatgaa     540
cacatttta ttccactgga aactatgttt aaagtgaaac tcgataacag agtcaatgct     600
gttaaaatct ttcttgataa catagtaaca aagagagata taaacaacgt aaagagagtt     660
ttatatgaca atgatataag aaaattcgat attgtcacat ctttaaacgc caaggaagct     720
gtggacagag tgttagagag gttttcatta ctcactaact ctgtttacgt gatattaact     780
ctgtctgcgt ccgtgacatg tttatttta tcgaaacgca gtttttattc gagacgggta     840
gagttatcat taaaaataat ccatggtaca gaaaagaaag agattacagt tctaattatc     900
attgagtctt taataatgct gagcgtatgt cttttattt cagtcatcta tgcaggagta     960
ataatgcata ttattaagta tttttagat gtaacaataa gtattaggac aacaatgatt    1020
acaatatcac ttgccaatgt cctattggta tttatatctg caaatatcat tttcggcagg    1080
ctattttca gtataaaccc tgttaatgca ataaaggaa agatcgagtg a              1131
```

Figure 16

**Nucleotide sequence of *aatA* (SEQ ID NO:10)**

```
gtgagacaca tattatactc atttcttgca ataaatgctt atctgttttc gacacagact    60
ctggcaaaag actgtatcat tgataatttc tttcagaaaa gcatccagtt taattcttat   120
tctcttgata tcgaagagtt ggatattaat aaacataaca atataaaaac gatgttacca   180
gatataaata tagggttagg gcagtatata aacaacaatc agtggttctc atctattaca   240
gacagcaatt tttatttatc attatcctat aatcttctat cggcttatga agcaaaaatg   300
cagaatgata aattggatat tgctaattat ttaaaatata ttgaaatgct tagtgagaga   360
aacaactata taattaattt gttctcggaa atcattaact ataagataaa aaaatctcac   420
ctgatgttga tgctcgagag atatagaaag cttaataaag aatacgaaat tgcaaagcgt   480
aaaatgtcaa ttggattaat atctgttctt gatgtagaga tgagatataa tatattacaa   540
aaaatcaggt ttgatattga tgtacttgag gaggaggaaa gtttactgtc agataaaatc   600
tcgagagaat atcatgttcc agagagtgca atcccagaca ttacatatca taaattaaaa   660
gagtgtaaaa cagcggattt ctatacatta ttagctgaaa acaaaaaact caagattaag   720
gctgctgata tagataatga tataagaaaa ctatcggaga tcccatcttt ttatttatca   780
tttggattaa cacctaaaca gggaggtgca ttgggtaata tgagtctcag aaaaatggat   840
tatagtgcta gtctgggtat cagttttcct ttgatgggat tatttagttc ttcagaaaat   900
caaaaagaaa agattatttc tatatctcga accagaaatg aattattgaa agaaaatata   960
aaactagatc tgttggaaaa agagattcgc cagaaaattg ataaattaga gaaaaatctt  1020
gcgatgatga aaaatgaact agctctgaaa aaaggaaaa ttgagtatat aaattatcgc  1080
gtaaagaatg gacaagacga cgttatcact tatttgtcta gtgtagagaa tttacatgaa  1140
acagaaaatg aatttcagaa aattggatat gagattgaat attatagttt atatcattat  1200
tttcttctgc agcacatttc caatacaggg gaaatgtga                         1239
```

Figure 17

**Nucleotide sequence of *aatB* (SEQ ID NO:11)**

```
atgaaacaga aaatgaattt cagaaaattg gatatgagat tgaatattat agtttatatc    60
attattttct tctgcagcac atttccaata caggggaaat gtgataacta ctatggtgtt   120
ctacatggaa ataaaaacgt aaaatataag agtccttttg caggggttgt aatacttgag   180
gacatgattg aaggtaatgt ggtcactgtg gaaaggaagc tattttctgt cctgaatcat   240
gagtatactg caaagaaaga tattgtggcc atgaaaagaa atatggaaga gaaaaaacta   300
tctagattaa aaggagcaaa gatacattta acctctatgt tctcaaaagg gttaatttca   360
agagaaagct tgcatgatat agatgagaaa atcagcaata ctgaattgac tattatggga   420
ctggacatag agtcaaagaa tctggaacaa ctattaaagt tgtcatcacc atttttgcat   480
actcctttca ttattcgaaa tatcttcgta acaaatgagc agtatgtaaa tgcaggcgat   540
gatataatgt ctgtagaact tctggataat ttttatatag atgttaaatt cgatccggtc   600
agtataacag gaaatataag agacaagaga ataaggtatc gttctttggt taattctcta   660
atggggtctg caacagtagt caaaaatatc cgtgccagtg gagaatcaac tcaaggtgaa   720
gatacatcag gtctgcgctc tattacgctg ttaattgatg gggaccggaa tgaattgtcg   780
aatctattag atactgcgtt tgagattata atagatgatt ag                      822
```

Figure 18

Nucleotide sequence of *aatC* (SEQ ID NO:12)

```
atgattagag taaaaataca taaaaaacct atagaaaaca gaactatcct gaataatagc    60
actattgaga taaaagaggg atcgttcaat attattactg gcccgtctgg agttggaaag   120
acttcactgc ttaacattat tggtctatta gataatgcct ttgttggaga gtatgaactt   180
ttcggtaaaa aagtggaaat aaaagataat agcatcacta catatatcag aagaaaatat   240
tttggattca tctttcagga ttctctgatt aatgtaaagc aaaatgtctt aagaaatata   300
ctatgttctg tagattctca aaacataata gccgcaaggg aaagaattaa tgaagtcttg   360
gtgtctgttg gattgtcaaa tattaataat aatgtatcat ttctctccgg gggagaaaaa   420
caaagactag cacttgctag ggcattgata aaaaaaccca gtatactttt agcagatgaa   480
cctactgcta gtctagatat aaagaataaa aaattagtga tgaatatact atctgaatac   540
aataatcaag gaggaacagt cgttatggta actcatgatc ttgaactaat cgatgagaat   600
atgactttaa tccaactatt aaatacatag                                    630
```

Figure 19

**Nucleotide sequence of *aatD* (SEQ ID NO:13)**

```
atgaaattcg ctattgtctt attgtatttt tttgcctatt atcttgcagc aagaaaaaga    60
cgagtgagtc ttttttttac tattcttta tactctatca ttttctctgg gatgtatttt   120
tctagtggtt ttttagaata ttatggcagt tctaatttat acctttcatt tggattactc   180
tgctataata tgataaccct tgtcatatat ggtttcctga gttcttatgg gttacttgga   240
gcatgtctac atgcactttc attaacctca ttatccgcct tcgggatgtt tataccatta   300
aatccattga ttgttttata ttatgatttt cctagcatct taccaagaac agatattcct   360
gttttaaatt tattaatatt aaatcttatt cctgcagtta catttagtct aaaaatatca   420
ttttttctcc gttctcttat attattattg ttatttccgc taatatggaa aacgccggtt   480
aatataactc atcccctct gaacattgtg attgtacagg ttggccttta ttttaaaaaa   540
gtaggtgtca gaggtaattt ttatacggat ctcaatgagt tcgtcagaaa taagaaggtt   600
gatctaatta ttctctcaga aaatgttttt ttcggttaca agaatgatta tataaaggaa   660
agaactaaac atctcttaaa gcaattaaaa gataatcgac tccactacaa atatgggata   720
ttaatgaatc tttatggata tcaagacatt aataacgtag tgtctgcttt ctggcataaa   780
gaagaatttc ttctccacca aaaagcaaa ttgataccttt ttttgagaa gaaagttt    840
tataactcac cagaaccatc gacatcacct tttctatatt ataaaagaa atataatgag   900
caggacatcc tggatttcaa caacattaaa atgagtattc atatatgtta tgagggatta   960
ttccctgagg gtgaatctcg aagaaaagat atctccattg ttcaatccga ttattcatgg  1020
ttgagtgaca atcacaaata tgacaacacc cttattaatg gaagtatatt atcgaaattc  1080
tctgtttcgc cgaacactcc tcttattaat attcaaaatt atggtgggac agtttttata  1140
gacaataatt ggaaaattga tatggactta tttaataggt caaaaacgga accttttta   1200
tttacacaga tatga                                                   1215
```

POLYNUCLEOTIDES ENCODING NOVEL PROTEINS IN ENTEROAGGREGATIVE *ESCHERICHIA COLI* (EAEC) USEFUL FOR DIAGNOSIS AND THERAPY OF EAEC INFECTIONS

CROSS REFERENCE TO RELATED APPLICATIONS

This application is a Continuation of U.S. application Ser. No. 10/847,391, filed May 18, 2004 and issued as U.S. Pat. No. 7,087,741; which is a Divisional of U.S. application Ser. No. 10/307,294, filed Dec. 2, 2002 and issued as U.S. Pat. No. 7,141,662; which claims priority under 35 U.S.C. §119(e) to provisional applications U.S. Ser. Nos. 60/334,425 and 60/398,775, filed Nov. 30, 2001, and Jul. 26, 2002, respectively, the contents of which are incorporated herein by reference in their entirety.

STATEMENT OF GOVERNMENTAL INTEREST

This invention was made with U.S. Government support under NIADA grant No. AI33096 awarded by the National Institutes of Health. The U.S. Government has certain rights in this invention.

FIELD OF THE INVENTION

The present invention relates generally to novel proteins and genes in enteroaggregative *Escherichia coli* (EAEC), and more particularly, to the use of these proteins and their corresponding nucleotide sequences for diagnosis, therapy, and prevention of EAEC infections.

BACKGROUND OF THE INVENTION

Enteroaggregative *Escherichia coli* (EAEC) is an emerging enteric pathogen associated with sporadic, endemic, and epidemic diarrheal illnesses in individuals of all ages in both developing and industrialized countries. (Nataro et al., *Emerg Infect Dis* 4:251-261 (1998); Nataro et al., *Clin Microbiol Rev.* 11:142-201 (1998); Okeke et al., *Lancet Infect Dis* 1:304-313 (2001)). The pathogenesis of EAEC infection includes strong adherence to the intestinal mucosa, most likely to both the small and the large intestines, followed by secretion of one or more enterotoxins that induce cytopathic effects in intestinal epithelial cells. (Nataro et al., *Infect Immun* 64:4761-4768 (1996); Eslava et al., *Escherichia coli. Infect Immun* 66:3155-3163 (1998); Czeczulin et al., *Infect Immun* 67:2692-2699 (1999)). Adherence of EAEC to the intestinal mucosa is characterized by the presence of a thick aggregating biofilm, which may favor the persistence of this organism in the human intestine. (Nataro et al., *Clin Microbiol Rev.* 11: 142-201 (1998); Tzipori et al., *Infect Immun* 60:5302-5306(1992)). In addition, EAEC may induce intestinal inflammation, which can precipitate growth failure even in the absence of diarrhea. (Steiner et al., *J Infect Dis* 177:88-96 (1998)).

The defining feature of EAEC is its distinctive characteristic aggregative adherence (AA) pattern to HEp-2 cells in culture. (Nataro et al., *Pediatr Infect Dis J* 6:829-831 (1987)). In particular, EAEC adhere to the surface of HEp-2 cells, to the glass substratum, and to each other in a distinctive stacked-brick formation. Aggregating adherence to HEp-2 cells in well-characterized strains requires the expression of one or more members of the plasmid-borne Aggregative Adherence Fimbriae (AAF) family. (Nataro et al., *Infect Immun* 60:2297-2304 (1992); Czeczulin et al., *Infect Immun* 65:4135-4145 (1997)). Two of members of the AAF family, AAF/I and AAF/II, have been characterized at the genetic level and each is encoded on a large plasmid (designated pAA). (Savarino et al., *J Bacteriol* 176:4949-57 (1994); Elias et al., *J Bacteriol* 181:1779-85 (1999)). It has been shown that the human pathogenic strain 042 requires AAF/II fimbrial antigen for adherence of the bacterium to the colonic mucosa, thereby suggesting that this adhesin is a virulence factor for human infection. (Czeczulin et al., *Infect Immun* 65:4135-4145 (1997)).

It has been shown that the majority of EAEC strains lack AAF/I and AAF/II. (Czeczulin et al., *Infect Immun* 67:2692-2699 (1999)). Nevertheless, most EAEC strains carry the ca. 100 kb pAA plasmid, recognized by the presence of several conserved loci. The most prominent among these loci is a transcriptional activator of the AraC class designated AggR, which is required for expression of both AAF/I and AAF/II. AggR is also present in a large percentage of EAEC strains that do not express any identified AAF. (Nataro et al., *J Bacteriol* 176:4691-4699 (1994)). Recently, a novel AggR-dependent gene lying immediately upstream of AggR in EAEC 042 has been identified and characterized. (Sheikh et al., *J Clin Invest* (in press) (2002)). This AggR-dependent gene encodes a secreted 10.2 kD protein, designated Aap, that appears to coat the bacterial surface and promote dispersion of EAEC on the intestinal mucosa. Aap has alternatively been designated dispersin. It has been shown that Aap mutants form larger aggregates, fewer individual bacteria, and aggregate more intensely than the wild type. In addition, Aap partially counteracts AAF-mediated aggregation and may play a fundamental role in EAEC pathogenesis. Moreover, the data suggest that Aap binds non-covalently to the bacterial cell surface. However, the mechanism by which Aap is translocated across the outer membrane is as yet unknown.

Another prominent locus is the binding site of a DNA probe, CVD432, on the plasmid. The CVD432 probe was developed to simplify the identification of EAEC and has been used as the AA probe. (Baudry et al., *J Infect Dis* 161: 1249-1251 (1990)). In its original evaluation, the probe was found to be 89% sensitive and 99% specific for EAEC. The nucleotide sequence of the AA probe represented a cryptic open reading frame (ORF) located adjacent to the plasmid replicon. (Nataro et al., *Infect Immun* 64:4761-4768 (1996)). Further sequence analysis of the AA probe region revealed five ORFs. The predicted protein of one of the ORFs was similar with the ATP-binding cassette (ABC) domain of the ABC transporter, suggesting that the gene cluster is involved in the transport of an unidentified molecule of EAEC. Furthermore, this gene cluster appears to be associated with the translocation of Aap, and the formation of a new transporting system of the virulence factor of EAEC. The five gene cluster was designated aat.

EAEC infections are medically important in populations around the world. For example, in developing countries, children are often infected with EAEC and can develop prolonged diarrhea, often with significant malnutrition. In industrialized countries, EAEC is an emerging cause of traveler's diarrhea. An effective vaccine to protect against enterotoxigenic *E. coli* would protect against at least one-half of traveler's diarrhea cases. However, in the past, there has been no effective treatment or prevention of EAEC-induced illnesses.

It is therefore desirable to identify and characterize Aap and the five gene cluster (aat) of the AA probe region of the pAA plasmid of EAEC 042 and to use these proteins and their corresponding nucleotide sequences for diagnosis, therapy, and prevention of EAEC infections.

SUMMARY OF THE INVENTION

Accordingly, it is an object of the present invention to identify and characterize Aap, AatP, AatA, AatB, AatC, and AatD, and fragments of these proteins, for diagnosis, therapy, and prevention of EAEC infections. It is also an object of this invention to identify and characterize aap, aatP, aatA, aatB, aatC, and aatD (the aat gene cluster or the aat cluster), and fragments of these genes, for diagnosis, therapy, and prevention of EAEC infections.

One embodiment of the present invention relates to an immunogenic composition that includes a recombinant product of Aap, AatP, AatA, AatB, AatC, or AatD and a carrier. Various aspects of this embodiment relate to compositions in which the recombinant product of Aap, AatP, AatA, AatB, AatC, or AatD is a fragment of Aap, AatP, AatA, AatB, AatC, or AatD, respectively, full-length Aap, AatP, AatA, AatB, AatC, or AatD, respectively, or a product that is at least 95% homologous to Aap, AatP, AatA, AatB, AatC, or AatD respectively. The recombinant product of Aap, AatP, AatA, AatB, AatC, or AatD can comprise Aap, AatP, AatA, AatB, AatC, or AatD itself, respectively.

Another embodiment of the present invention relates to an isolated nucleotide sequence comprising aap, aatP, aatA, aatB, aatC, or aatD or a functional fragment thereof.

Yet another embodiment of the present invention relates to a purified polypeptide sequence encoding Aap, AatP, AatA, AatB, AatC, or AatD or a functional equivalent of Aap, AatP, AatA, AatB, AatC, or AatD.

A further embodiment of the present invention relates to methods of using the gene encoding for aap, aatP, aatA, aatB, aatC, or aatD, products, and fragments thereof. One particular embodiment disclosed herein teaches a method of generating an immune response that includes providing an immunogenic composition that includes Aap, AatP, AatA, AatB, AatC, or AatD, a functional fragment thereof, or a product thereof to a subject and contacting the subject with the immunogenic composition, which generates an immune response in the subject.

Another embodiment of the present invention relates to a method of producing a polypeptide product from a polynucleotide encoding aap, aatP, aatA, aatB, aatC, or aatD, or functional fragment thereof, that includes providing aap, aatP, aatA, aatB, aatC, or aatD in an expression vector, introducing the expression vector into a host cell such that a recombinant host cell is produced, and subjecting the recombinant host cell to conditions such that a protein from aap, aatP, aatA, aatB, aatC, or aatD is expressed.

An additional embodiment of the present invention relates to cells comprising recombinant aap, aatP, aatA, aatB, aatC, or aatD, or fragments thereof, and expression vectors comprising aap, aatP, aatA, aatB, aatC, or aatD, or fragments thereof.

Yet another embodiment of the present invention relates to antibodies and antibody fragments that bind to and recognize Aap, AatP, AatA, AatB, AatC, or AatD, or fragments of Aap, AatP, AatA, AatB, AatC, or AatD.

A further embodiment of the present invention relates to the diagnosis of diseases caused by enteroaggregative E. coli (EAEC). The diagnosis of diseases caused by EAEC can be performed by using antibodies or fragments of antibodies that bind to and recognize Aap, AatP, AatA, AatB, AatC, or AatD, or fragments of Aap, AatP, AatA, AatB, AatC, or AatD. An alternative embodiment of the present invention relating to the diagnosis of diseases caused by EAEC relates to the use of polynucleotides that are complementary to aap, aatP, aatA, aatB, aatC, or aatD, or portions of aap, aatP, aatA, aatB, aatC, or aatD to diagnose the disease caused by EAEC.

Additional embodiments of the present invention encompass kits that utilize antibodies or fragments of antibodies that bind to and recognize Aap, AatP, AatA, AatB, AatC, or AatD or fragments of Aap, AatP, AatA, AatB, AatC, or AatD, kits that utilize antibodies or other proteins (i.e., Aap, AatP, AatA, AatB, AatC, or AatD), and kits that utilize polynucleotides that bind to and recognize aap, aatP, aatA, aatB, aatC, or aatD, or fragments of aap, aatP, aatA, aatB, aatC, or aatD. These kits can be used for the diagnosis of disease caused by EAEC and for diagnosis of EAEC infections.

It is a feature of the present invention that isolated and purified polynucleotide molecules encoding the Aap protein are capable of hybridizing under moderate to stringent conditions to an oligonucleotide of 15 or more contiguous nucleotides of SEQ ID NO: 1 or its complementary strand.

It is another feature of the present invention that isolated and purified polynucleotide molecules encoding the AatP protein are capable of hybridizing under moderate to stringent conditions to an oligonucleotide of 15 or more contiguous nucleotides of SEQ ID NO: 9 or its complementary strand.

It is a yet another feature of the present invention that isolated and purified polynucleotide molecules encoding the AatA protein are capable of hybridizing under moderate to stringent conditions to an oligonucleotide of 15 or more contiguous nucleotides of SEQ ID NO: 10 or its complementary strand.

It is a further feature of the present invention that isolated and purified polynucleotide molecules encoding the AatB protein are capable of hybridizing under moderate to stringent conditions to an oligonucleotide of 15 or more contiguous nucleotides of SEQ ID NO: 11 or its complementary strand.

It is also a feature of the present invention that isolated and purified polynucleotide molecules encoding the AatC protein are capable of hybridizing under moderate to stringent conditions to an oligonucleotide of 15 or more contiguous nucleotides of SEQ ID NO: 12 or it is complementary strand.

It is a further feature of the present invention that isolated and purified polynucleotide molecules encoding the AatD protein are capable of hybridizing under moderate to stringent conditions to an oligonucleotide of 15 or more contiguous nucleotides of SEQ ID NO: 13 or its complementary strand.

The foregoing and other objects, features, and advantages of the invention will appear more fully hereinafter from a consideration of the detailed description that follows, in conjunction with the accompanying sheets of figures. It is to be expressly understood, however, that the drawings are for illustrative purposes and are not to be construed as defining the limits of the invention.

BRIEF DESCRIPTION OF THE DRAWINGS

The advantages of this invention will be apparent upon consideration of the following detailed disclosure of the invention, especially when taken in conjunction with the accompanying drawings wherein:

FIG. 1 illustrates the nucleotide sequence of aap (SEQ ID NO:1);

FIG. 2 illustrates the amino acid sequence of Aap (SEQ ID NO:2);

FIG. 9 illustrates the nucleotide sequence of the 7 kb fragment of pAA of EAEC 042 (SEQ ID NO: 3);

FIG. 10 illustrates the amino acid sequence of AatP (SEQ ID NO: 4).

FIG. 11 illustrates the amino acid sequence of AatA (SEQ ID NO: 5).

FIG. 12 illustrates the amino acid sequence of AatB (SEQ ID NO: 6).

FIG. 13 illustrates the amino acid sequence of AatC (SEQ ID NO: 7).

FIG. 14 illustrates the amino acid sequence of AatD (SEQ ID NO: 8).

FIG. 15 illustrates the nucleotide sequence of aatP (SEQ ID NO: 9).

FIG. 16 illustrates the nucleotide sequence of aatA (SEQ ID NO: 10).

FIG. 17 illustrates the nucleotide sequence of aatB (SEQ ID NO: 11).

FIG. 18 illustrates the nucleotide sequence of aatC (SEQ ID NO: 12).

FIG. 19 illustrates the nucleotide sequence of aatD (SEQ ID NO: 13).

DETAILED DESCRIPTION OF THE INVENTION

Figure 3:
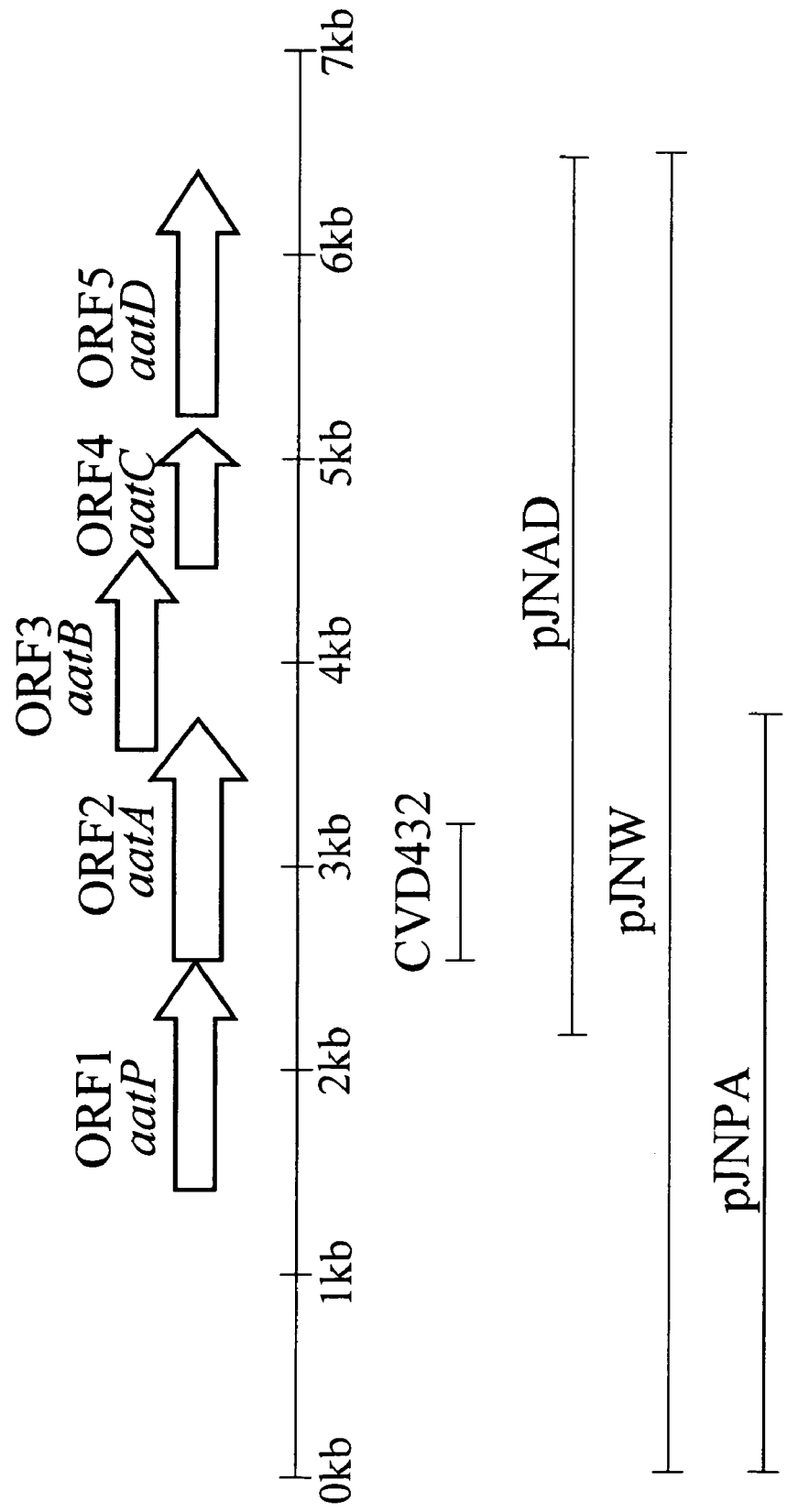
FIG. 3 is a map of 7 kb fragment of the pAA plasmid of EAEC 042 showing the location of the aat gene cluster.

This invention covers Aap (for Anti-aggregation protein, also called dispersin), AatP, AatA, AatB, AatC, and AatD which are all proteins found in enteroaggregative E. coli (EAEC). This invention also covers the genes for these proteins (aap, aatP, aatA, aatB, aatC, and aatD) and fragments of the genes and proteins, and use of these proteins, genes, and fragments thereof for diagnosis and therapy of EAEC infections. The following genes are also called the aat gene cluster: aatP, aatA, aatB, aatC, and aatD.

Aap is secreted from enteroaggregative E. coli (EAEC) and modulates the strong aggregative phenotype of EAEC on the intestinal mucosa. The secretion of Aap does not negatively affect EAEC fimbrial expression or fimbrial biogenesis. Aap is a 116 amino acid protein, has a molecular weight of about 10.2 kilodaltons (kDa) as determined by SDS-PAGE, a pI of approximately 9.25, and an amino acid sequence illustrated in FIG. 2 (SEQ ID NO: 2). SIGNALP analysis strongly predicts a signal sequence with cleavage after position 21. An N-terminal amino acid sequence of Aap from bacterial culture supernatants confirms this cleavage.

aap is 348 base-pairs (bp) in length and has the polynucleotide sequence illustrated in FIG. 1 (SEQ ID NO: 1). aap is located on the pAA plasmid (ca. 100 kp) of prototype EAEC strain 042 (EAEC 042) upstream of the aggR gene which is located downstream of the fimbrial subunit (aafA). Sequencing of the pAA plasmid DNA upstream of aggR revealed an open reading frame 843 nucleotides upstream from the aggR start codon. This open reading frame was 348 nucleotides in length and encoded a predicted protein product of 116 amino acids. Analysis with SIGNALP (a web-based algorithm which predicts the site of signal sequence processing) strongly predicted a signal sequence with cleavage after position 21. N-terminal amino acid sequence of Aap from bacterial culture supernatants confirmed the cleavage signal sequence and the sequence indicated in FIG. 2.

The pAA plasmid not only contains putative virulence factors AAF, Aap (dispersin), Pet, EAST1, and AggR but also contains sequences homologous to an empirically derived probe sensitive to EAEC strains (the "AA probe"). (Baudrey et al., *J Infect Dis* 161:1249-1251 (1990)). The region comprising the AA probe (i.e., the insert of plasmid pCVD432) has been shown to be associated with pathogenic EAEC strains and to correlate with the presence of plausible virulence factors. (Okeke et al., *J Infect Dis* 81:252-60 (2000); Cohen, M. and Nataro, J. P., unpublished). Although the 765 bp sequence of the probe itself has been previously reported (Schmidt et al., *J Clin Microbiol* 33:701-5 (1995)), it was noted that the sequence did not contain stop codons in one potential reading frame. A 7 kb sequence of the pAA2 plasmid was determined by shotgun sequencing of a pBluescript library (see FIG. 9 (SEQ ID NO: 3)). Discrepancies were resolved by directed sequencing of pBluescript clones comprising the desired region.

Analysis of the DNA sequence of this region of the probe reveal a cluster of five open reading frames (ORFs) in the same rightward orientation and very closely spaced. (See FIG. 3). This cluster of ORF's is known as the aat gene cluster or aat cluster because two of genes in this cluster exhibit significant homology to bacterial ABC transporter proteins thus is short for enteroaggregative ABC transporter. The aat gene cluster features very low G+C ratios, ranging from 29.6 to 34.3. The aat gene cluster contains aatP, aatA, aatB, aatC, and aatD. Flanking the aat gene cluster at distances of over 500 bp on each side are remnants of IS sequences.

The nucleotide sequence of aatP is shown in FIG. 15 (SEQ ID NO: 9). The amino acid sequence for AatP is shown in (SEQ ID NO: 4). AatP is a predicted protein of 377 amino acids (42.7 kDa) and runs from nucleotide 1425 to 2555 of the 7 kb fragment from pAA as shown in FIG. 9. AatP is 20% identical at the amino acid level over its entire length to permease components of ABC-type transport systems that are involved in lipoprotein release. The protein has five transmembrane regions and is be believed to be an inner membrane protein, based on computer analysis.

The nucleotide sequence of aatA is shown in FIG. 16 (SEQ ID NO: 10). The amino acid sequence for AatA is shown in FIG. 11 (SEQ ID NO: 5). AatA is a predicted protein of 413 amino acids (48.5 kDa) and runs from nucleotide 2552 to 3790 of the 7 kb fragment from pAA as shown in FIG. 9 (SEQ ID NO: 3). SignalP analysis strongly predicts a signal sequence with cleavage after position 23. The predicted mature protein of 391 amino acids is 45.9 kDa in size. Neither the nucleotide sequence nor the deduced amino acid sequence of aatA display's significant identity to any other known gene or protein. AapA has a coiled coil region and is believed to be an outer membrane or periplasmic protein.

The nucleotide sequence of aatB is shown in FIG. 17 (SEQ ID NO: 11). The amino acid sequence for AatB is shown in FIG. 12 (SEQ ID NO: 6). AatB is a predicted protein of 274 amino acids (31.1 kDa) and runs from nucleotide 3687 to 4508 of the 7 kb fragment from pAA as shown in FIG. 9 (SEQ ID NO: 3). AatB does not have any significant homology to any known protein sequences in the GenBank library. The protein has a transmembrane region in the N-terminus and is believed to be an inner membrane protein.

The nucleotide sequence of aatC is shown in FIG. 18 (SEQ ID NO: 12). The amino acid sequence for AatC is shown in FIG. 13 (SEQ ID NO: 7). AatC is a predicted protein of 210 amino acids (23.3 kDa) and runs from nucleotide 4501 to 5130 of the 7 kb fragment from pAA as shown in FIG. 9 (SEQ ID NO: 3). AatC is 45% identical at the amino acid level over its entire length to an ABC transporter ATP-binding protein. ABC domains of E. coli have four short motifs that are invariably conserved: Walker A, Walker B, ABC signature, and the histidine motif (Linton 1998). All these motifs were conserved in AatC.

The nucleotide sequence of aatD is shown in FIG. 19 (SEQ ID NO: 13). The amino acid sequence for AatD is shown is FIG. 14 (SEQ ID NO: 8). AatD is a predicted protein of 405 amino acids (47.2 kDa) and runs from nucleotide 5142 to 6356 of the 7 kb fragment from pAA as shown in FIG. 9 (SEQ ID NO: 3). AatD is 29% identical at the amino acid level over 34% of its length to NADH dehydrogenase subunit 2. AatD has five transmembrane regions in the N-terminal and is believed to be an inner membrane protein.

For each of the above discussed genes, additional polynucleotide molecules that encode the proteins discussed above include those polynucleotide sequences resulting in minor genetic polymorphisms, differences between strains, degenerate variants, and encoding for proteins that contain amino acid substitutions, additions, and/or deletions.

Nucleotide sequences encoding aap and/or the aat gene cluster can be used to identify polynucleotide molecules encoding other proteins with biological functions similar to that of Aap and/or the proteins of the aat gene cluster by screening a cDNA library or DNA library from other organisms (prokaryotic or eukaryotic). These new DNA molecules can be isolated from such a library using the polynucleotide sequence disclosed herein with standard hybridization techniques or the amplification of sequences using polymerase chain reaction (PCR) amplification. Suitable probes for use in identifying protein homolog sequences can be obtained from gene-specific sequences. Alternatively, oligonucleotides containing specific DNA sequences from coding region for these genes can be used to identify related clones. One of ordinary skill in the art will appreciate that the regulatory regions of the genes and homologous genes can be obtained using similar methods.

Homologous polynucleotide molecules can be isolated using standard hybridization techniques with probes of at least about 7 nucleotides, more preferably 15 nucleotides, in length (but can be as much as the full coding sequence). Homologous polynucleotide sequences can be identified using degenerate oligonucleotides based on the sequences disclosed herein which are capable of hybridization at moderate or greater stringency. The term, "capable of hybridization" as used herein means that the subject nucleic acid molecules (whether DNA or RNA) anneal to an oligonucleotide of 15 or more contiguous nucleotides of one of the polynucleotide sequences disclosed herein.

The choice of hybridization conditions will be evident to one ordinarily skilled in the art and will generally be guided by the purpose of the hybridization, the type of hybridization (DNA-DNA or DNA-RNA), and the level of desired relatedness between the sequences. Methods for hybridization are well established in the literature. One of ordinary skill in the art realizes that the stability of nucleic acid duplexes decrease with an increased number and location of mismatched bases. As a result, the stringency of hybridization can be used to maximize or minimize the stability of such duplexes. Hybridization stringency can be altered, for example, by adjusting the temperature of hybridization, adjusting the percentage of helix-destabilizing agents (e.g., formamide) in the hybridization mix, and adjusting the temperature and salt concentration of the wash solutions. In general, the stringency of hybridization is adjusted during post-hybridization washes by varying the salt concentration and/or the temperature, which results in progressively higher stringency conditions.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. Optimal conditions will vary depending on the particular hybridization reaction involved, and can be determined empirically. Conditions of high stringency are preferably used for the hybridization of the probe of interest.

Alternatively, polynucleotides having substantially the same nucleotide sequence as or are substantially identical to one of the polynucleotide sequences of aap or the aat gene cluster represent aap-like or aat gene cluster-like genes. Also polynucleotides which encode for proteins that are functionally equivalent of, or functional fragments of Aap or the proteins of the aat gene cluster are included in this invention. "Substantially the same" or "substantially identical" is meant a nucleic acid, polynucleotide, or polypeptide exhibiting at least 80%, 85%, 90%, 91%, 92%, 93%, 94%, 95%, 96%, 97%, 98%, 99%, or 100% homology to a reference nucleic acid, polynucleotide, or polypeptide. For nucleotide sequences, the length of comparison sequences will generally be at least 10 to 500 nucleotides in length. Preferably, the length of comparison will be at least 50 nucleotides, more preferably at least 60 nucleotides, even more preferably at least 75 nucleotides, and most preferably at least 110 nucleotides in length.

An "isolated" nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into an expression vector or into the genomic DNA of a prokaryote or eukaryote in a manner such that the resulting molecule is not identical to naturally occurring expression vector or genomic DNA; (c) a separate molecule such as cDNA, a genomic fragment, a fragment produced by polymerase chain reaction (PCR), or a restriction fragment; and (d) a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

DNA sequences of the invention can be obtained by several methods. For example, the DNA can be isolated using hybridization or computer-based techniques that are well-known in the art. Such techniques include, but are not limited to, the hybridization of genomic or cDNA libraries with probes to detect homologous nucleotide sequences; antibody screening of expression libraries to detect cloned DNA fragments with shared structural features; polymerase chain reaction (PCR) on genomic DNA or cDNA using primers capable of annealing to the DNA sequence of interest; computer searches of sequence databases for similar sequences; and differential screening of a subtracted DNA library.

Screening procedures that rely on nucleic acid hybridization make it possible to isolate any gene sequence from any organism, provided the appropriate oligonucleotide probe is available. Oligonucleotide probes, which correspond to a part of the sequences for aap or the aat gene cluster which are provided herein, can be synthesized chemically. Synthesis of other oligonucleotide probes may require that short, oligopeptide stretches of the amino acid sequence be known because the DNA sequence encoding a specific protein can be deduced using the genetic code; however, the degeneracy of the code must be taken into account. When the sequence is degenerate, it is possible to perform a mixed addition reaction that includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA or DNA clone by the hybridization of the target DNA to that single probe in the mixture that is its complete complement. (Wallace et al., *Nuc. Acid Res.* 9:879 (1981)). Alternatively, a subtractive library is useful for elimination of non-specific cDNA clones.

Another standard procedure for isolating DNA sequences of interest is the formation of plasmid- or phage-carrying genomic libraries which include total DNA from the organism of interest. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target DNA can be employed in DNA/DNA hybridization procedures which are carried out on cloned copies of the DNA that have been denatured into a single-stranded form. (Jay et al., *Nucl. Acid Res.*, 11:2325 (1983).

The nucleotide sequences of aap and the aat gene cluster have a myriad of applications. Representative uses of these nucleotide sequences include the construction of DNA and oligonucleotide probes useful in Northern, Southern, immuno-PCR, dot-blot, and other assays for detecting EAEC, quantifying the level of expression of Aap, AatP, AatA, AatB, AatC, or AatD in a cell, or generating the particular protein or polypeptide which is encoded by the nucleotide sequence. aap and the aat gene cluster nucleotide sequences can be employed for the construction of recombinant cell lines, recombinant organisms, expression vectors, and the like. Such recombinant constructs can be used to express recombinant Aap, AatP, AatA, AatB, AatC, and/or AatD, and can be used as vaccines (via a live, attenuated vector vaccine or other type of invasive vector vaccine) or to screen for candidate therapeutic agents capable of altering the pathology of an organism expressing one or more these proteins.

Considering the important role these proteins plays in EAEC aggregation, penetration of the mucosal mucous blanket, attachment, and colonization, the proteins or polypeptides of this invention are highly useful in the generation of immunogenic compositions that can be used to generate an immune response in a subject (e.g., via a subunit vaccine) and in kits for the detection of EAEC. For a subunit vaccine, one or more of the proteins of this invention can be expressed, purified, and used to prepare an immunogenic subunit composition. For a live, attenuated vector vaccine, one or more of the proteins of this invention can also be expressed in an attenuated, invasive bacteria or virus, and the whole organism can be formulated into an immunogenic composition. In another type of vaccine, one or more of the genes of this invention can be placed on a plasmid downstream of a signal sequence of an eukaryotic promoter. That plasmid can contain one or more selectable markers and be transfected into a prokaryotic organism, such as *Salmonella* spp., *Shigella* spp., or other suitable bacteria. The bacteria is then administered to the eukaryotic subject for which immune response to EAEC is desired. See, for example, U.S. Pat. No. 5,887,159 to Hone, et al. Additionally, a polynucleotide encoding one of the proteins of this invention can be administered to the mucosal tissue of a subject to generate an immunogenic response. See, for example, U.S. Pat. No. 6,110,898 to Malone et al. Also, a naked polynucleotide encoding one of the proteins of this invention can be electroporated into a subject to generate an immune response using the methods described within Drabick, J. J.; e al.; *Cutaneous transfection and immune responses to intradermal nucleic acid vaccination are significantly enhanced by in vivo electropermeabilization*, Mol. Ther. Vol 3(2); pp. 249-55 (2001).

The genes of this invention can also be placed into expression vectors which are discussed more fully below.

Antisense

Antisense nucleotide sequences to the genes of this invention can be used to block expression of proteins of this invention. Suitable antisense oligonucleotides are at least 11 nucleotides in length and can include untranslated (upstream) and associated coding sequences. As known by those of skill in the art, the optimal length of an antisense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structures in the mRNA and/or in the antisense oligonucleotide. Suitable target sequences for antisense oligonucleotides include promoter regions, ribosome binding sites, and sites that interfere with ribosome progression.

Antisense oligonucleotides can be prepared, for example, by inserting a DNA molecule containing the target DNA sequence into a suitable expression vector such that the DNA molecule is inserted downstream of a promoter in a reverse orientation as compared to a particular gene of this invention. The expression vector can then be transduced, transformed, or transfected into a cell (prokaryotic and/or eukaryotic) suitable for expressing the antisense oligonucleotides. Alternatively, antisense oligonucleotides can be synthesized using standard manual or automated synthesis techniques. These synthesized oligonucleotides are introduced into suitable cells by a variety of means including electroporation, calcium phosphate precipitation, and microinjection. The selection of a suitable antisense oligonucleotide administration method would be evident to one of ordinary skill in the art.

With respect to synthesized oligonucleotides, the stability of antisense oligonucleotide-mRNA hybrids is advantageously increased by the addition of stabilizing agents to the oligonucleotide. One example of a stabilizing agent includes intercalating agents that are covalently attached to either or both ends of the oligonucleotide. In preferred embodiments, the oligonucleotides are made resistant to nucleases by modifications to the phosphodiester backbone by the introduction of phosphotriesters, phosphonates, phosphorothioates, phosphoroselenoates, phosphoramidates, phosphorodithioates, or morpholino rings.

Amino Acids

"Aap", "AatP", "AatA", "AatB", "AatC", and "AatD", as described herein, encompass the whole protein (Aap, AatP, AatA, AatB, AatC, and AatD respectively), fragments of the protein (Aap, AatP, AatA, AatB, AatC, and AatD respectively) that are functionally active, and polypeptides that contain substitutions such as one basic amino acid for another basic amino acid, or one acidic amino acid for another acid amino acid, or one neutral amino acid for another neutral amino acid. "Aap", "AatP", "AatA", "AatB", "AatC", and "AatD" also encompass Aap, AatP, AatA, AatB, AatC, and AatD respectively purified from naturally occurring materials and closely related, functionally similar proteins retrieved by antisera specific to the particular protein. Recombinantly expressed proteins encoded by genetic materials (DNA, RNA, cDNA) retrieved on the basis of their similarity to regions in the particular gene sequence are also encompassed by the present description.

Polynucleotide molecules encoding Aap, AatP, AatA, AatB, AatC, and AatD include molecules that encode Aap, AatP, AatA, AatB, AatC, and AatD, respectively, or peptides that share identity with the sequence shown in SEQ ID NO: 2 (FIG. 2); SEQ ID NO: 4 (FIG. 10); SEQ ID NO: 5 (FIG. 11); SEQ ID NO: 6 (FIG. 12); SEQ ID NO: 7 (FIG. 13), and SEQ ID NO: 8 (FIG. 14) respectively. These molecules preferably share greater than 30% identity at the amino acid level with the disclosed protein. In preferred embodiments, the polynucleotide molecules share greater identity at the amino acid level across highly conserved regions. Variants of a particular gene encoded protein include those amino acid sequences resulting from minor genetic polymorphisms, differences between strains, and those that contain amino acid substitutions, additions, and/or deletions, and conservative amino acid substitutions. A conservative amino acid substitution includes a replacement of one amino acid residue with a different residue having similar biochemical characteristics, such as size, charge, and polarity vs. nonpolarity.

Amino acid sequences substantially the same as the sequences set forth in SEQ ID NO: 2; SEQ ID NO: 4; SEQ ID NO: 5; SEQ ID NO: 6; SEQ ID NO: 7; and SEQ ID NO: 8 are encompassed by the present description. A preferred embodiment includes polypeptides having substantially the same sequence of amino acids as the sequences described herein, functional fragments thereof, or amino acid sequences that are substantially identical to the sequences described herein. As described above, "substantially the same" or "substantially identical" is meant a polypeptide exhibiting at least 80%, 85%, 90%, 91%, 92%, 93%, 94%, 95%, 96%, 97%, 98%, 99%, to 100% homology to a reference amino acid sequence. For polypeptides, the length of comparison sequences will generally be at least 16 amino acids, preferably at least 20 amino acids, more preferably at least 25 amino acids, and most preferably at least 35 amino acids.

Homology of sequences is often measured using sequence analysis software (e.g., Sequence Analysis Software Package of the Genetics Computer Group, University of Wisconsin Biotechnology Center, 1710 University Avenue, Madison, Wis. 53705 or the NCBI BLAST program). Such software matches similar sequences by assigning degrees of homology to various substitutions, deletions, substitutions, and other modifications.

The term "substantially identical" also means an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence that do not destroy the function of the protein assayed, (e.g., as described herein). Preferably, such a sequence is at least 85%, and more preferably from 90%, 91%, 92%, 93%, 94%, 95%, 96%, 97%, 98%, 99%, to 100% homologous at the amino acid level to sequences described herein.

The term "functional fragments" include fragments of the proteins described herein that have a similar amino acid sequence and that retain the function or activity of the particular protein. Where full-length protein is described, one of skill in the art can screen for the functionality of a fragment by using the examples provided herein.

The term "substantially pure polypeptide" as used herein means an polypeptide that has been separated from components that naturally accompany it. Typically, the polypeptide is substantially pure when it is at least 60%, by weight, free from the proteins and other naturally occurring molecules with which it is typically associated. Preferably, the preparation is at least 75%, 80%, 90%, 95%, and most preferably at least 99%, by weight. A substantially pure protein can be obtained, for example, by extraction from a natural source, by expression of a recombinant nucleic acid encoding a particular protein, or by chemically synthesizing the protein. Purity can be measured by any appropriate method, such as column chromatography, polyacrylamide gel electrophoresis, and HPLC analysis.

A protein is substantially free of naturally associated components when it is separated from those contaminants that accompany it in its natural state. Thus, a protein that is chemically synthesized or produced in a cellular system different from the cell or host from which it naturally originates is substantially free from its naturally associated components. Accordingly, substantially pure polypeptides include those derived from prokaryotic organisms but synthesized in eukaryotic organisms. A purified polypeptide is a polypeptide substantially free of naturally associated components when it is separated from those contaminants that accompany it in its natural state. As would be evident to one ordinarily skilled in the art, the polynucleotide molecules according to the present disclosure can be expressed in a variety of prokaryotic and eukaryotic cells using regulatory sequences, expression vectors, and methods well established in the literature to produce a polypeptide or protein which can be purified.

Purification of a protein of this invention can be performed using a number of established methods such as affinity chromatography using antibodies specific to a particular protein coupled to a solid support. Fusion proteins of an antigenic tag and the protein of interest can be purified using antibodies to the tag. Optionally, additional purification is achieved using conventional purification means such as liquid chromatography, gradient centrifugation, or gel electrophoresis. Methods of protein purification are well known in the art and can be applied to the purification of recombinant proteins described herein. The purification of the proteins of this invention is discussed in more detail below.

Fusion proteins typically contain additions, substitutions, or replacements of one or more contiguous amino acids of the native protein with amino acid(s) from a suitable fusion protein partner. Such fusion proteins are obtained using recombinant DNA techniques easily identified and well known by those of skill in the art. For example, DNA molecules encoding the hybrid Aap fusion protein of interest are prepared using generally available methods such as PCR mutagenesis, site-directed mutagenesis, and/or restriction digestion and ligation. The hybrid DNA is then inserted into expression vectors and introduced into suitable host cells.

One embodiment of the present invention involves the isolation of proteins that interact with the proteins described herein or are receptors for the proteins described herein. Aap, AatP, AatA, AatB, AatC, and/or AatD can be used in immunoprecipitation to isolate interacting factors or for the screening of interactors using different methods of two hybrid screening. Isolated interactors of these proteins can be used to modify or block activity of the particular protein in a host or between EAEC.

Synthetic peptides, recombinantly derived peptides, fusion proteins, chiral proteins (stereochemical isomers, racemates, enantiomers, and D-isomers), and the like are provided which include a portion of one of the proteins described herein or the entire protein. The subject peptides have an amino acid sequence encoded by a nucleic acid which hybridizes under stringent conditions with an oligonucleotide of 15 or more contiguous nucleotides of SEQ ID NO: 1; SEQ ID NO: 9; SEQ ID NO:10; SEQ ID NO: 11; SEQ ID NO: 12; or SEQ ID NO: 13. Representative amino acid sequences of the subject peptides is disclosed in SEQ ID NO: 2; SEQ ID NO: 4, SEQ ID NO: 5; SEQ ID NO: 6; SEQ ID NO: 7; or SEQ ID NO: 8. The subject peptides find a variety of uses, including preparation of specific antibodies and preparation of antagonists of activity the proteins described herein.

Antibodies That Bind To Aap, AatP, AatA, AatB, AatC, or AatD

The production of antisera or monoclonal antibodies (e.g., murine, lagomorph, porcine, equine, or human) is well known and can be accomplished by methods easily identified by one of skill in the art, such as, for example, immunizing an animal with one of the proteins described herein or a peptide derived from one of the proteins. For the production of monoclonal antibodies, antibody producing cells are obtained from immunized animals, immortalized, and screened. Alternatively, antibody producing cells are first screened for the production of the antibody that binds to a particular protein or the particular derived peptides and then immortalized. It can be desirable to transfer the antigen binding regions (e.g., F(ab')2 or hypervariable regions) of non-human antibodies into the framework of a human antibody by recombinant DNA techniques to produce a substantially human molecule.

Following synthesis or expression and isolation or purification of a particular protein or a portion thereof, the isolated or purified protein can be used to generate antibodies and tools for identifying agents that interact with that particular protein and fragments of interest. Depending on the context, the term "antibodies" can encompass polyclonal, monoclonal, chimeric, single chain, Fab fragments, and fragments produced by a Fab expression library. Antibodies that recognize Aap, AatP, AatA, AatB, AatC, and/or AatD and fragments thereof have many uses including, but not limited to, biotechnological applications, therapeutic/prophylactic applications, and diagnostic applications.

For the production of antibodies, various hosts including, but not limited to, goats, rabbits, rats, mice, humans, etc., can be immunized by injection with a particular protein or any portion, fragment, or oligopeptide that retains immunogenic properties. Depending on the host species, various adjuvants can be used to increase the immunological response. Such adjuvants include, but are not limited to, detoxified heat labile toxin from *E. coli*, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are also potentially useful adjuvants.

Peptides used to induce specific antibodies have an amino acid sequence of at least three amino acids, and preferably an amino acid sequence of at least 10 to 15 amino acids. Preferably, short stretches of amino acids encoding fragments of a particular protein are fused with those of another protein such as keyhole limpet hemocyanin such that an antibody is produced against the chimeric molecule. Although antibodies capable of specifically recognizing a particular protein of this invention can be generated by injecting synthetic 3-mer, 10-mer, and 15-mer peptides that correspond to an amino acid sequence of that particular protein into a host (e.g., mice), a more diverse set of antibodies can be generated by using a particular recombinant protein, a particular purified protein, or fragments of a particular protein.

To generate antibodies to Aap, AatP, AatA, AatB, AatC, AatD, and/or fragments thereof, a substantially pure Aap, AatP, AatA, AatB, AatC, AatD, or a fragment thereof is isolated from a transfected or transformed cell or the wildtype EAEC. The concentration of the polypeptide in the final preparation is adjusted, for example, by concentration on an Amicon filter device, to the level of a few micrograms/ml.

Monoclonal antibodies to Aap, AatP, AatA, AatB, AatC, AatD, or a fragment thereof can be prepared using any technique that provides for the production of antibody molecules by continuous cell lines in culture. Such techniques include, but are not limited to, the hybridoma technique originally described by Koehler and Milstein (*Nature* 256:495-497 (1975)), the human B-cell hybridoma technique (Kosbor et al., *Immunol Today* 4:72 (1983); Cote et al., *Proc Natl. Acad. Sci* 80:2026-2030 (1983)), and the EBV-hybridoma technique (Cole et al., *Monoclonal Antibodies and Cancer Therapy*, Alan R. Liss Inc, New York N.Y., pp 77-96 (1985)). Techniques developed for the production of "chimeric antibodies", i.e., the splicing of mouse antibody genes to human antibody genes to obtain a molecule with appropriate antigen specificity and biological activity, can also be used. (Morrison et al., *Proc Natl. Acad. Sci* 81:6851-6855 (1984); Neuberger et al., *Nature* 312:604-608(1984); Takeda et al., *Nature* 314: 452-454(1985)). Alternatively, techniques described for the production of single chain antibodies, such as disclosed in U.S. Pat. No. 4,946,778, incorporated herein by reference in its entirety, can be adapted to produce Aap-specific single chain antibodies. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci* 86: 3833-3837 (1989); and Winter G. and Milstein C., *Nature* 349:293-299 (1991).

Antibody fragments that contain specific binding sites for a particular protein of this invention can also be generated. For example, such fragments include, but are not limited to, F(ab')$_2$ fragments produced by pepsin digestion of the antibody molecule and Fab fragments generated by reducing the disulfide bridges of the F(ab')$_2$ fragments. Alternatively, Fab expression libraries can be constructed to allow rapid and easy identification of monoclonal Fab fragments with the desired specificity. (Huse W. D. et al., *Science* 256:1275-1281 (1989)).

One method of making monoclonal antibodies to Aap, AatP, AatA, AatB, AatC, AatD, or fragments thereof includes repetitively inoculating a mouse with a few micrograms of the selected protein or peptides over a period of a few weeks. The mouse is then sacrificed and the antibody producing cells of the spleen are isolated. These spleen cells are fused in the presence of polyethylene glycol and mouse myeloma cells. The excess unfused cells are destroyed by growth of the system on selective media comprising aminopterin (HAT media). The successfully fused cells are then diluted and aliquots of the dilution are placed in wells of a microtiter plate where growth of the culture is continued. Antibody-producing clones are identified by the detection of antibody in the supernatant fluid of the wells by immunoassay procedures such as ELISA, as originally described by Engvall, E., *Meth. Enzymol.* 70:419 (1980), and derivative methods thereof. Selected positive clones can be expanded and their monoclonal antibody product harvested for use. An example of a detailed procedure for monoclonal antibody production can be found in Davis, L. et al., *Basic Methods in Molecular Biology* Elsevier, New York. Section 21-2.

Polyclonal antiserum containing antibodies to heterogeneous epitopes of a single protein can be prepared by immunizing suitable animals with the expressed protein or peptides derived therefrom, which can be unmodified or modified to enhance immunogenicity. Effective polyclonal antibody production is affected by many factors related both to the antigen and to the host species. For example, small molecules tend to be less immunogenic than larger molecules and can require the use of carriers and adjuvants. Also, host animals vary in response to the site(s) of inoculations and dose, with both inadequate or excessive doses of antigen resulting in low titer antisera. Small doses (e.g., ng level) of antigen administered at multiple intradermal sites appears to be most reliable. An example of an effective immunization protocol for rabbits can be found in Vaitukaitis, J. et al., *J. Clin. Endocrinol. Metab.* 33:988-991 (1971).

Booster injections can be given at regular intervals, and antiserum harvested when the antibody titer thereof begins to fall. This fall in antibody titer can be determined semi-quantitatively, for example, by double immunodiffusion in agar against known concentrations of the antigen. (See, for example, Ouchterlony, O. et al., Chap. 19 in: *Handbook of Experimental Immunology* D. Wier (ed) Blackwell (1973)). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples. These antibody preparations are also used semi-quantitatively or qualitatively (e.g., in diagnostic embodiments that identify the presence of Aap in biological samples). It is also contemplated that various methods of molecular modeling and rational drug design can be applied to identify compounds that resemble Aap, AatP, AatA, AatB, AatC, AatD, fragments, or derivatives thereof, and molecules that interact with Aap, AatP, AatA, AatB, AatC, and/or AatD, and, thereby modulate the particular protein's function.

Non-therapeutic uses of antibodies to Aap or Aat proteins would include detection of the bacteria. Monoclonal or polyclonal antibodies could be used in slide agglutination assays to rapidly detect the bacteria. *E. coli* from a stool would be passaged onto nutrient agar and cultivated overnight at 37° C. Colonies would then be picked with a toothpick and resuspended in one drop of phosphate buffered saline on a glass microscope slide. One drop of antibody suspension would then be added to the bacterial suspension, mixed and rocked for one minute. At this time, the suspension would be examined for agglutination of the bacteria. Agglutination would be indicative of a positive interaction of antibodies and bacteria and would indicate that the bacteria expressed Aap or Aat proteins. As a modification of this technique, the antibodies could be affixed to latex beads to improve visualization.

Expression Vectors

Recombinant gene expression vectors containing any of the genes of this invention, or portions thereof, can be constructed in a variety of forms well-known in the art. Preferred expression vectors include plasmids and cosmids. Expression vectors include one or more fragments of a particular gene and preferably comprise the full length gene. An expression vector containing one or more of the genes of this invention can be used to transfect or transform a suitable host cell (prokaryotic or eukaryotic) to produce the protein or to produce an immune response, or for some other purpose.

As used herein, the phrase "operatively encode" refers to one or more protein coding regions associated with those regulatory sequences required for expression of the polypeptide encoded by the coding region. Examples of such regulatory regions include promoter binding sites, enhancer elements, ribosome binding sites, and the like. Those of ordinary skill in the art will be able to select regulatory sequences and incorporate them into the recombinant expression vectors described herein without undue experimentation. For example, suitable regulatory sequences for use in various eukaryotic and prokaryotic systems are described in Ausubel, et al., *Short Protocols in Molecular Biology*, $3^{rd}$ ed., John Wiley & Sons, Inc, New York, 1997, which is hereby incorporated by reference in its entirety.

Expression vectors for use with the aap gene or the aat gene cluster typically contain regulatory sequences derived from a compatible species for expression in the desired host cell. For example, when *E. coli* is the host cell, the host cell population is typically transformed using pBR322, a plasmid derived from an *E. coli* species that contains genes for ampicillin (AMPR) and tetracycline resistance. (Bolivar, et al., *Gene* 2:95 (1977)). Thus, pBR322 provides an easy means for identifying transformed cells. The plasmids described in Galen, WO 00/32047 are also useful for expression vectors in some bacteria.

Promoters suitable for use with prokaryotic hosts illustratively include the beta-lactamase and lactose promoter systems (Chang, et al., *Nature* 275:617 (1978); Goeddel, et al., *Nature* 281:544 (1979)), alkaline phosphatase, the tryptophan (trp) promoter system (Goeddel, *Nucleic Acids Res.* 8:4057 (1980)), ompC, nirB, and hybrid promoters such as the taq promoter (de Boer, et al., *Proc. Natl. Acad. Sci. USA* 80:21-25 (1983)). Other functional bacterial promoters are also suitable, and would be easily identifiable by those of skill in the art. The nucleotide sequences of these functional bacterial promoters are also generally known in the art, thereby enabling a skilled worker to ligate them to a polynucleotide encoding the peptide of interest (Siebenlist, et al., *Cell* 20:269 (1980)) using linkers or adapters to supply any required restriction sites.

Eukaryotic microbes such as yeast cultures can also be used as sources for the regulatory sequences. For example, *Saccharomyces cerevisiae* is a commonly used eukaryotic host microorganism. Suitable promoting sequences for use with yeast hosts include the promoters for 3-phosphoglycerate kinase (Hitzeman, et al., *J. Biol. Chem.* 255:12073 (1980)) or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase (Hess, et al. *J. Adv. Enzyme Reg.* 7:149 (1968); Holland, Biochemistry 17:4900 (1978)).

Other yeast promoters, which are inducible promoters having the advantage of transcription controlled by growth conditions, include the promoter regions for alcohol dehydrogenase 2, isocytochrome C, acid phosphatase, degraded enzymes associated with nitrogen metabolism, metallothionine, glyceraldehyde-3-phosphate dehydrogenase, and enzymes responsible for maltose and galactose utilization. Yeast enhancers are advantageously used with yeast promoters.

A recombinant virus can also be used as the expression vector. Exemplary viruses include the adenoviruses, adeno-associated viruses, herpes viruses, vaccinia, CMV, BLUE-SCRIPT (Stratagene, San Diego, Calif.), baculovirus, or an RNA virus such as a retrovirus or an alphavirus. Preferably, the retroviral vector is a derivative of a murine or avian retrovirus. The alphavirus vector is preferably derived from Sindbis or Semliki Forest Virus. All of these expression vectors can transfer or incorporate a gene for a selectable marker so that transduced cells can be identified and generated.

The viral vector can be made target specific by inserting one or more sequences of interest into the viral vector, along with another gene which encodes the ligand for a receptor on a specific target cell. For example, retroviral vectors can be made target specific by inserting a polynucleotide encoding a sugar, a glycolipid, or a protein. Preferred targeting is accomplished by using an antibody to target the retroviral vector, such as to the vicinity of a mucosal inductor site, using a MALT-specific antibody. Those of skill in the art will know of, or can readily ascertain without undue experimentation, specific polynucleotide sequences which can be inserted into the retroviral genome to allow target specific delivery of the retroviral vector containing the polynucleotides of interest.

In some instances, it can be preferable to use a selectable marker to identify cells or organisms that contain the expression vector and the DNA of interest. Selectable markers are generally introduced into the cells or organisms along with the cloned DNA molecules and include genes that confer resistance to drugs such as ampicillin, neomycin, hygromycin, and methotrexate. Selectable markers can also complement auxotrophies in the host cell, or can provide for detectable signals, such as beta-galactosidase, green fluorescent protein, or yellow fluorescent protein, to identify cells or organisms containing the cloned DNA molecules.

It will be appreciated that the same techniques that are utilized to incorporate the nucleotide sequences of aap and/or the aat gene cluster, and optionally other immunostimulatory polynucleotides, into viral gene expression vectors can be used to incorporate the sequences into live and attenuated live viruses for use as immunogenic compositions.

Targeting of mucosal tissues can be performed by exploiting inherent biological properties of the lymphoid bed which is to be targeted. These properties include the crypt architecture of the tonsillar pillars which can be used to entrap particles and also include the M cells of Peyer's patches in the gut which specifically endocytose a wide variety of particles including lipid particles and other small particulates. Therefore, those skilled in the art can prepare a wide variety of molecular particulate preparations which, if provided to the intestine, will lodge within the crypt portions of intestinal Peyer's patches and be endocytosed by M cells. If such particles provide for delivery of a biologically active polynucleotide to M cells, the particles will enable the stimulation or modulation of a mucosal immune response induction by the Peyer's patch lymphoid tissue to which the M cell traffics.

Construction of suitable expression vectors containing desired coding, non-coding, and control sequences employ standard ligation techniques. Isolated plasmids or DNA fragments are cleaved, tailored, and re-ligated in the form desired to construct the required plasmids. To confirm correct sequences in the plasmids constructed, the ligation mixtures can be used, for example, to transform a host cell and successful transformants selected by antibiotic resistance where appropriate. Plasmids from the transformants are prepared, analyzed by restriction and/or sequenced by, for example, by the method disclosed in Messing, et al. (*Nucleic Acids Res.*, 9:309 (1981)), Maxam, et al. (*Methods in Enzymology* 65:499 (1980)), or other suitable methods which will be known to those skilled in the art. Size separation of cleaved fragments can be performed using conventional gel electrophoresis as described, for example, by Maniatis, et al. (Molecular Cloning, pp. 133-134 (1982)).

Host cells can be transformed with the expression vectors described herein and cultured in conventional nutrient media modified as is appropriate for inducing promoters, selecting transformants, or amplifying genes. The culture conditions, such as temperature, pH and the like, are those previously used with the host cell selected for expression, and will be apparent to the ordinarily skilled artisan.

Purification

Steps involved in the purification of one or more of the proteins of this invention include (1) solubilization of the desired protein, (2) the development of one or more isolation and concentration procedures, (3) stabilization of the protein following purification, and (4) development of a suitable assay to determine the presence of the desired protein. Various aspects of protein isolation and purification are discussed in detail in Cooper, T. G., "The Tools of Biochemistry," John Wiley & Sons, New York, 1977, which is hereby incorporated by reference in its entirety. As the techniques of protein isolation and purification are notoriously well known in the art, this disclosure will refrain from discussing them in detail. Nevertheless, elements of the cited reference are summarized and discussed below.

Solubilization is required of most proteins that are to be purified, as most isolation procedures commonly used operate in aqueous solutions. In some cases, solubilization can be achieved by merely lysing a host cell within which a desired protein has been expressed. In other situations, additional steps, such as extracting the desired protein from a subcellular organelle, may be required. Osmotic lysis, grinding, the use of blenders, ultrasonic waves, presses, and other well known techniques of protein solubilization can be used with the methods disclosed herein.

There are a variety of techniques available that are well known in the art for the isolation and concentration of the proteins of this invention. These techniques include, but are not limited to, (1) differential solubility, (2) ion exchange chromatography, (3) absorption chromatography, (4) molecular sieve techniques, (5) affinity chromatography, (6) electrophoresis, and (7) electrofocusing. Each of these techniques can also be useful in the purification of a protein of this invention. An example of the purification of Aap can be found below.

Stabilizing and maintaining a purified protein product in a functional state warrants attention to a number of different conditions such as (1) pH, (2) degree of oxidation, (3) heavy metal concentration, (4) medium polarity, (5) protease concentration, and (6) temperature. One of ordinary skill in the art would readily know which of the available techniques to use to maintain purified protein in an active form without undue experimentation.

Compositions

The proteins encoded by aap and the aat gene cluster can be used to formulate immunogenic compositions that facilitate an immune response. Examples of a typical immune response to EAEC infections include a mucosal immune response and a systemic immune response.

In accordance with one aspect of the present invention, smaller fragments of the proteins of this invention are used to provide an immunogenic composition. Specifically, these fragments comprise an immunogenic region of expression products, typically from about 5, 6, 8, 10 or 12 amino acids to about 20, 22, 24, 30, or more amino acids. Suitable fragments or immunogenic regions can be readily ascertained using the techniques set forth below as screening procedures. In one example of a suitable screening procedure, a large number of candidate fragments are more or less randomly produced and used to immunize guinea pigs or other suitable models. Alternatively, full-length polypeptides shown to be active in the present invention can be truncated and screened in an iterative process to isolate the immunogenic and protective activity to a minimal fragment. Such screening can be readily carried out without undue experimentation and the active fragments are within the contemplation of the present invention. A third example would be to predict surface-exposed and immunogenic epitopes using hydrophobicity and/or other amino acid properties. Predicted surface-exposed residues would be synthesized as oligopeptides and antibodies would be raised against these peptides, e.g., in a rabbit or mouse. The antibodies would then be tested for reaction against the intact protein. Binding to the protein would suggest that the predicted epitopes are indeed surface-exposed and could therefore represent potentially protective epitopes for an EAEC vaccine.

Recombinant Organisms

In one embodiment of the present invention, a nucleotide sequence comprising the aap gene or a functional fragment thereof or one or more of the genes or fragments thereof of the aat gene cluster is introduced into an exogenous organism using standard molecular biology techniques well known to those of ordinary skill in the art. Exemplary molecular biology techniques are discussed in Ausubel, et al., "Short Protocols in Molecular Biology." The resulting recombinant organism can then be used as an immunogen against which an immune response may be engendered. In a preferred embodiment, an attenuated pathogenic organism serves as the exogenous organism. In addition, it is contemplated that an entire recombinant organism or a functional fragment thereof, such as an isolated membrane fraction, liposome, or the like, can be used to generate an immunogenic composition. One this contemplated embodiment, the aap gene would be co-expressed with the usher and chaperone from the parent organism, EAEC 042, to ensure secretion of the Aap protein through the bacterial outer membrane. The usher (aafC) and chaperone genes (aajD) are available as chimeric clones. In another embodiment, the entire aat gene cluster would be expressed within an organism.

Subunit Immunogenic Compositions

Another embodiment of the present invention relates to the generation of immunogenic compositions comprising distinct immunogenic proteins (or fragments thereof) or functional fragments of the organisms of interest. Such immunogenic compositions are referred to herein as subunit immunogenic compositions because at least one of the components of the composition is a subunit of an organism, rather than an entire organism. Typically, such a subunit immunogenic composition comprises one or more immunogenic components.

In a preferred embodiment, the subunit immunogenic composition includes a carrier component and an immunogenic component. Typically, the carrier component functions as a binding moiety with which the originating organism uses to bind to and gain entrance into the host organism. In another preferred embodiment, Aap, AatP, AatA, AatB, AatC, and/or AatD from EAEC functions as the carrier component. Any protein, peptide, or amino acid sequence that elicits an immune response can be used as the immunogenic component in a subunit immunogenic composition.

The carrier component of the subunit immunogenic composition can possess immunogenic characteristics themselves. Typically, adjuvants are used in immunogenic compositions to enhance the immune response directed against the immunogenic component of the immunogenic compositions. Carrier components that possess both mucosa binding characteristics and immunogenic characteristics can be used. For example, Aap, AatP, AatA, AatB, AatC, and/or AatD can function both as the carrier component and the immunogenic component.

For the carrier components described above, the entire molecule can be used as the carrier component, or a functionally active fragment of the molecule can be used. Mutagenized forms of these molecules can also be used as carrier components.

Although not wishing to be bound by theory, it is hypothesized that the subunit immunogenic composition functions by exposing the immunogenic component of the subunit immunogenic composition to the mucosa and the various immune system components present there. According to one theory, the generation of a desired immune response by the subunit immunogenic composition occurs by increasing the exposure of the immunogenic composition to the target tissue. The presence of both a carrier component and an immunogenic component are theorized to achieve this goal.

In one embodiment of the instant invention, Aap is isolated, purified, and mixed or coupled with one or more immunogenic or adjuvant compounds. For example, Aap can be expressed, purified, and cross-linked to a toxin, toxoid (an attenuated toxin), or some other immunogenic compound for use in a subunit immunogenic composition. In another embodiment, AatA can be expressed, purified, and cross-linked to a toxin, toxoid (an attenuated toxin), or some other immunogenic compound for use in a subunit immunogenic composition.

In another embodiment, expressed Aap or fragments thereof or AatA or fragments thereof can be cross-linked to an immunogenic component, which can be an isolated protein, a functional fragment thereof, a whole organism (such as a bacterium or a virus) or functional fragment thereof that is isolated either in part or is used as a whole pathogenic organism. Aap and AatA can be isolated from the bacterium itself or it can be produced using recombinant DNA techniques well known in the art. It is contemplated, and within the purview of the present invention, that an entire recombinant organism or a functional fragment thereof, such as an isolated membrane fraction, liposome, or the like, can be used to generate an immunogenic composition.

The proteins of this invention which are used to form the subunit immunogenic compositions can be the whole protein, an immunogenic fragment thereof, a mutagenized form of the protein, or a fusion protein comprising the particular protein or a fragment thereof and a suitable fusion partner (e.g., any protein, peptide or amino acid sequence that facilitates the expression and/or purification of the protein and fusion partner using recombinant DNA techniques known in the art). Alternatively, one or more additional immunogens can serve as the fusion partner in a fusion protein.

Nucleotide Immunogenic Compositions

An immune response can also be elicited using nucleotide-containing compositions. For example, in one embodiment encompassed by the present invention, a mucosal or systemic immune response is elicited in a host by administering an antigen-encoding polynucleotide preparation including DNA or RNA that encodes an antigenic epitope to the host. Preferably, the nucleotide-containing composition is administered to a mucosal inductor site in the mucosal tissue of the host. Naked DNA may be administered directly to the mucosa (e.g., in saline drops) or in a recombinant gene expression vector. Preferably, the recombinant gene expression vector is not capable of replication or dissemination.

Nucleotide-containing immunogenic compositions also include live viral immunogenic compositions. The viruses for use in the viral immunogenic compositions include immuno-stimulatory polynucleotides. Preferably, a target protein antigen is administered through its expression by a recombinant gene expression vector.

U.S. Pat. No. 6,110,898, to Malone, et al., entitled, "DNA vaccines for eliciting a mucosal immune response," which is hereby incorporated by reference in its entirety, provides detailed teaching for the generation of such immunogenic compositions. In particular, Malone teaches obtaining a recombinant alphavirus vector system as described in Malone, J. G., et al., "Mucosal immune responses associated with polynucleotide vaccination", *Behring Inst Mitt* 98:63-72 (1997 February). DNA encoding Aap (for example) is substituted for the lacZ gene in the vector. The replication defective alphavirus particles are activated by combining one volume of virus stock to 1/20 volume of Chymotrypsin 10 mg/ml (in PBS with $Ca^{2+}/Mg^{2+}$) and 1/50 volume of $CaCl_2$ (50 mM). This mixture is allowed to incubate at room temperature for thirty minutes and then put on ice. Next, a ½ volume of Aprotinin 2 mg/ml is added. The solution is kept on ice for up to one hour and discarded if not used.

Balb-C mice (SPF female, 6 week, Charles River) are inoculated with $10^6$ virion particles ($10^7$/ml) via either intratracheal, intranasal, or intravenous routes. Animals are anesthetized with a cocktail of ketamine (22 mg/kg), xylazine (2.5 mg/kg) and acepromazine (0.75 mg/kg) prior to inoculation. Intratracheal inoculation is performed by making a small medial cut through the skin at the ventral site of the neck. Salivary glands are teased apart using blunt dissection to expose the trachea. With the trachea visualized, a 30.5 gauge needle with a 1 cc tuberculin syringe attached is placed through the rings of the trachea toward the bronchi. 100 µl of the above virion particles are injected into the lung. Intranasal installation consists of placing 50 µl of the virion particles into one of the nares. Once this is taken into the nasal passages by inhalation, the other side is inoculated in the same manner. Intravenous inoculation is performed using a 30.5 gauge needle with 100 µl of the above virion particles inserted into the tail vein.

Blood is collected from the retro-orbital venous plexus at day 0, 14, and 28, using a microcapillary tube. The blood is allowed to sit at room temperature for 2-4 hours to clot, then it is spun in a IEC Centra MP4R centrifuge at 6,000 RPM for six minutes. The supernatant (serum) is removed and stored at −20° C. until ELISA assays are performed.

Lung lavages at week 4 are performed by the following method. Mice are killed by carbon dioxide asphyxiation. The ventrum is skinned and the mesentery removed which exposes the liver. The liver is moved aside to visualize the diaphragm. The diaphragm is opened and the rib cage is cut bi-laterally up through the sternum. This section is lifted up over the mouse's head, leaving the trachea exposed. A transverse cut of the trachea is made approximately 2 cm above the bronchus. A blunt 24 gauge needle is inserted 0.5 cm into the trachea and tied in place with surgical thread. One ml of BBS (89 mM boric acid, 90 mM NaCl, pH 8.3 [NaOH]) is slowly introduced into the lungs using a 1 ml tuberculin syringe attached to the blunt needle and then the volume is slowly withdrawn. The solution is centrifuged to produce a cellular (particulate) and a supernatant component. Recovered volumes are normally in the range of 0.85 to 0.95 ml. This cellular and supernatant components are stored at −20° C. until used.

Animals for which histological sections are to be taken are killed by carbon dioxide on day two. Their lungs are fixed in paraformaldehyde for thirty minutes, the tissue is then incubated overnight at 4° C. in a mix of PBS+2 mM $MgCl_2$+30% sucrose. Lung tissue are cryosectioned and placed on gelatinized slides. The slides are then fixed and stained for Aap using an biotinylated labeled anti-Aap antibody.

ELISA assays are performed on samples using 96 well microtiter plates using the same basic protocol as described in by Engvall, E., *Meth. Enzymol.* 70:419 (1980), and derivative methods thereof. In brief, Aap is suspended to a concentration of 1 mg/ml with PBS supplemented with 5 mg/ml bovine serum albumin. The wells of the microtiter plate are coated with 5 mg of Aap (in that solution) per ml BBS (89 mM boric acid, 90 mM NaCl, pH 8.3 [NaOH]). The plates are incubated overnight at 4° C. The plates are dried by pounding on a stack of paper towels and blocked with 150 µl BB (BBS as above with 1% bovine serum albumin added). After the plates sit at room temperature for 2 hours, eight two-fold dilutions of sample sera in BB are pipetted into the microtiter plates (50 µl per well). Dilutions are performed as follows: serum IgG and IgA—1:10 to 1:5120, lavage IgG and IgA—1:1 to 1:128. The plates are incubated overnight at 4° C. Plates are washed 5-6 time with BBS plus 0.05% Tween and dried. Either alkaline phosphatase conjugated goat anti-mouse IgG at 1:2000 dilution or goat anti-mouse IgA at 1:1000 dilution in BB are added (50 µl per well). Plates are incubated for two hours at room temperature. They are washed and dried as described above and the substrate buffer (1 mg/ml p-nitrophenol phosphate, 50 mM Na-bicarbonate buffer, pH 9.8, 1 mM $MgCl_2$) is added. Plates are incubated again at room temperature for one hour. A Dynatech MR5000 ELISA plate reader with a 405 nm wavelength (Dynatech Laboratories, Chantilly, Va.) hooked up to a iMac (having the appropriate software) reads the plates. Background signal is defined using control serum, with positive titer identified at >2.5× background. For lavage samples, $OD_{405}$ is reported using the 1:2 dilution, with positive signal defined as 2.5× background.

The results of the lung lavage studies demonstrate that intranasal inoculation results in high levels of both IgG and IgA (indicative of mucosal immunity). Intratracheal and intravascular inoculations produce a systemic immune response.

Alternatively, one or more of the genes of the aat cluster can be introduced to an attenuated EAEC, *Salmonella* spp., *Shigella* spp., *Lactobacillus* spp., or other attenuated bacteria which is invasive for mucosal tissue, which then expresses the particular Aat protein encoded by the gene. The bacteria is administered to an animal to generate an immune response to the particular Aat protein encoded.

Formulations and Administration

The immunogenic compositions described herein can be formulated in a variety of useful formats for administration by a variety of routes. Concentrations of the immunogenic components in the formulations described will be such that an effective dose of the immunogenic components is included in the formulation. Determination of such a concentration would be readily apparent to those of ordinary skill in the art.

Administration of the immunogenic compositions can be by nasal application, by inhalation, ophthalmically, orally, rectally, vaginally, or by any other mode that results in the immunogenic composition contacting mucosal tissues.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, micro-crystalline cellulose, cornstarch, sodium starch glycolate, and alginic acid. Tablet binders that may be used include acacia, methylcellulose, sodium carboxymethylcellulose, polyvinylpyrrolidone, hydroxypropyl methylcellulose, sucrose, starch, and ethylcellulose. Lubricants that may be used include magnesium stearates, stearic acid, ailicone fluid, talc, waxes, oil, and colloidal silica.

In one embodiment of the present invention, the immunogenic composition exists as an atomized dispersion for delivery by inhalation. The atomized dispersion of the immunogenic components typically contains carriers common for atomized or aerosolized dispersions, such as buffered saline and/or other compounds well known to those of skill in the art. The delivery of the immunogenic compositions via inhalation has the effect of rapidly dispersing the immunogenic components to a large area of mucosal tissues as well as quick absorption by the blood for circulation of the immunogenic components. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

The immunogenic compositions described herein can also be formulated in the form of a rectal or vaginal suppository. Typical carriers used in the formulation of the inactive portion of the suppository include polyethylene glycol, glycerine, cocoa butter, and/or other compounds well known to those of skill in the art. Although not wishing to be bound by theory, delivery of immunogenic compositions via a suppository is hypothesized to have the effect of contacting a mucosal surface with the immunogenic compositions for release to proximal mucosal tissues. Distal mucosal tissues also receive the immunogenic composition by diffusion. Other suppository formulations suitable for delivery of the immunogenic compositions encompassed by the present invention are also contemplated.

Additionally, immunogenic compositions also exist in a liquid form. The liquid can be for oral dosage, for ophthalmic or nasal dosage as drops, or for use as an enema or douche. When the immunogenic composition is formulated as a liquid, the liquid can be either a solution or a suspension of the immunogenic composition. There are a variety of suitable formulations for the solution or suspension of the immunogenic composition that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Delivery of the described immunogenic compositions in liquid form via oral dosage exposes the mucosa of the gastrointestinal and urogenital tracts to the immunogenic compositions. A suitable dose, stabilized to resist the pH extremes of the stomach, delivers the immunogenic compositions to all parts of the gastrointestinal tract, especially the upper portions thereof. Any method of stabilizing the immunogenic compositions in a liquid oral dosage such that the effective delivery of the composition is distributed along the gastrointestinal tract are contemplated for use with the immunogenic compositions described herein.

Delivery of the described immunogenic compositions in liquid form via ophthalmic drops exposes the mucosa of the eyes and associated tissues to the immunogenic compositions. A typical liquid carrier for eye drops is buffered and contains other compounds well known and easily identifiable to those of skill in the art.

Delivery of the described immunogenic compositions in liquid form via nasal drops exposes the mucosa of the nose and sinuses and associated tissues to the immunogenic compositions. Liquid carriers for nasal drops are typically various forms of buffered saline.

A colloidal dispersion system may be used for targeted delivery of nucleic acid-containing immunogenic compositions. Colloidal dispersion systems include macromolecule complexes, nanocapsules, microspheres, beads, and lipid-based systems including oil-in-water emulsions, micelles, mixed micelles, and liposomes. A preferred colloidal system is a lipid preparation including unilamaller and multilamellar liposomes.

Injectable formulations of the compositions may contain various carriers such as vegetable oils, dimethylacetamide, dimethylformaamide, ethyl lactate, ethyl carbonate, isopropyl myristate, ethanol, polyols (glycerol, propylene glycol, and liquid polyethylene glycol) and the like. For intravenous injections, water soluble versions of the compounds may be administered by the drip method, whereby a pharmaceutical formulation containing an antifungal agent and a physiologically acceptable excipient is infused. Physiologically acceptable excipients may include, for example, 5% dextrose, 0.9% saline, Ringer's solution or other suitable excipients. Intramuscular preparations (e.g., a sterile formulation of a suitable soluble salt form of the composition) can be dissolved and administered in a pharmaceutical excipient such as Water-for-Injection, 0.9% saline, or 5% glucose solution. A suitable insoluble form of the composition may be prepared and administered as a suspension in an aqueous base or a pharmaceutically acceptable oil base, such as an ester of a long chain fatty acid (e.g., ethyl oleate).

Liposomes are artificial membrane vesicles that are useful as delivery vehicles in vitro and in vivo. It has been shown that large unilamellar vesicles (LUV), which range in size from 0.2-4.0 μm, can encapsulate a substantial percentage of an aqueous buffer containing large macromolecules. RNA, DNA, and intact virions can be encapsulated within the aqueous interior and can be delivered to cells in a biologically active form (Fraley, et al., *Trends Biochem. Sci.* 6:77 (1981)). In addition to mammalian cells, liposomes have been used for delivery of polynucleotides in plant, yeast, and bacterial cells. In order for a liposome to be an efficient gene transfer vehicle, the following characteristics should be present: (1) encapsulation of the genes encoding the polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information. (Mannino, et al., *Biotechniques* 6:682 (1988)). In addition to such LUV structures, multilamellar and small unilamellar lipid preparations that incorporate various cationic lipid amphiphiles can also be mixed with anionic polynucleotides to form nucleolipidic particles which are often also referred to as liposomes. (Felgner, et al., *Proc Natl. Acad. Sci.* U.S.A. 84 (21): 7413 (1987)). These nucleophilic particles can be used to deliver the nucleic acids into cells.

The composition of the liposome is usually a combination of phospholipids, preferably high-phase-transition-temperature phospholipids, usually in combination with steroids, preferably cholesterol. However, other phospholipids or other lipids may also be used. The physical characteristics of the liposomes depend on pH, ionic strength, and the presence of divalent cations. The appropriate composition and preparation of cationic lipid amphiphile:polynucleotide formulations are known to those skilled in the art, and a number of references which provide this information are available (e.g., Bennett, et al, *J. Liposome Res.* 6(3):545).

Examples of lipids useful in liposome production include, but are not limited to phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, preferably from 16-18 carbon atoms, and is saturated. Illustrative phospholipids include egg phosphatidylcholine, dipalmitoylphosphatidylcholine, and distearoylphosphatidylcholine. Examples of cationic amphiphilic lipids useful in formulation of nucleolipid particles for polynucleotide delivery include the monovalent lipids DOTAP, DOTMA, and DC-Chol, the polyvalent lipids LipofectAMINE, DOGS, Transfectam, and other amphiphilic polyamines. These agents may be prepared with helper lipids (such as Dioleoyl Phosphatidyl Ethanolamine) or with various carrier compositions, including various adjuvants such as cholera-derived molecules including cholera toxin.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs that contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used to join the lipid chains to the targeting ligand.

Administration of the compounds discussed above can be practiced in vitro or in vivo. When practiced in vitro, any sterile, non-toxic route of administration may be used. When practiced in vivo, administration of the compounds discussed above may be achieved advantageously by subcutaneous, intravenous, intramuscular, intraocular, oral, transmucosal, or transdermal routes, such as, for example, by injection or by means of a controlled release mechanism. Examples of controlled release mechanisms include polymers, gels, microspheres, liposomes, tablets, capsules, suppositories, pumps, syringes, ocular inserts, transdermal formulations, lotions, creams, transnasal sprays, hydrophilic gums, microcapsules, inhalants, and colloidal drug delivery systems.

The immunogenic compositions are administered in a pharmaceutically acceptable form and in substantially non-toxic quantities. In particular, the immunogenic compositions can be administered in amounts appropriate to those individual compounds to produce an immune response. Appropriate doses can readily be determined by techniques well known to those of ordinary skill in the art without undue experimentation. Such a determination will be based, in part, on the tolerability and efficacy of a particular dose using techniques similar to those used to determine proper chemotherapeutic doses. Additionally, the compounds may be administered in water with or without a surfactant.

Injectable preparations include sterile aqueous solutions or dispersions and powders, which may be diluted or suspended in a sterile environment prior to use. Carriers such as solvents or dispersion media containing water, ethanol polyols, vegetable oils and the like may also be added to the compositions described herein. Coatings such as lecithins and surfactants may be used to maintain the proper fluidity of the composition. Isotonic agents such as sugars or sodium chloride may be added, as well as products intended to delay absorption of the active compounds, such as aluminum monostearate and gelatin. Sterile injectable solutions are prepared according to methods well known to those of skill in the art and can be filtered prior to storage and/or use. Sterile powders may be vacuum or freeze dried from a solution or suspension. Sustained-release preparations and formulations are also contemplated. Any material used in the compositions described herein should be pharmaceutically acceptable and substantially non-toxic in the amounts employed. Antimicrobial compounds may optionally be added to the preparations.

Although in some of the experiments that follow the compounds are administered in a single dose, it should be understood that in a clinical setting, the compounds may be administered in multiple doses over prolonged periods of time. In particular, the compounds may be administered for periods up to about one week, and even for extended periods longer than one month or one year. In some instances, administration of the compounds may be discontinued and resumed at a later time.

All compound preparations may be provided in dosage unit forms for uniform dosage and ease of administration. Each dosage unit form contains a predetermined quantity of active ingredient calculated to produce a desired effect in association with a pharmaceutically acceptable carrier. Such a dosage would therefore define an effective amount of a particular compound.

A kit comprising the necessary components of an immunogenic composition that elicits an immune response to a selected immunogenic component are also within the purview of the present invention.

Diagnosis

The invention also provides for a method of detecting Aap, AatP, AatA, AatB, AatC, and/or AatD in a sample which includes contacting a sample from a subject with an antibody to one or more of these proteins and detecting binding of the antibody to the specific protein for which the antibody recognizes. Antibody binding is indicative of the presence of the specific protein in the sample. In one embodiment of the instant invention, the presence of Aap, AatP, AatA, AatB, AatC, and/or AatD in the sample is indicative of infection by EAEC. Since Aap and Aat are highly specific for EAEC, the detection of these proteins on bacteria in a clinical sample suggests that the patient is infected with EAEC bacteria.

The term "sample" includes material derived from an animal (e.g., fish, bird, mammal, human, etc.). Such samples include, but are not limited to, hair, skin, tissue, cultured cells, cultured cell media, and biological fluids. The term "tissue" refers to a mass of connected cells (e.g., CNS tissue, neural tissue, or eye tissue) derived from a human or other animal and includes the connecting material and the liquid material in association with the cells. As used herein, the term "biological fluid" refers to liquid material derived from a human or other animal. Such biological fluids include, but are not limited to, blood, plasma, urine, semen, excrement, serum, serum derivatives, bile, phlegm, saliva, sweat, amniotic fluid, pleural fluid, and cerebrospinal fluid (CSF), such as lumbar or ventricular CSF.

The term "sample" also includes solutions containing the isolated Aap, AatP, AatA, AatB, AatC, and/or AatD polypeptides, media into which these proteins has been secreted, and media containing host cells which produce these proteins. For example, a sample may be a protein sample which is to be resolved by SDS-PAGE and transferred to nitrocellulose for Western blot analysis. The quantity of sample required to obtain a reaction may be readily determined by one skilled in the art by standard laboratory techniques. The optimal quantity of a sample may be determined by serial dilution.

A kit for diagnosing or determining the presence of EAEC in an animal is an embodiment within the scope of this invention. In one embodiment of this invention, a kit contains one or more antibodies (e.g., that have been described above) that recognize Aap, AatP, AatA, AatB, AatC, and/or AatD or a fragment of one or more of these proteins. The kit is useful for the detection of Aap, AatP, AatA, AatB, AatC, and/or AatD and has a compartmentalized carrier capable of receiving in a close confinement a container containing an antibody which binds to Aap, AatP, AatA, AatB, AatC, and/or AatD. As used herein, "a container" includes vials, tubes, and the like, each of the containers containing one of the separate elements to be used. In a preferred embodiment, the antibody which binds to Aap, AatP, AatA, AatB, AatC, and/or AatD is detectably labeled. In an even more preferred embodiment, the label is a radioisotope, a bioluminescent compound, a chemiluminescent compound, a fluorescent compound, a metal chelate, or an enzyme. The kit may alternatively contain an antibody which recognizes an anti-Aap antibody, or anti-AatP antibody, or anti-AatA antibody, or anti-AatB antibody, or anti-AatC antibody, or anti-AatD antibody so that the kit can be used to determine if antibodies to one or more of these proteins are present in a sample or tissue.

In a kit format, the antibody would be commercially bound to latex beads. The beads would be mixed with a suspension of E. coli bacteria in saline. The suspension is rocked at room temperature for one minute and the presence of agglutination of the suspension is read as a positive test.

In yet another embodiment, the kit is useful for the detection of an aap polynucleotide and/or polynucleotides for one or more genes of the aat gene cluster. The kit is a compartmentalized carrier to receive in close confinement a container containing the nucleic acid probe that hybridizes to a polynucleotide for aap, and/or one or more genes of the all gene cluster. Preferably, the nucleic acid probe that hybridizes to the polynucleotide from the sample is detectably labeled. It is preferred that the label is a radioisotope, a bioluminescent compound, a chemiluminescent compound, a fluorescent compound, a metal chelate, or an enzyme.

Prevalence of the aat Cluster Among EAEC

Figure 4:
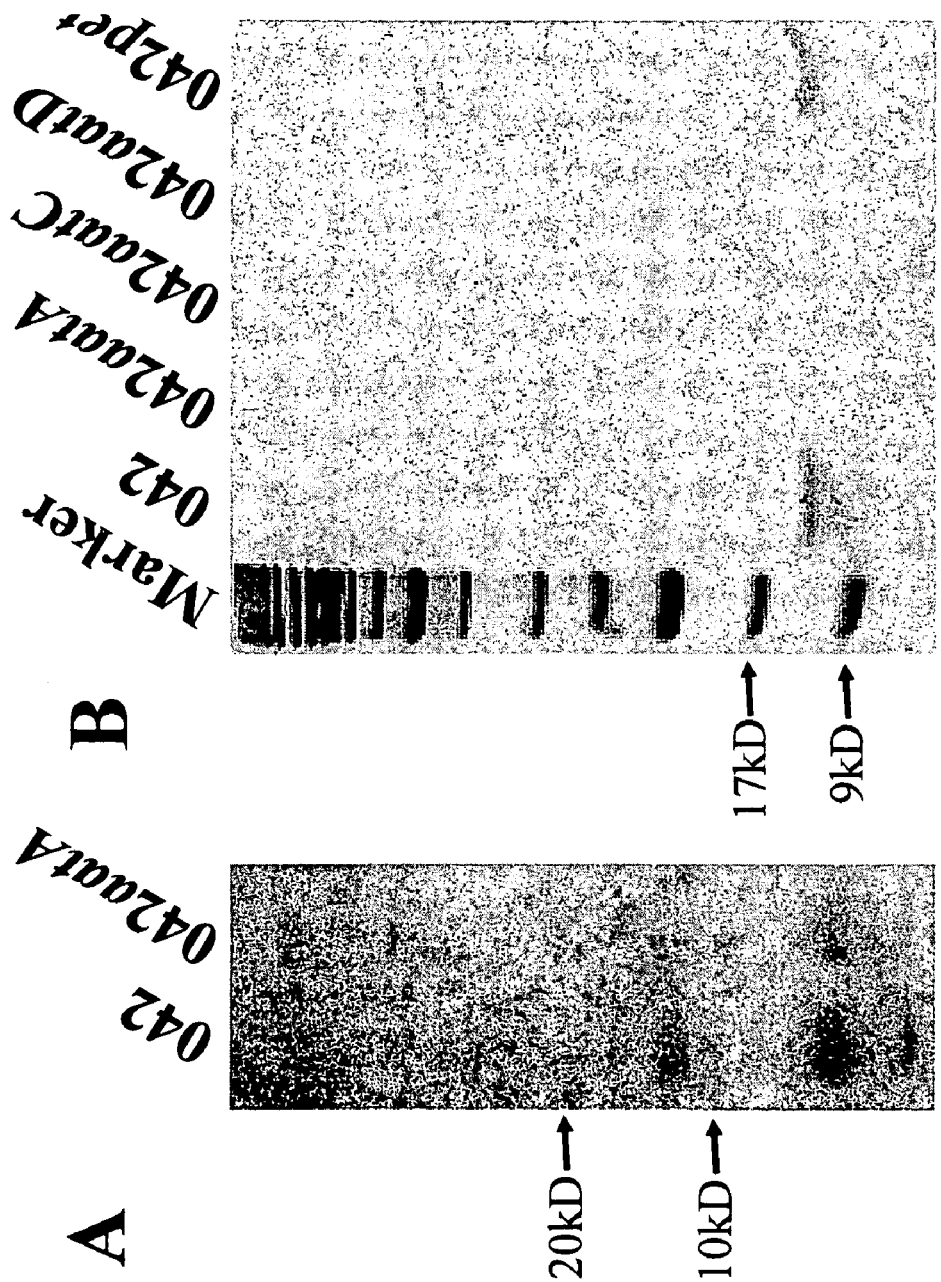
FIG. 4A is a photograph of the SDS-PAGE of culture media precipitated with trichloroacetic acid of wild type and mutant aat.
FIG. 4B is a photograph of the SDS-PAGE of the supernatant of the culture with 0.1% Triton X-100 of wild type and mutant aat.

The sequence of aatA is remarkably conserved between AAF/I-encoding strain 17-2 and AAF/II-encoding strain 042. They are 96% identical at the nucleotide level and 95% at the amino acid level. To assess the conservation of the aat cluster among clinical EAEC isolates, 31 strains isolated from children of several districts around the world for aatA and aatBCD (also referred to as aatB, aatC, aatD) are examined by PCR. FIG. 4 shows the representative PCR results. In addition, the presence of aggR is investigated by PCR to compare the prevalence of aat and aggR. The prevalence of aatA, aatBCD, and aggR in 31 EAEC isolates is shown below in Table 1 set forth below. The incidences of aatA and aatBCD are 71.0% (22/31) and 74.2% (23/31) respectively. It is noted that aatA is always accompanied by aatBCD, except in one strain. This observation suggests that the aat cluster is highly conserved among EAEC clinical isolates. Nineteen of twenty-two aat-positive strains are aggR-positive, while five of nine aat-negative strains are aggR-negative. The presence of aggR significantly correlates with that of the aat cluster ($p=0.016$).

TABLE 1

Prevalences of the aat cluster and aggR in EAEC isolates.

| No. | Strain | aatA | aatBCD | aggR |
|---|---|---|---|---|
| 1 | 042 (Peru) | + | + | + |
| 2 | 17-2 (Chile) | + | + | + |
| 3 | Brazil 236 | + | + | + |
| 4 | Mexico 60A | + | + | + |
| 5 | Peru 11145-1 | + | + | + |
| 6 | Peru 11194-2 | + | + | + |
| 7 | Peru 11232-1 | + | + | + |
| 8 | Peru 1132-1 | + | + | − |
| 9 | Peru 1146-2 | + | + | − |
| 10 | Peru 1177-1 | + | + | + |
| 11 | Peru 1192-1 | + | + | + |
| 12 | Peru 133 | + | + | + |
| 13 | Phil DS244-R3 | + | + | + |
| 14 | Phil DS61-R2 | + | + | − |
| 15 | Phil DS67-R2 | + | + | + |
| 16 | Thai 103-1-1 | + | + | + |
| 17 | Thai 144-1-1 | + | + | + |
| 18 | Thai 199-1-4 | + | + | + |
| 19 | Thai 253-1-1 | + | + | + |
| 20 | Thai 309-1-1 | + | + | + |
| 21 | Thai 44-1-1 | + | + | + |
| 22 | Thai 6-1-1 | + | + | + |
| 23 | Peru 11223-1 | − | + | + |
| 24 | Peru 1111-1 | − | − | + |
| 25 | Peru 11191-1 | − | − | + |
| 26 | Peru 1172-2 | − | − | − |
| 27 | Phil DS65-R3 | − | − | − |
| 28 | Thai 435-1-1 | − | − | − |
| 29 | Thai 501-1-1 | − | − | + |
| 30 | Japan 101-1 | − | − | − |
| 31 | Serbia | − | − | − |

The Transcription of the aat Cluster and its Dependency on AggR

Initially, aatA, aatC, and aatD mutants of strain 042 are constructed. Each gene is then inactivated by the integration of a suicide plasmid, pJP5603. Each transcript is observed in the wild type but not in the mutant (data not shown).

To assess the transcriptional linkage among the five genes, RT-PCR is performed using several combinations of primers to the genes in the aat cluster (shown in Table 2). The RT-PCR assay using the primer aatPint-F and aatAint-R yields a predicted size of product, but the assays using the combinations of primers derived from aatA, aatB, aatC, and aatD genes do not yield products (data not shown). These results suggest that the aatP and aatA genes are transcribed polycistronically. The data also indicates transcriptional linkage of the other genes in the aat cluster.

AatA antiserum. AatA-specific antibodies are concentrated by affinity purification against the purified protein (see below). Western immunoblots are then prepared from whole cell, periplasm, and outer membrane. A band of the expected size is observed in whole cell lysates of 042 cultured in Dulbecco's minimum essential medium (DMEM) supplemented with 0.45% glucose (high-glucose DMEM) but not in 042aatA. (Data not shown). The same size of band is observed in the outer membrane, but not in the periplasm fraction. AatA is not observed in the culture media (data not shown). Thus, AatA exists mainly on the outer membrane. To determine whether AatA is translocated to the outer membrane using the energy generated by the ABC transporter junction of AatC, 042aatC and 042aatD are examined for AatA by Western immunoblot. AatA is observed in the outer membranes of both 042aatC and 042aatD (data not shown).

TABLE 2

Sequences of primers

| NAME | GENE | SITE | SEQUENCE (5' to 3') | RE | SEQ ID NO: |
|---|---|---|---|---|---|
| CR | | | | | |
| aatA-F | aatA | 2723-2744 | acggatccatgttaccagatataaatatag | BamHI | SEQ ID NO: 18 |
| aatA-R | aatA | 3766-3787 | acgaattccatttccctgtattggaaatg | EcoRI | SEQ ID NO: 19 |
| aatAint-F | aatA | 2893-2910 | actctagatgaaatgcttagtgagag | XbaI | SEQ ID NO: 20 |
| aatAint-R | aatA | 3395-3412 | acgaattcgatacccagactagcact | EcoRI | SEQ ID NO: 21 |
| aatCint-F | aatC | 4610-4630 | actctagaagttggaaagacttcactgc | XbaI | SEQ ID NO: 22 |
| aatCint-R | aatC | 4889-4909 | acgaattccggagagaaatgatacatta | EcoRI | SEQ ID NO: 23 |
| aatDint-F | aatD | 5361-5380 | actctagaagttcttatgggttacttgg | XbaI | SEQ ID NO: 24 |
| aatDint-R | aatD | 5841-5860 | acgaattcatcccatatttgtagtggag | EcoRI | SEQ ID NO: 25 |
| aatW-F | aat cluster | 001-022 | acggatccggagacgtttggaggtgtatggg | BamHI | SEQ ID NO: 26 |
| aatW-R | aat cluster | 6446-6465 | acgcggccgctagcgttattgttcaacgcc | NotI | SEQ ID NO: 27 |
| aat-PA-R | aatP and aatA | 3864-3886 | acgcggccgcacattaccttcaatcatgtcctc | NotI | SEQ ID NO: 28 |
| RT-PCR | | | | | |
| CAT-f | cat | | tcactggatataccaccgtt | | SEQ ID NO: 29 |
| CAT-R | cat | | ccactcatcgcagtactgtt | | SEQ ID NO: 30 |
| aatA-F | aatA | 2723-2744 | atgttaccagatataaatatag | | SEQ ID NO: 31 |
| aatA-R | aatA | 3766-3787 | catttccctgtattggaaatg | | SEQ ID NO: 32 |
| aatB-F | aatB | 3687-3709 | atgaaacagaaaatgaatttcag | | SEQ ID NO: 33 |
| aatB-R | aatB | 4483-4508 | ctaatcatctattataatctcaaacg | | SEQ ID NO: 34 |
| aatC-F | aatC | 4501-4523 | atgattagagtaaaaatacataa | | SEQ ID NO: 35 |
| aatC-R | aatC | 5108-5130 | ctatgtatttaatagttggatta | | SEQ ID NO: 36 |
| aatD-F | aatD | 5142-5166 | atgaaattcgctattgtcttattgt | | SEQ ID NO: 37 |
| aatD-R | aatD | 6328-6356 | tcatatctgtgtaaataaaaaaggttccg | | SEQ ID NO: 38 |
| aatPint-F | aatP | 2004-2023 | ctcgataacagagtcaatgc | | SEQ ID NO: 39 |
| aaP-F | aatP | 1432-1457 | ctttgcactattatctaaatgaggcg | | SEQ ID NO: 40 |
| aat-R | aatP | 2522-2548 | atctttcctttattgcattaacaggg | | SEQ ID NO: 41 |

Restriction Enzyme shown as the underlined sequence.

Figure 6:
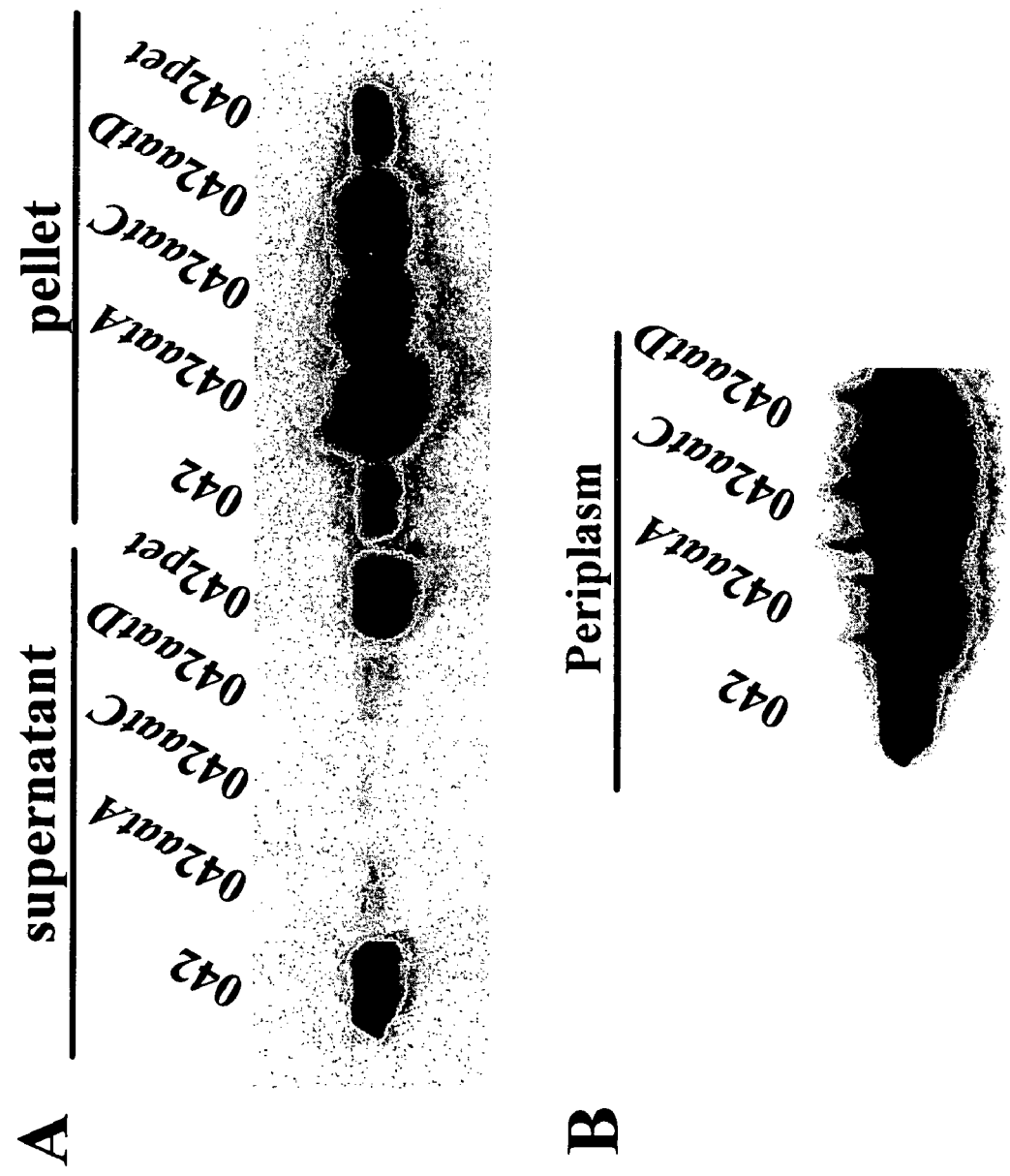
FIG. 6A is a photograph of a Western Immunoblot of secreted Aat in the supernatant and cell pellet, and illustrates different levels of expression in wild type, 042aatC and 042aatD, but not in 042pet.
FIG. 6B is a photograph of a western immunoblot of levels of Aat wild type, 042aatC, 042aatD and 042pet in periplasm.

To test the effect of AggR on the transcription of the aat cluster, RT-PCR for the aatA transcript in strains 042 and 042aggR is performed. A product of the predicted size is seen in 042 but is absent in 042 aggR. (See FIG. 6). To confirm that AggR is required for aat cluster transcription, the transcription of aatA in the complement strain is found to be under control of the arabinose-dependent promoter, 042aggR(pBADaggR). (See FIG. 6, lanes 4 and 5). The aatA transcription is restored in 042aggR(pBADaggR) when cells were grown in the presence of arabinose (ara-inducing conditions) but not in the presence of glucose (repressing conditions). aat transcription was not observed in the negative control strain 042aggR(pBAD30). (See FIG. 6, lane 3). Using similar methods, AggR is also shown to be essential in the transcription of aatP, aatC, and aatD (data not shown).

Localization of the AatA Protein

An AatA-His fusion protein is expressed and purified (see below). This protein is then used to generate a highly specific The aat Cluster is Associated with the Secretion of a Dispersin, Aap The transmembrane domain of the importers among the prokaryote ABC transporters invariably carries a conserved motif, EAA, in the C-terminal. (Holland, *J Mol Biol* 293:381-399 (1999)). Because the motif is not observed in the amino acid sequences of the aat cluster, it is hypothesized that the aat cluster exports an unidentified protein across the inner and/or outer membrane. To verify the hypothesis, the differences in secreted proteins between the wild type and the mutant in sodium dodecyl sulfate-polyacrylamide gel electrophoresis (SDS-PAGE) of culture media precipitated with trichloroacetic acid (TCA) are investigated. Strain 042 and 042aatA was cultured in high-glucose DMEM over night. The culture media were precipitated with TCA, boiled for 5 min, and separated using 15% SDS-PAGE. No significant differences of SDS-PAGE patterns of the culture media of L-broth are observed. However, a slight difference in high-glucose DMEM (FIG. 4A), in which AggR is known to be expressed, is observed.

Silver staining of the gel shows a band of 10 kD in wild type EAEC, but not in 042aatA. Because the molecular size of the mature Aap is known to be 10.2 kD, this secreted protein is predicted to be Aap. Aap is known to bind non-covalently to the bacterial cell surface, and to be easily released into the culture media by adding Triton X-100 to a final concentration of 0.1% into the medium. SDS-PAGE of the supernatant of the culture is performed with 0.1% Triton X-100. (See FIG. 4B). SDS-PAGE of the culture media of 042, 042aatA, 042aatC, 042aatD, and 042pet. The strains were cultured in high-glucose DMEM containing 0.1% Triton X-100 for 6 hours. The culture media were precipitated with TCA, boiled for 5 min, separated using 15% SDS-PAGE, and stained with Coomassie blue. The band in the wild type is easily observed by the Coomassie-staining. On the other hand, the band is not observed in 042aatA, 042aatC, and 042aatD. To eliminate the possibility of an effect of pJP5603, the mutant 042pet, which harbors pJP5603 integrated into the gene of the EAEC toxin pet, is examined as a control. The 042pet shows the same band as the wild type.

This 10 kDa secreted protein is confirmed to be Aap by western immunoblot. (See FIG. 5). Each strain was cultured in high-glucose DMEM for 6 hours with and without 0.1% Triton, and the supernatant was precipitated with TCA. The samples were then boiled and separated using 15% SDS-PAGE. The western immunoblot was performed by standard methods using the specific polyclonal antibodies against Aap.

Figure 5:
FIG. 5 is a photograph the Western Immunoblot of 042 and 042aatA in supernatant and cell pellet.

As shown in FIG. 5, Aap is observed in the supernatant of wild type EAEC in high-glucose DMEM, but not in 042aatA. The amount of secreted Aap increases after the addition of 0.1% Triton X-100 in both the wild type and 042aatA. However, the level of secreted of Aap in the wild type is much higher than that in 042aatA. The level of Aap remaining in the cell pellet is higher in 042aatA than in the wild type.

The level of secreted Aap is also reduced in 042aatC and 042aatD, but not in 042pet. (See FIG. 6A). Western Immunoblot analysis was conducted for 042, 042aatA, 042aatC, 042aatD, and 042pet in the supernatant and pellet. Each strain was cultured in high-glucose DMEM with 0.1% Triton X-100 for 6 hours. The supernatant was then precipitated with TCA, boiled, and separated using 15% SDS-PAGE. Western Immunoblot was performed by standard methods using the specific polyclonal antibody against Aap. The degree of reduction is estimated to be less than 10-fold.

In addition, western immunoblot analysis was conducted for Aap in the periplasms of 042, 042aatA, 042aatC, and 042aatD. Each strain was cultured in high-glucose DMEM over night. The periplasms were extracted as described below in the section entitled "Preparation and Analysis of Cellular Fractions".

Aap levels in the pellet and the periplasm in 042aatA, 042aatC and 042aatD are higher than in the wild type, suggesting that unsecreted Aap remains inside of the outer membrane, presumably in the periplasm. (See FIGS. 6A and 6B).

Figure 7:
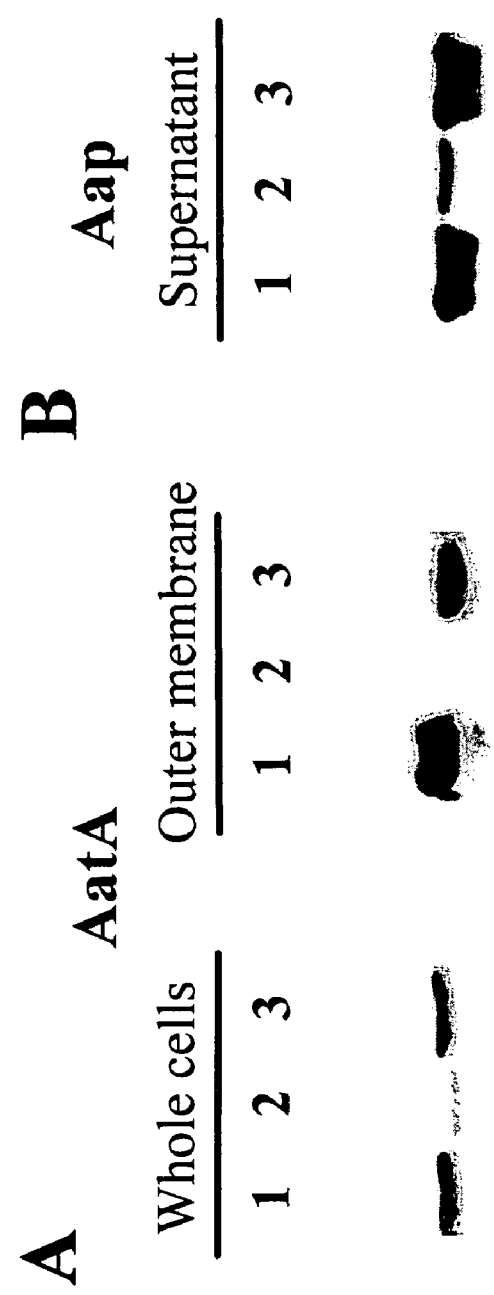
FIG. 7A is a photograph of a Western Immunoblot of whole cells and the outer membrane of 042aatA(pJNW)
FIG. 7B is a photograph of a Western Immunoblot analysis for Aap in the supernatant of 042, 042aatA, and 042aatA (pJNW)

To verify that aatA is associated with the secretion of Aap, 042aatA is complemented. Initially, pJNAD (see FIG. 3), which carries the 4.5-kb fragment encoding aatABCD cloned into the single copy expression vector pZC320, is introduced into 042aatA. However, this complement 042aatA (pJNAD) does not restore Aap secretion completely (data not shown). RT-PCR assay shows that the transcriptional level of aatA in 042aatA (pJNAD) is very low compared to the wild type (data not shown). Therefore, it is believed that the promoter of aatA exists in the upstream region of aatP.

pJNW, which contains the 6.5-kb whole aat cluster including the upstream region of aatP cloned into the pZC320 (see FIG. 3), is introduced into 042aatA. This complement is defined as 042aatA(pJNW). AatA is detected in the whole cells and the outer membrane of 042aatA(pJNW) by Western Immonoblot. (See FIG. 7A). Western immunoblot analysis was conducted for AatA in the whole cells, the outer membrane, and the supernatant of 042, 042aatA, and 042aatA (pJNW). Each strain was cultured in high-glucose DMEM over night. The outer membrane fractions were prepared as described in the section below entitled "Preparation and Analysis of Cellular Fractions". The outer membrane fraction and whole cell samples were separated using 10% SDS-PAGE after being boiled. The supernatant was precipitated with TCA, boiled, and separated using 15% SDS-PAGE. Western Immunoblot was performed by standard methods using the specific polyclonal antibodies against AatA. The secretion level of Aap is restored in 042aatA(pJNW) to a level that is almost the same as the wild type. (See FIG. 7B).

Figure 8:
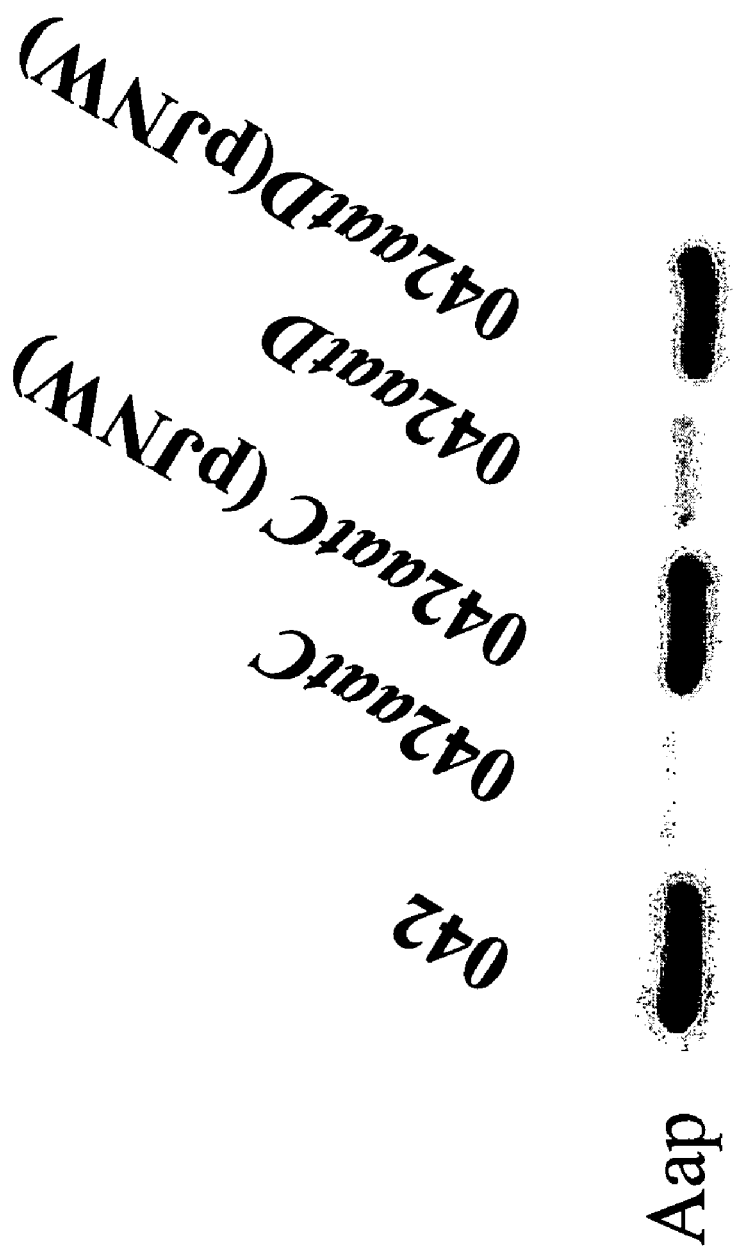
FIG. 8 is a photograph of a Western Immunoblot illustrating that the complement 042aatC(pJNW) and 042aatD (pJNW) restores Aap secretion.

The complement 042aatC(pJNW) and 042aatD(pJNW) also restores Aap secretion. (See FIG. 8). The results illustrated in FIG. 8 are the results of a western immunoblot analysis of Aap in the supernatant of 042, 042aatC, 042aatC (pJNW), 042aatD, and 042aatD(pJNW). In particular, each strain was cultured in high-glucose DMEM for 6 hours with 0.1% Triton. The supernatant was precipitated with TCA, boiled, and separated using 12.5% SDS-PAGE. Western immunoblot was performed by standard methods using the specific polyclonal antibodies against the Aap protein;

To determine the possibility of translational polar effects, pJNPA, a 3.9-kb fragment encoding aatPA cloned into pZC320 (FIG. 3), is introduced into 042aatA. This complement, 042aatA(pJNPA), restores the secretion of Aap to almost the same level as 042aatA(pJNW), suggesting that there is no polar effect of the mutagenesis.

Experimental Procedures

Bacterial Strains, Plasmids, and Growth Conditions

Strains and plasmids used herein are listed in Table 3 set forth below.

TABLE 3

Bacterial strains and plasmids

| Strain or plasmid | Characteristics | Reference or source |
|---|---|---|
| Strains | | |
| 042 | Wild-type EAEC prototype strain | Nataro 1985 |
| 042aatA | 042 harboring pJP5603 integrated into the aatA gene. $Km^R$ | This work |
| 042aatC | 042 harboring pJP5603 integrated into the aatC gene. $Km^R$ | This work |

TABLE 3-continued

Bacterial strains and plasmids

| Strain or plasmid | Characteristics | Reference or source |
|---|---|---|
| 042aatD | 042 harboring pJP5603 integrated into the aatD gene, Km$^R$ | This work |
| 042aatA(pJNW) | 042aatA carrying the whole aat cluster cloned into pZC320. Km$^R$, Ap$^R$ | This work |
| 042aatC(pJNW) | 042aatC carrying the whole aat cluster cloned into pZC320. Km$^R$, Ap$^R$ | This work |
| 042aatD(pJNW) | 042aatD carrying the whole aat cluster cloned into pZC320. Km$^R$, Ap$^R$ | This work |
| 042aatA(pJNAD) | 042aatA carrying aatA, aatB, aatC, and aatD cloned into pZC320. Km$^R$, Ap$^R$ | This work |
| 042aatA(pJNPA) | 042aatA carrying the aatP and aatA gene cloned into pZC320. Km$^R$, Ap$^R$ | This work |
| DH5α λpir | K12 E. coli lysogenized for the pir gene, which permits replication of R6K plasmid replicons | Elliott 1997 |
| S17-1 λpir | Conjugative K12 lysogenized for pir. Tet$^R$, Km$^R$ | Simon 1983 |
| 042pet | 042 harboring pJP5603 integrated into the pet gene, Km$^R$ | Henderson 1999 |
| 042aggR | 042 carrying TnphoA inserted into the aggR gene | Sheikh 2001 |
| 042aggR(pBADaggR) | 042aggR carrying the aggR gene cloned into pBAD30 to permit expression of AggR in the presence of arabinose | Sheikh 2002 |
| 042aggR(pBAD30) | 042aggR carrying pBAD30 used as a background for 042 aggR(pBADaggR) | This work |
| Plasmids | | |
| pET21 a(+) | T7 promoter-driven expression vector, Ap$^R$ | Novagen |
| pJP5603 | 3.1-kb R6K suicide plasmid, Km$^R$ | Penfold 1992 |
| pZC320 | 7.5-kb single copy vector, Ap$^R$ | Shi 1995 |
| pAatA | 1065-bp fragment of the aatA gene cloned into multiple cloning site of pET21a(+) to provide IPTG-inducible expression of the AatA protein as a 6-His fusion, Ap$^R$ | This work |
| pINTA | 520-bp internal fragment of the aatA gene in pJP5603 | This work |
| pINTC | 300-bp internal fragment of the aatC gene in pJP5603 | This work |
| pINTD | 500-bp internal fragment of the aatD gene in pJP5603 | This work |
| pJNAD | 4.5-kb PCR-derived fragment encoding aatA, aatB, aatC, and aatD. | This work |
| pJNW | 6.5-kb PCR-derived fragment of the whole aat cluster cloned into pZC320 | This work |
| pJNPA | 3.9-kb fragment encoding aatP and aatA cloned into pZC320 | This work |
| pBAD30 | High copy number expression vector permitting expression of foreign genes under control of the arabinose operon promoter | Guzman |
| pBADaggR | aggR cloned into multiple cloning site of pBAD30 to permit expression of AggR in the presence of arabinose | Sheikh 2002 |

Strain 042 was isolated from a child with diarrhea in the course of an epidemiological study in Lima, Peru, in 1983 (Nataro et al., *J Infect Dis* 152:560-565 (1985)). This strain has also been shown to cause diarrhea in adult volunteers (Nataro et al., *J Infect Dis* 171:465-468 (1995)). EAEC strains used in retrospective PCR analysis are from the Center for Vaccine Development and were isolated during epidemiological studies in various sites throughout the world. All strains are stored at −70° C. in Trypticase soy broth with 15% glycerol. All E. coli strains are grown aerobically at 37° C. in Luria-Bertani (LB) medium unless otherwise stated. Antibiotics are added at the following concentrations where appropriate: ampicillin, 100 μg/ml; kanamycin, 50 μg/ml; and nalidixic acid, 50 μg/ml.

Molecular Cloning and Sequencing Procedure

Plasmid DNA purification, restriction, ligation, transformation, and agarose gel electrophoresis are performed by standard methods (Sambrook et al., Molecular cloning: a laboratory manual, 3rd ed. Cold Spring Harbor Laboratory Press, Cold Spring Harbor, N.Y. (2001)). Plasmid DNA, except pAA2, as extracted using the QIAprep Spin Miniprep Kit or the QIAEX II Gel Extraction kit (Qiagen, Valencia, Calif.). The extraction of DNA fragments from agarose gels is performed using the Concert Rapid PCR purification kit (Life Technologies, Rockville, Md.). Plasmid DNA is introduced into E. coli DH5α, DH5α λpir, and S17-1 λpir by heat shock transformation of competent cells according to the method of Hanahan (*J. Mol. Biol.* 166:557-580 (1983)) or into 042aatA, 042aatC, and 042aatD by electroporation using a Gene Pulser II system (Bio-rad, Hercules, Calif.). DNA sequence analysis is performed at the University Maryland Department of Microbiology & Immunology Biopolymer Facility on an Applied Biosystems model 373A sequencer; template DNA was purified by using minicolumns from Amersham-Pharmacia-Biotech (Piscataway, N.J.).

PCR Procedure

Amplifications are performed with 500 ng of purified genomic DNA as templates in a 50 µl reaction mixture containing 2.5 U of Taq DNA polymerase, 0.5 µM each primer, 0.2 mM each deoxynucleoside triphosphate, 2 mM $MgCl_2$ and 5 µl of the manufacturer's buffer (Invitrogen, Carlsbad, Calif.). Amplification reactions are performed in an MJ Minicycler for 5 minutes at 94° C., followed by 30 cycles at 94° C. for 30 seconds, 50° C. for 40 seconds, and 72° C. for 1 minute per kb, concluding with extension at 72° C. for 10 minutes unless otherwise stated. The products are separated by 0.7~1.0% agarose gels, stained with ethidium bromide, and visualized with UV transillumination. The primers sequences used in this study are shown in Table 2 above.

RT-PCR Analysis

Total RNA is extracted with an RNeasy mini kit (Qiagen Inc., Valencia, Calif.) from LB culture shaking to mid-log phase. Preparations are treated with RNase-free Dnase I (Roche Molecular Biochemicals, Indianapolis, Ind.) to eliminate contaminating DNA. The absence of contaminating genomic DNA in RNA preparations is verified by performing PCR for the chromosomal chloramphenicol acetyltransferase (cat) gene. To synthesize cDNA, total RNA (2 µg) is subjected to reverse transcriptase (RT) reactions using Thermoscript RT (Invitrogen) and gene-specific reverse primers according to the manufacturer's instructions. Primers used for RT-PCR are shown in Table 2. Amplification reactions were performed in an MJ Minicycler for 5 minutes at 94° C., followed by 30 cycles of 94° C. for 30 seconds, 50° C. for 40 seconds, and 72° C. for 1 minute per kb, concluding with extension at 72° C. for 10 minutes unless otherwise stated. The products were separated by 0.7~1.0% agarose gels, stained with ethidium bromide, and visualized with UV transillumination.

Isolation of Aap

Although an isolation technique for isolating Aap is described below, the isolation of AatP, AatA, AatB, AatC, and AatD is conducted in a like manner.

Given that Aap is the dominant protein non-covalently attached to the surface of EAEC bacteria, it can easily be isolated. The bacteria are cultured overnight at 37° C. in Minimal Essential Medium or L-broth, either containing 0.05% glucose to maximize Aap expression. After cultivation, the bacteria are pelleted by centrifugation for 20 minutes at 20,000×g. The bacterial pellet is then resuspended in PBS with 0.1% Triton and incubated at 37° C. for one hour. The bacteria are then pelleted as before. The supernatant contains substantially pure Aap protein (ca. 95%).

AatA Expression and Purification

Although the AatA expression and purification are described below, the expression and purification of Aap, AatP, AatB, AatC, and AatD is conducted in the same manner.

The aatA gene product is expressed by cloning a 1064-bp fragment generated by PCR into the BamHI and EcoRI sites of the expression vector pET21a(+) (Novagen, Madison, Wis.). The primer sequences of aatA-F and -R for amplification are shown in Table 2. The protein is thereby synthesized as a fusion with a hexa-His-tag to the carboxy terminus and T7-tag. Protein expression is achieved by incubating an LB culture of the construct at 37 ° C. with shaking until an optical density at 600 nm of 0.5 to 0.6 was reached. Cells were induced with a final concentration of 0.4 mM isopropyl-β-D-thiogalactopyranoside (IPTG) (Sigma Chemical Co., St. Louis, Mo.) for 3 hours. The fusion protein is purified in the denaturing condition by passage through a metal affinity matrix according to the standard protocols supplied with the Talon metal affinity resin (Clontech, Palo Alto, Calif.). The column eluate is dialyzed overnight against PBS containing 8 M urea (pH 7.4). His-tag fusion protein is separated by SDS-PAGE and detected by staining with Coomassie brilliant blue R250. To determine the identities of the protein of interest, the bands are excised from gel and analyzed by mass spectrometry at the Protein and Nucleic Acid Research Facility, Stanford University School of Medicine, Palo Alto, Calif.

Preparation of AatA-Specific Antibodies

Although the preparation of AatA-specific antibodies are described below, antibodies to Aap, AatP, AatB, AatC, and AatD are prepared in the same manner.

Antibodies Rabbit antiserum specific for AatA is raised by subcutaneous injection of AatA preparations in Freund's adjuvant as described in Harlow et al., 1998. Affinity purification of antiserum is performed to purify AatA-specific antibodies. His-tag AatA fusion proteins (10 mg) is coupled to CNBr-activated Sepharose 4B (Pharmacia, Uppsala, Sweden). Rabbit antiserum is adsorbed by mixing with His-AatA protein-coupled Sepharose for 2 hours at room temperature. After washing, bound antibodies are eluted with 0.2 M glycin (pH 1.85) and immediately neutralized with 1 M Tris-HCl (pH 8.5). The eluate is dialyzed against PBS, concentrated using a Vivaspin 20, 50,000 MWCO (Vivascience, Hannover, Germany), and then subsequently is used for Western Immunoblot.

Monoclonal antibodies could be raised against Aap by injecting the purified protein into mice. 50 mcg of purified Aap protein would be injected with Freund's adjuvant into each of three mice on days 0, day 14, day 28 and day 43. Three days after the final boost, mouse lymphocytes are isolated and fused with myeloma cells according to standard procedures. Twenty four days after fusion, cell lines are screened for antibody production by examining the medium of individual colonies for the presence of antibodies to Aap by Western blot. Colonies with high level specific antibody production will be expanded to full cell culture flasks and saved for future use.

Polyclonal antibodies are raised by injection of gel slices into New Zealand White rabbits. A preparation containing 20 mcg of pure Aap protein is added to SDS-PAGE running buffer (available commercially from Bio-Rad) and separated on an SDS-PAGE gel (15% gel) for 4 hours. The gel is then stained with Coomassie Brilliant Blue (Bio-Rad) and visualized. The band corresponding to Aap is easily identified by size. The band is excised from the gel using a razor blade, and the band is chopped into very small slices with the blade. The slices are mixed with an equal volume of PBS and drawn in and out through a 20 gauge hypodermic needle to further homogenize the gel slice in the PBS. When only small (ca. 1 mm) lumps are left, the slurry is injected subcutaneously into the subcutaneous region on the back of a 1.5 kg New Zealand White rabbit. Typically the injectate is divided into 3-4 injections. This procedure is repeated two weeks later, then again four weeks after the second injection. One week after the third injection, the rabbit is bled for antiserum. The blood is allowed to clot at room temperature for 3 hr, then the blood is centrifuged at 15,000×g for 10 minutes. The supernatant is removed and stored at −20° C. Preparation and analysis of cellular fractions To prepare culture supernatant fractions, strains are grown overnight or for 6 hours at 37° C. in 5 ml of high-glucose DMEM. The growth rate of mutants is almost the same as that of the wild type (data not shown). After centrifugation at 13,000×g for 5 minutes, proteins in the supernatant are precipitated with trichloroacetic acid (TCA). One-fourth volume of TCA containing 0.4% (wt/vol) deoxycholate is added to the supernatant in an eppendorf tube, and incubated on ice for 30 minutes after vortexing. The pellet is centrifuged at 14,000×g for 15 minutes and washed with 1.5 ml of acetone for 15 minutes at room temperature. The pellet is again collected by centrifugation at 14,000×g for 15 minutes, dried, and suspended in 50 µl of Laemmli sample buffer. To detect Aap that attached to the outer membrane non-covalently, strains are grown in medium with 0.1% Triton X-100. The supernatant is precipitated with TCA.

Outer membrane proteins are extracted from cultures grown overnight at 37° C. in 20 ml of high-glucose DMEM. Bacteria are harvested by centrifugation at 6,000×g for 10 minutes at 4° C. and resuspended in 3.0 ml of 10 mM Tris, pH 8.0. The cells are lysed with a French press and centrifuged for 30 minutes at 13,000 g at 4° C. The pellet is resuspended in 240 µl of 10 mM Tris, pH 8.0, 60 µl of 10% Triton X-100, and 1.5 µl of 1M MgCl$_2$ (Skare, et al., *J Bacteriol* 178:4909-4918 (1996)) or 35 µl of distilled H$_2$O and 265 µl of Sarkosyl (Amako, et al., *Microbiol Immunol* 40:749-754 (1996)). It is incubated at room temperature for 20 minutes, and the pellet is resuspended in 50 µl of Laemmli sample buffer.

Periplasms are extracted from cultures grown overnight at 37° C. in 5 ml of high-glucose DMEM. Bacteria are harvested by centrifugation at 3,800×g for 10 minutes and resuspended in 500 µl of lysis buffer (50 mM Tris, pH 8.0, 3 mM EDTA, and 01% Triton X-100) (Thorstenson, et. al., *J Bacteriol* 179:5333-5339 (1997)). The suspension is kept on ice for 30 minutes, and centrifuged for 15 minutes at 3,800×g. The supernatant is stocked and the pellet is resuspended in 500 µl of lysis buffer. The suspension is centrifuged for 15 minutes at 3,800×g. The supernatants are collected and precipitated with TCA as described above. The pellet is resuspended in 100 µl of Laemmli sample buffer.

One-dimensional SDS-PAGE (Laemmli et al., *J Mol. Biol.* Vol. 47(1):69-85 (1970)) is performed using 10~15% (wt/vol) acrylamide separating gels and 4.0% (wt/vol) acrylamide stacking gels. Samples are routinely heated for 5 minutes at 100° C. in Laemmli sample buffer (Laemmli et al., *Nature* 227:680-685 (1970)) prior to loading. Proteins are detected by staining with Coomassie brilliant blue or Silver Stain Kit (Bio-Rad Laboratories, Inc., Hercules, Calif.).

Western Immunoblot Analysis

Preparative protein samples were boiled for 5 minutes, separated by SDS-PAGE (10.5%, 12.5%, or 15%), and transferred onto Immobion-P membranes (Millipore). Dried skimmed milk (5% [wt/vol]) is used as a blocking reagent. For detection of AatA and Aap, an anti-AatA specific antibody and an anti-Aap antiserum are used at a dilution of 1:1,000 and 1:8,000, respectively. Antigen-antibody complexes are reacted with a horseradish peroxidase-conjugated goat anti-rabbit IgG at a dilution of 1:40,000 and visualized using a chemiluminescence ECL kit (Amersham, Uppsala, Sweden).

Mutagenesis and Complementation

To construct the aatA mutant, an internal portion of the aatA gene (nucleotides 2893 to 3412) is generated by PCR and cloned into XbaI and EcoRI sites of the suicide vector pJP5603, whose replication requires a copy of the R6 K pir-encoded π protein supplied in trans (Penfold et al., *Gene* 118:145-146 (1992)). The sequences of primers used to amplify the internal fragment are shown in Table 2. The resulting plasmid, pINTA, is propagated in *E. coli* DH5αλpir prior to transformation into the donor *E. coli* strains in SI 7-1 λpir. The mutant strain is then obtained by conjugal mating between the wild type parent strain 042 (which is nalidixic acid resistant) and *E. coli* strains in S17-1 λpir. Transconjugants are selected on LB agar supplemented with kanamycin and nalidixic acid. This process results in integration of pINTA into the homologous site in the aatA gene (and hence a merodiploid state). The resulting strain is designated 042aatA. The insertion of the suicide plasmid into the native aatA gene is confirmed by restriction analysis of the pAA2 plasmid using MluI and BamHI. Lack of the aatA transcript and the AatA protein is confirmed by RT-PCR and Western immunoblot, respectively.

To construct the aatC and the aatD mutant (042aatC and 042aatD, respectively), an internal portion of each gene (nucleotides 4610 to 4909 and 5361 to 5860, respectively) is generated by PCR and cloned into pJP5603 (pINTC and pINTD, respectively). The sequences of primers used to amplify the internal fragment are shown in Table 2. The 042aatC and the 042aatD are generated as described above. Lack of the aatC and aatD transcript is confirmed by RT-PCR.

To construct the trans complement of mutants, the whole aat cluster is amplified by PCR and cloned into the single copy vector pZC320. The primer sequences of aatW-F and -R used for amplification are shown in Table 2. Amplifications are performed with 500 ng of purified genomic DNA as templates in a 50 µl reaction mixture containing 2.5 U of Platinum pfx DNA polymerase, 0.5 µM each primer, 0.3 mM each deoxynucleoside triphosphate, 2 mM MgCl$_2$ and 5 µl of the manufacturer's buffer (Invitrogen, Carlsbad, Calif.). Amplification reactions are performed in an MJ Minicycler for 5 minutes at 94° C., followed by 30 cycles at 94° C. for 30 seconds, 54° C. for 40 seconds, and 68° C. for 6.5 minutes, concluding with extension at 68° C. for 10 minutes. The 6.5-kb PCR product is cloned into the BamHI and NotI sites of the vector pZC320. This plasmid is designated pJNW. pJNW is introduced into 042aatA, 042aatC, and 042aatD by electroporation.

pJNPA, 3.9-kb fragment encoding aatP and aatA cloned into pZC320, is constructed in the same manner as described above using the primer aatW-F and aatPW-R. pJNPA is introduced into 042aatA by electroporation. pJNAD, the 4.5-kb fragment encoding aatABCD cloned into pZC320, is also constructed, and introduced into 042aatA.

Computer and Statistical Analysis

Analysis of DNA and protein sequence is performed using programs available through the National Center for Biotechnology Information (www.ncbi.nlm.nih.gov) and the ExPASy server of the Swiss Institute of Bioinformatics (www.expasy.ch). Statistical testing is performed using Fisher's exact test. Probability values less than 0.05 are considered significant.

Identification of the aap Gene

As mentioned above, aap is located on pAA approximately 843 nucleotides upstream from the aggR start codon. SDS-PAGE was performed by the standard method of Laemmli et al., J Mol. Biol., Vol. 47(1):69-85 (1970) as described in Ausubel et al. All of the gels are run on the Mini-Protean III electrophoresis system from Bio-Rad using 1 mm spacers. All of the reagents for SDS-PAGE are purchased from Bio-Rad, Inc. (Hercules, Calif.). The gels used in the SDS-PAGE are 10% polyacrylamide unless otherwise specified. All of the samples are prepared in BioRad SDS-PAGE running buffer and boiled for 10 minutes prior to gel loading. The gels were stained in Coomassie blue using gel staining reagents from BioRad according to manufacturer's protocols.

The aggR gene is located downstream of the fimbrial subunit (aafA) on the pAA plasmid of prototype EAEC strain 042. This region is completely conserved in the sequence of the AAF/I-encoding plasmid of strain 17-2, with 97% sequence homology and conservation of all open reading frames.

Further, it was determined that the Aap sequence featured two cysteine residues that may form a disulfide loop, but there was no other distinguishing amino acid motifs or properties.

Construction of an aap Knockout Mutation in Strain 042

An aap mutant is constructed in *E. coli* strain 042 by a single crossover insertion of suicide plasmid pJP5603 using the following methods:

A DNA fragment internal to aap is synthesized by PCR using the following primers:

```
                                    (SEQ ID NO. 14)
5'-ATGGTACCTTGTTATCTTTTCTGGCATCTTGGGT-3'
                                    (SEQ ID NO. 15)
5'-ATGAGCTCTGGAGGGGGTAACAACCCCTTTGAAGT-3'.
```

PCR is performed using the Optiprime kit (buffer 8) from Stratagene, Inc. (La Jolla, Calif.) according to manufacturer's instructions.

The PCR reaction is performed in a PTC-150 Minicycler from MJ Research, Inc., (Watertown, Md.) using the following program: 40 cycles at 94° C. for 1 minute, 58° C. for 90 seconds, 72° C. for 2 minutes; followed by a single extension reaction at 72° C. for 10 minutes.

Next, the reaction product is digested with restriction enzymes KpnI and SacI (Gibco/BRL, Gaithersburg, Md.) for 3 hours and then separated by agarose gel electrophoresis using standard methods. The fragment is excised from the gel and cloned into suicide vector pJP5603 (obtained from Dr. J M. Pemberton and referenced in Penfold R J and Pemberton J M, Gene 118:145;1992), previously digested with the same restriction enzymes for 3 hour. *E. coli* suicide vector pJP5603 is kanamycin resistant and has the suicide R6K replicon.

Ligation is performed by standard protocols disclosed in Ausubel et al. with a DNA ligase obtained from Gibco/BRL for 18 hours at room temperature using a buffer provided by the manufacturer and ATP obtained from Gibco/BRL. The volume of the ligation reaction is 20 µl. 5 µl are used to transform *E. coli* DH5α(λpir) using standard calcium chloride transformation conditions according to standard protocols. The recombinant plasmid is then purified using the Qiagen midi-plasmid kit according to manufacturer's instructions. (Qiagen, Inc., Valencia, Calif.). 1 µg of purified plasmid DNA is transformed into strain S17-1 (λpir) according to the standard calcium chloride technique.

Strain S17-1(λpir) is used for mobilization of the plasmid into strain 042. S17-1(λpir) carrying the pJP5603aap construct and recipient strain 042 (Nalidixic acid resistant) are each grown in Luria broth to log phase (3 hr) at 37° C. 100 µl of each broth culture are then mixed on a cellulose nitrate disc (obtained from Scheicher and Schuell, Inc., Keene, N.H.) which had been applied to a Luria agar plate without antibiotics. The plate is incubated overnight at 37° C. The following day, bacterial growth is resuspended in L-broth and plated on L-agar with ampicillin (100 µg/ml) and nalidixic acid (100 µg/ml). After overnight incubation, individual colonies are picked and the insertion of the suicide plasmid into the native aap gene is confirmed by extracting the 100 kb pAA2 plasmid and digesting it with BamHI and HindIII restriction enzymes. Since the pattern of digestion of the native plasmid is known, the sites of insertions are be easily determined.

The resulting *E. coli* strain is designated 042aap. The construct contained the pJP5603 plasmid integrated into the aap gene on native plasmid pAA2. The method of inactivation results in a merodiploid duplicate for the aap fragment cloned into pJP5603. Lack of Aap expression was confirmed by Western blot as follows. 042aap is grown in L-broth for 3 hours at 37° C. with shaking. The bacteria are pelleted by centrifugation (10,000×g) and 20 µl of the culture supernatant are mixed with SDS-PAGE running buffer (obtained from Bio-Rad Inc., Hercules, Calif.), then separated on a 10% SDS-PAGE gel. The gel is then transferred to nitrocellulose paper by electroblotting. Electroblotting is performed using a Bio-Rad Mini-Transfer system at 60 V for 4 hours at 4° C. in Towbin's Tris/Glycine buffer with 20% methanol.

After transfer to nitrocellulose membrane (Schleicher and Schuell, Keene, N.H.), the blot is blocked in phosphate-buffered saline with 0.5% Tween 20 (Sigma Chemical Co., St. Louis Mo.) with 5% skim milk (Carnation, Nestle, Inc., Glendale, Calif.) overnight at 4° C. The blot is then incubated with anti-Aap antibody (raised as described below) at a dilution of 1:2000 in PBS 0.5% Tween-20 (Sigma Chemical Co., St. Louis Mo.) for 18 hours. Next, the blot is incubated with 0.5% skim milk for 2 hours at room temperature and then washed three times with PBS containing 0.5% Tween-20. The blot is then reacted for 1 hour at room temperature with a secondary antibody, which was a 1:40,000 dilution (in PBS Tween) of goat anti-rabbit-horse radish peroxidase conjugate. (Amersham Pharmacia Biotech, Piscataway, N.J.). The blot is then washed three times with PBS Tween. The blot is then developed with an chemiluminescence kit from Amersham Pharmacia according to manufacturer's instructions. The blot is then air dried and exposed to X-ray film. (X-omat film, Kodak, Rochester, N.Y.).

All of the PCR reactions were performed using buffers from Stratagene Inc. (La Jolla, Calif.) and protocols from the manufacturer. Details specific for each PCR reaction are provided below.

Isolation and Purification of Aap Protein and Generation of Antibodies

For purification of the Aap protein, the aap polynucleotide is ligated into plasmid pQE70 (with the resultant plasmid designated pAap) downstream of the lac promoter and upstream of six histidine residues. A native Aap protein carrying an additional six histidine residues fused to the carboxy terminus of the protein is produced. The aap gene is amplified by PCR using primers with the following sequences:

```
                                    (SEQ ID NO: 16)
5'-ACATGCATGCAAAAAATTAAGTTTGTTATC-3';
and
                                    (SEQ ID NO: 17)
5'-CGGGATCCAACCCATTCGGTTAGAGC-3'.
```

Amplification is performed using buffer number 8 and other reagents in the Opti-Prime kit from Stratagene, Inc. (La Jolla, Calif.) according to manufacturer's protocols. The PCR reaction is performed in an PTC-150 Minicycler thermal cycler (MJ Research, Inc.) programmed for the following sequence of steps: 94° C. for 3 minutes; followed by 35 cycles at 94° C. for 1 minutes, 43° C. for 3 minutes, 72° C. for 2 minutes; followed by a final extension at 72° C. for 10 minutes. This reaction results in a polynucleotide fragment with SphI and BamHI restriction sites at the aap upstream and downstream ends respectively.

After amplification, the PCR product is digested with SphI and BamHI (according to manufacturer's instructions; Gibco/BRL, Gaithersburg, Md.) and ligated into expression vector pQE70, digested with the same enzymes. The ligation reaction is used to transform *E. Coli* strain DH5α by the calcium chloride technique. The resulting plasmid is designated pAap.

Plasmid pAap DNA is isolated from DH5αpAap using the Qiagen plasmid extraction kit according to manufacturer's instructions (Qiagen, Valencia, Calif.). The plasmid DNA is confirmed to be the desired construct by restriction digestion using SphI and BamHI. PCR is performed using the same primers and conditions employed to generate the fragment used for cloning. The construct produces a product of the desired size.

The pAap plasmid is extracted as described above then electroporated into E. coli 042aap. 042aap is made competent by the method described in Ausubel et al., as follows: 042aap is grown overnight in 500 ml L-broth with shaking to an OD600 of 0.6. The culture is then chilled on ice and harvested by centrifugation. The pellet is resuspended in 500 ml ice-cold water and centrifuged again. This process is repeated. The final pellet is resuspended in 5 ml ice water.

Electroporation is performed using a Gene Pulser from Bio-Rad, Inc. 0.5 μg purified plasmid DNA resuspended in distilled water is added to 0.5 ml cell suspension in a 0.2 cm cuvette from Bio-Rad. The Gene Pulser is set for 2.5 kV, 25° F., 200 ohms and a single pulse is applied. 1 ml SOC medium (Gibco/BRL, Gaithersburg, Md.) is then added, and the culture is incubated at 37° C. for 30 minutes with shaking prior to plating on L-agar plates with 100 mcg/ml ampicillin (Sigma).

Western immunoblot analysis of E. Coli 042aap(pAap) using anti-Aap antibodies indicate the restoration of Aap expression. Levels of Aap expression in E. coli 042aap(pAap) in the absence of IPTG induction are slightly higher than native levels.

The Aap-6His fusion protein is purified from a 100 ml culture volume grown in L-broth with shaking at 37° C. until an OD of 0.6 is reached. At this point, IPTG (Sigma Chemical Co, St. Louis, Mo.) is added to a concentration of 1 mM and incubation at 37° C. is continued for an additional 4 hours. The bacterial cells are then pelleted by centrifugation at 4,000×g for 20 minutes. Extraction of the protein is performed as described in protocol 10 ("Purification of periplasmic proteins") in the QIAexpressionist manual (Version 3/99; Qiagen, Inc, Valencia, Calif.). In particular, the cell pellet are resuspended in 30 mM Tris-Cl, 20% sucrose, pH 8.0 at 80 ml per gram wet weight of pellet. EDTA is then added to reach a concentration of 1 mM and the cells are gently stirred for 10 minutes. The cell suspension is then centrifuged at 8000×g for 20 minutes at 4° C., and the pellet is resuspended in the same volume of cold 5 mM $MgSO_4$. Next, the suspension is stirred gently for 10 minutes, then centrifuged at 8000×g for 20 minutes at 4° C. The supernatant is then dialyzed 3 times (at least 6 hours each) against 1 L of lysis buffer comprising 8 M urea, 0.1 M $NaH_2PO_4$, 0.01 M Tris-Ci pH 8.0. It is to be noted that dialysis is performed here and elsewhere in the application using Spectra/Por 5,000 Da MW cutoff dialysis tubing (Spectrum Medical Industries, Inc., Houston Tex.).

The cleared lysate obtained above is then subjected to Ni-NTA purification using protocol 14 from the QIAexpressionist manual (Version 3/99). Briefly, the purification is performed as follows: 1 ml 50% Ni-NTA slurry (Qiagen, Inc.) is added to 4 ml cleared lysate and mixed gently for 60 minutes on a rotary shaker. The mixture is then loaded into a 5 ml chromatography column (from Qiagen, Inc) and the flow through is collected. The column is washed twice with 4 ml "buffer C" [8 M urea, 0.1 M NaH2PO4, 0.01 M Tris-Cl pH 6.3]. The column is then eluted with 4 washes with 0.5 ml "buffer D" [8 M urea, 0.1 M $NaH_2PO_4$, 0.01 M Tris-Cl pH 5.9], followed by 4 similar washes with "buffer E" [8 M urea, 0.1 M $NaH_2PO_4$, 0.01 M Tris-Cl pH 4.5]. Most of the Aap-6His protein is found in the buffer E washes. These fractions are pooled and dialyzed against three changes of phosphate-buffered saline for 18 hours each, using 5,000 Da MW dialysis tubing (Spectrum).

High quality polyclonal antiserum is raised against the purified Aap-6His protein fusion by subcutaneous injection of rabbits (as described below). The Aap protein containing the Histidine tag is purified by chromatography through a Nickel-based column provided by Quiagen, Inc., according to manufacturer's instructions.

After elution from the column, the protein is separated on 10% SDS-PAGE and excised from the gel using a razor blade. The identity of the protein is confirmed by N-terminal sequence analysis using automated Edman degradation in the Protein and Nucleic Acid Facility, Stanford University School of Medicine. Approximately 1 mg of the protein contained within the gel slice was then macerated and injected subcutaneously into a 1.5 kg New Zealand White rabbit. 2 weeks later a second duplicate gel slice containing protein is injected in the rabbit in an identical fashion. 3 weeks after the second injection, the rabbit is bled. Blood is permitted to clot at room temperature overnight, and the erythrocytes are then pelleted at 3,000×g and the serum is collected. The serum is stored at −20° C. An aliquot of the serum is absorbed for cross-reacting antibodies by reacting 1 ml of antiserum (diluted to 10 ml final volume with PBS) overnight with E. coli agarose beads (Sigma Chemical Co, St. Louis, Mo.) according to manufacturer's instructions. The resulting absorbed antiserum is found to react only with the Aap-6His protein by Western blot analysis, performed as described above.

Function of Aap

Overnight growth of strain 042 in L-broth at 37° C., produces aggregates ("flocs") of bacteria that settled to the bottom of the culture tube. 042aap produces a larger volume of precipitated material (to the naked eye) after overnight growth. In addition, 042aap(pAap) produced a similar amount of culture precipitate compared to strain 042.

Expression of AAF/II Fimbriae

Expression of AAF/II fimbriae is observed by scanning electron microscopy. Strains to be examined are grown in L-broth overnight with shaking at 37° C. Bacterial cultures are spotted onto silica chips (Ted Pella, Inc., Redding, Calif.) previously coated with poly-lysine for 5 minutes. The poly-lysine stock consisted of 0.1% poly-lysine (Sigma Chemical Co, St. Louis, Mo.) in distilled water. 30 μl of the overnight bacterial culture are spotted onto the chip and allowed to incubate at room temperature for 5 minutes. Water is withdrawn using a Pasteur pipette and then 2% glutaraldehyde (E.M.S., Inc, Fort Washington., Pa.) in CaCo buffer (0.1 M Ca cacodylate, 3 mM $CaCl_2$, all reagents from E.M.S., Inc.) are applied for 1 hour and incubated at room temperature. The liquid is withdrawn and 0.1 M CaCo buffer is applied 3 times for five minutes each wash. The specimen is then post-fixed with 2% osmium tetroxide (E.M.S., Inc) in CaCo buffer for 1 hour on ice. The specimens are then rinsed twice with distilled water for five minutes each. The specimens are then stained with 2% uranyl acetate (Ted Pella, Inc.) for 30 minutes at room temperature, rinsed with 50% ethanol, then dehydrated in a series of ethanol baths for 5 minutes each (50%, 70%, 90%, 100%). The 100% ethanol wash step is performed three times for 5 minutes each. The specimens are then inserted into the critical point dryer (model CPD-030, Bal-Tec AG, Balzers, Switzerland) until dry, followed by sputter coating in a Desk II Cold Sputtercoater for 90 seconds using platinum/paladium for 90 seconds according to manufacturer's protocols (Denton Vacuum, Inc, Moorestown, N.J.). The specimens are then examined by scanning electron microscopy in a Leo 1550 field emission scanning electron microscope (Leo Electron Microscopy Inc, Thornwood, N.Y.).

Localization of the Aap Protein

To localize Aap in wild type E. coli 042, cell fractionation experiments of wild type E. coli 042 and 042aap are performed. Cultures of the test bacteria are inoculated into 5 ml L-broth cultures and incubated overnight at 37° C. with shaking. For the respective fractions, samples are prepared as follows:

(1) Supernatant: 100 μl of culture is withdrawn and the bacteria are pelleted by centrifugation. 20 μl of the remaining supernatant is applied to an SDS-PAGE gel.

(2) Periplasm: The pellet from a centrifuged 5 ml culture is resuspended in 1 ml 30 mM Tris-HCl, 20% sucrose, pH 8.0. On ice, EDTA (0.5 M stock solution, Sigma Chemical) is added to bring the final concentration to 1 mM. After five minutes on ice, the cells are pelleted by centrifugation and then resuspended in 1 ml cold 5 mM MgSO4 (Sigma). The suspension is stirred for 10 minutes. The cells are then pelleted by centrifugation and 20 μl of the supernatant is run on SDS-PAGE as the periplasmic fraction.

(3) Whole cell: After centrifugation, the remaining pellet is aspirated and the cell pellet resuspended in an equal volume of SDS-PAGE running buffer. The suspension is boiled for 10 minutes. 10 μl of this preparation is run on the gel.

By running SDS-PAGE gels and extrapolating back to the number of cells in the original culture, it is estimated that at least 50% of Aap produced by strain 042 is localized to the culture supernatant and free from the bacterial cell. Whole cell lysates of culture pellets indicate that the majority of cell associated Aap is in the 12 kDa unprocessed cytoplasmic form. It is also determined that the Aap protein has an excellent signal sequence between residues 21 and 22 of SEQ ID NO: 1.

Role of Aap in Intestinal Adherence

Because of the decrease in aggregation of E. coli 042aap (pAap), the ability of the aap mutant to adhere to human mucosa in in vitro organ cultures (IVOC) is examined. Colonic samples are obtained with fully informed parental consent from pediatric patients undergoing colonoscopy for possible inflammatory bowel disease. All tissue used in these experiments are determined normal by pathologic examination prior to experimentation.

Endoscopy is performed using an Olympus PCF pediatric endoscope. 2-3 mm$^2$ biopsy specimens are taken from the transverse colons from 6 pediatric patients (5 male: 1 female; aged 41-174 months, median age 107 months). Tissue is mounted (mucosal surface upwards) on a foam support (polyethylene packing foam taken from discarded packing material) in a petri dish (VWR Scientific, Dorset, England) at 37° C. in a 95% $O_2$ and 5% $CO_2$ atmosphere. The tissue is partially submerged in medium containing a 1:1 mixture of NCTC-135 medium and DMEM containing 0.5% d-mannose, with 10% (vol/vol) newborn calf serum (Gibco/BRL, Gaithersburg Md.). The medium is changed every two hours to maintain pH and nutrient supply. Bacteria are grown in brain heart infusion broth (Difco, Becton Dickenson, Franklin Lakes, N.J.) for eighteen hours at 37° C. without agitation. 25 μl of the overnight bacterial culture is applied to the tissue and incubated for eight hours. The tissue specimens are washed three times in fresh NCTC-135/DMEM medium to remove any non-adherent bacteria. Specimens are then fixed in 3% phosphate-buffered saline glutaraldehyde (Sigma Chemical Co, St. Louis Mo.) and postfixed in 1% aqueous osmium tetroxide (mfg). Specimens are then taken through a graduated series of ethanol and critical point dried in liquid $CO_2$, using a Polaron E3000 critical point drying apparatus. Samples are sputter-coated with gold palladium in a Polaron E5100 series II coating system and examined in a JEOL JSM scanning electron microscope (JEOL, Inc., Peabody, Mass.). Eight hour pediatric intestinal IVOC are compared with uninoculated controls and wild type E. coli 042.

E. coli 042 wild type adhere to the mucosa with thick aggregates of bacteria and single bacteria. In contrast, the aap mutant (E. coli 042aap) adhered in "super-aggregates" with virtually no single bacteria on the mucosal surface. Thus, the IVOC experiments illustrate that Aap helps in the dispersal or non-aggregation of EAEC.

Expression Conditions of aap

Aap is expressed maximally during the logarithmic growth phase. E. coli 042 is cultured in L broth at 37° C. with shaking and 2 ml samples are withdrawn from the culture every two hours. The bacterial cells are pelleted by centrifugation at 10,000×g and 50 μl of the supernatants are mixed with an equal volume of SDS-PAGE loading buffer (BioRad, Valencia, Calif.). The samples are then boiled for 10 minutes and run on a 10% SDS-PAGE gel. The gel is then electroblotted to Nylon membrane and subjected to immunoblot using anti-Aap antiserum. Aap expression is shown to be the highest during mid-logarithmic phase.

The Usher Chaperone Pathway

Aap has several attributes characteristic of bacterial pilin subunits, including small size, a cleavable signal sequence, two cysteine residues capable of forming a disulfide loop, and C-terminal glycine residues which could indicate association with a PapD-like chaperone protein.

It has been shown that AAF/II expression is dependent on the PapD-like chaperone AafD and the PapC usher homolog AafC. (Elias, et al., J Bacteriol 181:1779-85 (1999)). Organization of biogenesis genes for Aggregative Adherence Fimbria II defines a virulence gene cluster in enteroaggregative E. coli. (Id.).

Mutants of strain 042 with insertions of pJP5603 are examined for their abilities to secrete Aap into the intracellular space. (Id.). The method for the insertion of pJP5603 is described above.

Aap was detected in supernatants of E. coli 042 and E. coli 042 with insertional mutations in the aafD, aafC, and aafA genes. Aap is undetectable in the aafD and aafC mutants. However, Aap is secreted at greater than wild type levels in aafA mutants (i.e., deficient in expression of the AAF/II major fimbrial subunit).

To further demonstrate this point, the following experiments are conducted to determine the presence of the Aap protein in cultures of E. coli HS carrying plasmid pAA2 and pAA2 with mutations in aafC, aafD and aafA. Identical results are observed when compared with the wild type strain, indicating that Aap expression is dependent on the usher-chaperone system of E. coli strain 042, but not on the expression of the AAF/II fimbriae themselves.

Diagnosis of EAEC Infection

Although the diagnosis of an EAEC infection is described below using an antibody specific for Aap, antibodies to AatP, AatA, AatB, AatC, and AatD can be used for diagnosis in a similar manner.

Individuals with EAEC will most likely pass in their stools EAEC which express the Aap protein on the bacterial surface. Therefore, detection of E. coli expressing Aap, by immunologic or genetic methods will diagnose EAEC infection. Immunologic detection can be performed by the slide agglutination method, using antibodies to Aap. The antibodies can be used alone or conjugated to latex beads.

Because the aap gene is present only in EAEC strains, the presence of E. coli carrying the aap gene will diagnose an EAEC infection. One useful way to find the aap gene in an *E. Coli* colony is via polymerase chain reaction, PCR. PCR could be performed on *E. Coli* isolated from the stools of patients with diarrhea. A positive reaction would diagnose the infection. A patient's stool would be plated on MacConkey medium and incubated overnight at 37° C. After such incubation, the plate would be examined and lactose positive colonies would be picked with a toothpick and resuspended in 500 mcl of distilled water, then boiled for 10 min. 2 mcl of this preparation would then be added to an aqueous buffer containing 10 mM Tris-HCl [pH 8.3], 50 mM KCl, 2 mM $MgCl_2$, 100 μM each dATP, dCTP, dGTP, and dTTP, 2.5 U of Ampli Taq polymerase [Perkin-Elmer, Norwalk, Conn.]), 25 pmol of each aap primer. The sequences of PCR primers are

```
                                          (SEQ ID NO: 18)
    5'-TTGTTATCTTTTCTGGCATCTTGGGT-3';
and (SEQ ID NO: 19)
    5'-GAGGGGGTAACAACCCCTTTGAAGT-3'.
```

The reaction mixture is heated to 94° C. for 5 min and then subjected to 35 cycles (94° C. for 30 s, 50° C. for 1 min, and 72° C. for 45 s) of amplification, and then to a final extension at 72° C. for 7 min in a DNA thermal cycler. Then 10 μl of each of the amplified PCR products is added to a 1% agarose electrophoresis gel with a 1-kb DNA molecular weight marker (Gibco BRL). A positive reaction is defined as the presence of the PCR product of the expected size of 0.4 kb.

Colony blot hybridization is performed by standard methods (Sambrook and Russell, Molecular Cloning: A Laboratory Manual, Cold Spring Harbor Laboratory Press, 2001; pp. 1.126-1.142). A piece of nitrocellulose paper (Millipore HAWP) is layered onto an L-agar plate. Bacterial colonies to be tested are inoculated onto the nitrocellulose using toothpicks. The inoculated plate is incubated overnight at 37° C. After overnight incubation, the nitrocellulose paper is saturated with 10% SDS in water for 3 min, then saturated with denaturing solution [0.4 M NaOH/10 mM EDTA] for 5 min. After this step, the filters are wetted with neutralizing solution [1M Tris pH 7.0, 1.5M NaCl] two times for five minutes each. After these treatments, the filter is wetted with 2×SSPE [0.3 M NaCl, 20 mM $NaH_2PO_4$, 2 mM EDTA, pH 7.0] for 5 min. The filter is then dried before being baked at 80° C. under vacuum.

For the hybridization reaction, the filters are first wetted for 5 min in 2×SSC [0.3 M NaCl/0.03 M trisodium citrate], then are incubated at 50° C. for 60 min in 3×SSC [0.45 M NaCl, 0.045 M trisodium citrate]/1% SDS, with 4× Denhardt solution added [where 100× Denhardt solution comprises 2% Ficoll 400, 2% polyvinylpyrrolidone, and 20 g/L Bovine serum albumin]. 100 ug/ml denatured salmon sperm DNA is added. For hybridization, 25 ng of probe fragment (the PCR product described above in this section are purified by agarose gel electrophoresis using low melting temperature agarose, and extraction from the gel by dissolving the gel slice at 70° C. for one hr; the DNA is then labeled by random priming with $^{32}P$ d-CTP by using a commercially available labeling kit (Pharmacia Biotech, Piscataway, N.J.). Unincorporated nucleotides are removed by passage through Sephadex G50 micro-columns (Pharmacia Biotech). The radiolabeled probe fragment is then added directly to the blot already in hybridization mix above. The blot is left to hybridize at 65° C. overnight, after which time, the blot is washed three times with 0.1×SSC/0.1% SDS at 65° C., and exposed to x-ray film at −80° C. overnight. Strains that had been characterized in previous studies were used as controls. A darkening of the film in the area of an *E. Coli* colony is interpreted as a positive test, thereby diagnosing an EAEC infection in the patient from whom the *E. Coli* was isolated.

Immunogenic Composition

Although an immunogenic composition is described below with respect to Aap, an immunogenic composition using any of the other proteins described herein is made in a like manner.

An immunogenic composition can be made using Aap by administering the purified protein by injection along with an adjuvant. One such adjuvant used in animals and humans is aluminum hydroxide (alum). One milligram of aluminum hydroxide is mixed with 50 mcg of protein antigen in 1 ml of 0.9% saline and the mixture vortexed then incubated at room temperature for 20 min. The mixture is centrifuged at 10,000×g for 10 min. The supernatant is withdrawn and saved at 4° C. To test immunogenicity, the mixture can be injected subcutaneously into rabbits in two 0.5 ml injections. For human injection, the preparation would be made in exactly the same way, but under the conditions of Good Manufacturing Practices. The antigen could be injected intramuscularly to humans as a subunit vaccine.

Nucleotide Immunogenic Compositions

Although an immunogenic composition is described below with respect to aap, an immunogenic composition using any of the other genes described herein is made in a like manner.

The aap gene could be delivered as a DNA vaccine to induce antibodies to the Aap protein. The aap gene would be amplified using the primers

```
                                          (SEQ ID NO: 20)
    5'-ACAAGCTTGCAAAAAATTAAGTTTGTTATC-3'
and (SEQ ID NO: 17)
    5'-CGGGATCCAACCCATTCGGTTAGAGC-3';
``` use of these primers results in the incorporation of HindIII and BamHI sites onto the DNA fragment. The PCR product would be digested with these two enzymes by manufacturer's protocols (New England Biolabs) and the fragment would be ligated with vector pcDNA2, previously digested with the same enzymes. The reaction would take place using DNA ligase also from New England Biolabs using manufacturer's suggested protocols. This experiment results in thus placing the aap gene downstream of the CMV promoter of this vector. The ligation mix would be transformed into *E. coli* DH5α, selecting for ampicillin resistance. The plasmid could then be purified by standard alkaline lysis techniques, and would be ready for injection as a DNA vaccine. The DNA would be dissolved in endotoxin-free PBS at a concentration of 1 mg/ml. 50 μl of this suspension could be injected into mouse thigh muscle to test immunogenicity. Approximately 1 ml would serve as a human dose.

EAEC Vaccine

The Aap protein could also serve as an effective vaccine for EAEC infection. It has been shown that the Aap protein is secreted outside of the bacterial cell and that inhibition of the function of the protein (by mutagenesis of the gene) changes the ability of the bacterium to penetrate a mucous layer and also changes the morphology of interaction with the intestinal mucosa. For this reason, it is inferred that Aap is a virulence factor and that the presence of antibodies against the protein will interfere with the pathogenic process. Thus, expression of the Aap protein could serve as a useful component of an EAEC vaccine.

The Aap protein could be expressed as part of a vaccine by engineering expression of the protein in a vaccine delivery vector. Most gram negative vaccine vectors could probably be successfully engineered to accomplish this. One example of this technology would be to introduce the pAap plasmid into vector vaccine strain CVD 1204 (U.S. Pat. No. 5,783,196, issued to Noreiga et al. on Jul. 21, 1998). CVD 1204 is an attenuated *Shigella* vector vaccine which colonizes the colonic mucosa and induces an antibody response to both *Shigella* surface antigens and foreign proteins expressed on the bacterial cell surface, including enterotoxigenic *E. coli* fimbrial proteins (Altboum et al., *Infect Immun* 69:3150-8 (2001)). The pAap plasmid would be introduced by electroporation using the method described above in the section "Isolation and Purification of Aap protein and generation of antibodies". The vaccine could then be administered orally as described in the literature (Kotloff et al., *Infect Immun* 68:1034-9 (2000)) and an antibody response could be detected by Western immunoblots using the methods described above.

Another example of this technology would be to PCR amplified the aap gene from strain 042 using upstream and downstream primers incorporating BamHI (upstream primer) and NheI (downstream primer) sites. After PCR, the fragment would be purified from an agarose gel and digested with BamHI and NheI. Expression vector pSEC 10 would be digested with the restriction enzymes BamHI and NheI, generating two fragments. The larger fragment would be isolated from an agarose gel and ligated with the aap PCR fragment previously digested with BamHI and NheI. Digestion and ligation protocols are as described in Ausubel et al, Current Protocols in Molecular Biology. The ligation mix would then be electroporated into competent *Shigella flexneri* vaccine vector strain CVD 1204. Transformants would be selected on kanamycin containing agar and the plasmid verified by digestion with BamHI and NheI.

The aap expression plasmid in CVD 1204 would comprise an aap-expressing attenuated *Shigella* strain, which would be expected to express Aap on its surface. This would be verified by Western blot using the methods described above. 10 ml of L-broth would be inoculated with the Aap-expressing pSEC 10 clone and permitted to grow overnight. After this period, the cells would be precipitated by centrifugation and washed for 10 min in 500 mcl 0.1% Triton X-100 detergent to remove surface localized Aap protein. 20 mcl of this detergent wash would be applied to an SDS-PAGE gel, and subjected to electrophoresis. The gel would be transferred to nitrocellulose and subjected to Western immunoblot using anti-Aap antiserum as above.

The amplified aap would include its signal sequence, which would mediate secretion into the periplasm. Although Aap appears to have a dedicated secretion system (Aat), it has been shown that there is residual translocation to the bacterial cell surface even in the absence of Aat. Therefore, the expression of Aap alone may be sufficient to establish export.

aat Vaccine

The AatA protein could also serve as an effective vaccine for EAEC infection. We have shown that the AatA protein is secreted to the outer membrane of the bacterial cell and appears to be able to do so in the absence of other genes. Therefore, the AatA protein could be expressed as part of a vaccine by engineering expression of the protein in a vaccine delivery vector without additional proteins. aat can be introduced into an attenuated EAEC, *Salmonella, Shigella, Lactobacillus*, or other bacteria. The bacteria is then administered to an animal to generate an immune response to Aat.

The aatA gene would be PCR amplified from strain 042 using upstream and downstream primers incorporating BamHI (upstream primer) and NheI (downstream primer) sites. After PCR, the fragment would be purified from an agarose gel and digested with BamHI and NheI. Expression vector pSEC10 would be digested with the restriction enzymes BamHI and NheI, generating two fragments. The larger fragment would be isolated from an agarose gel and ligated with the aatA PCR fragment previously digested with BamHI and NheI. Digestion, ligation and transformation/electroporation protocols are as described (Sambrook and Russell, Molecular Cloning: A Laboratory Manual. Cold Spring Harbor Laboratory Press, 2001). The ligation mix would then be electroporated into competent *Shigella flexneri* vaccine vector strain CVD 1204. Transformants would be selected on kanamycin containing agar and the plasmid verified by digestion with BamHI and NheI.

The aatA expression plasmid in CVD 1204 would comprise an aa/A-expressing attenuated *Shigella* strain, which would be expected to express AatA on its surface (inserted in the outer membrane). This would be verified by Western blot using standard methods (Harlowe and Lane, Antibodies: A Laboratory Manual. Cold Spring Harbor Laboratory Press, 1988). 10 ml of L-broth would be inoculated with the AatA-expressing pSEC10 clone and permitted to grow overnight. After this period, the cells would be precipitated by centrifugation and Triton X-100 added to the supernatant to a final concentration of 2%. The preparation is centrifuged at 20,000×g for 15 minutes and the pellet applied to an SDS-PAGE gel, then subjected to electrophoresis. The gel would be transferred to nitrocellulose and subjected to Western immunoblot using anti-AatA antiserum.

When expressed in an attenuated *Shigella* strain, such as described above, guinea pigs, anesthetized subcutaneously with ketamine HCl(40 mg/kg) and xylazine (5 mg/kg), are inoculated by intranasal administration twice on days 0 and 14, with ~$2\times10^9$ bacteria (0.1 ml of $400D_{600}$ nm) of the *Shigella* AatA strain that had been propagated on TSA/Congo red /guanine containing plates and harvested in PBS. Sera were obtained on days 0, 14 and 30 by anterior vena cava puncture of anesthetized animals. The immunized animals were tested for bacterial agglutination, immunoblotting, and inhibition of hemagglutination and adherence of Aat expressing strains to Caco-2 cells. The animals would be tested for immune response to AatA by Western blot as described above. This group of animals would then be challenged orally with $10^9$ cfu of strain 042; a second group of control animals not immunized would also be challenged with 042. Stool samples from all animals would be screened for shedding of EAEC by colony hybridization for aap as described above. The presence of bacteria containing aap indicated an EAEC infection.

Mechanism of Action and Importance

It has been shown that enteric pathogens must adhere to the epithelial surface to effect efficient colonization. (Nataro et al., *Clin Microbiol Reviews* January;11(1):142-201 (1998)). However, it may be important to modulate that adherence to permit improved spread across the epithelial surface. Knutton, et al., *Molecular Microbiology* 33: 499-509 (1999), have shown that the bundle-forming pilus (BFP) of EPEC serves both aggregate formation and detachment roles, which occur sequentially. In this way, EPEC can adhere and multiply early in the pathogenetic sequence, establishing a foothold on the epithelium, but can then "shake loose" individual progeny that are free to establish new foci of infection on the mucosa at some distance. This paradigm is intuitively beneficial for the bacteria, and therefore may be a property of many other mucosal pathogens. Indeed, Benitez, et al. have suggested that the Hap mucinase of *Vibrio cholerae* may serve as an enzymatic "detachase", the mutation of which results in increased density of bacterial colonization but also attenuation of virulence. (*Infection and Immunity* 69:6549-53

(2001)). Similarly, the highly conserved Aap protein of EAEC may serve as a modulator of adherence and colonization in EAEC.

Aap is secreted from the bacterial cell and is present free from the cell in the extracellular environment. This evidence suggests that Aap works in a unique fashion. Aap is more hydrophilic than AAF/II, and thus its presence outside the cell mitigates the high surface hydrophobicity conferred by the expression of the AAF fimbriae. Aap may also possess enzymatic activity as well, but in this case, the substrate would need to be of bacterial origin because Aap effects are illustrated only in a cell-free in vitro system. An alternative embodiment is that Aap binds to the bacterial outer membrane or to the AAF fimbriae themselves, thereby modulating the biophysical characteristics of the bacterial cell. However, Aap does not bind to any cellular component. In another embodiment, Aap suppresses the expression of the AAF fimbriae at a post-translational level.

Aap plays a role in the penetration of the mucosal mucous blanket, perhaps through a lessening of particle size. Indeed, as demonstrated in a purified mucin gel column assay, Aap mutants penetrated more slowly than the wild type parent (see above). Thus, moderation of EAEC aggregates could serve to promote penetration of the mucus blanket, and/or promote the dissemination of the organism across the mucosal surface.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

Having thus described the invention, what is claimed is:

1. An isolated polynucleotide molecule having at least 95% sequence identity to nucleotides 1 to 1239 of SEQ ID NO:10.

2. An isolated polynucleotide molecule encoding a polypeptide having at least 95% sequence identity to amino acids 1 to 412 of SEQ ID NO:5.

3. An expression vector comprising an isolated polynucleotide molecule according to claim 1.

4. An expression vector comprising an isolated polynucleotide molecule according to claim 2.

5. A isolated host cell comprising an expression vector of claim 3.

6. A isolated host cell comprising an expression vector of claim 4.

7. A method of preparing a polypeptide encoded by a polynucleotide having at least 95% sequence identity to nucleotides 1 to 1239 of SEQ ID NO:10, comprising culturing the host cell of claim 5 under conditions promoting the expression of said polypeptide and recovering said polypeptide from the cell culture.

8. A method of preparing a polypeptide having at least 95% sequence identity to amino acids 1 to 412 of SEQ ID NO:5, comprising culturing the host cell of claim 6 under conditions promoting the expression of said polypeptide and recovering said polypeptide from the cell culture.

9. A composition comprising a pharmaceutically acceptable carrier and an expression vector according to claim 3 or 4.

10. The composition of claim 9, wherein said composition is in the form of a composition suitable for administration by a route selected from the group consisting of oral administration, nasal administration, inhalation, ophthalmic administration, rectal administration and vaginal administration.

11. A method of generating an antibody response in an animal comprising administering a composition according to claim 9 to said animal.

12. A composition comprising a pharmaceutically acceptable carrier and an isolated host cell according to claim 5 or 6.

13. The composition of claim 12, wherein said composition is in the form of a composition suitable for administration by a route selected from the group consisting of oral administration, nasal administration, inhalation, ophthalmic administration, rectal administration and vaginal administration.

14. A method of generating an antibody response in an animal comprising administering a composition according to claim 12 to said animal.

15. A composition comprising a pharmaceutically acceptable carrier and an isolated host cell, wherein said host cell comprises an expression vector comprising:

(i) an isolated polynucleotide molecule comprising nucleotides 1-1239 of SEQ ID NO:10; or
(ii) an isolated polynucleotide molecule encoding amino acids 1 to 412 of SEQ ID NO:5.

16. The composition of claim 15, wherein said composition is in the form of a composition suitable for administration by a route selected from the group consisting of oral administration, nasal administration, inhalation, ophthalmic administration, rectal administration and vaginal administration.

17. A method of generating an antibody response in an animal comprising administering a composition according to claim 15 to said animal.

* * * * *

```
                          SEQUENCE LISTING

<160> NUMBER OF SEQ ID NOS: 41

<210> SEQ ID NO 1
<211> LENGTH: 348
<212> TYPE: DNA
<213> ORGANISM: Escherichia coli

<400> SEQUENCE: 1
atgaaaaaaa ttaagtttgt tatctttct ggcatcttgg gtatcagcct gaatgctttt      60
gcgggtggta gcggttggaa cgcagataat gtggacccgt cccaatgtat aaaacagtct     120
ggagtacagt atacttataa cagcggtgtc tcagtatgta tgcaaggcct taatgaaggg     180
aaagtaaggg gggtgtctgt ctctggggta ttttattata atgatggcac aacaagcaac     240
ttcaaagggg ttgttacccc ctccacacct gtaaatacga accaagacat taacaagaca     300
aataaggttg gagtccaaaa atatcgtgct ctaaccgaat gggttaaa                  348

<210> SEQ ID NO 2
<211> LENGTH: 116
<212> TYPE: PRT
<213> ORGANISM: Escherichia coli

<400> SEQUENCE: 2

Met Lys Lys Ile Lys Phe Val Ile Phe Ser Gly Ile Leu Gly Ile Ser
1               5                   10                  15

Leu Asn Ala Phe Ala Gly Gly Ser Gly Trp Asn Ala Asp Asn Val Asp
                20                  25                  30

Pro Ser Gln Cys Ile Lys Gln Ser Gly Val Gln Tyr Thr Tyr Asn Ser
            35                  40                  45

Gly Val Ser Val Cys Met Gln Gly Leu Asn Glu Gly Lys Val Arg Gly
        50                  55                  60

Val Ser Val Ser Gly Val Phe Tyr Tyr Asn Asp Gly Thr Thr Ser Asn
65                  70                  75                  80

Phe Lys Gly Val Val Thr Pro Ser Thr Pro Val Asn Thr Asn Gln Asp
                85                  90                  95

Ile Asn Lys Thr Asn Lys Val Gly Val Gln Lys Tyr Arg Ala Leu Thr
            100                 105                 110

Glu Trp Val Lys
        115
```

```
<210> SEQ ID NO 3
<211> LENGTH: 7000
<212> TYPE: DNA
<213> ORGANISM: Escherichia coli

<400> SEQUENCE: 3
gagacgtttg gaggtgtatg ggagccgcgt tatccgcagg agcttcataa ggtgattcat        60
acgaccatac cattgaatcg ctgaacagtg tgatccgtca ctcaatcaag aaacacaggg       120
tgttaccgat agatgagtta gtaaaaagcg gtgtcatcca ggtagcgtta cagaaatggg       180 ccataccect gaagggatgt catcatggcg atgagtcgct ttcttatcaa tgacatccat       240
agtgtcatta taataacgac atttatgcat gccattgaca ttgtcagata ctatatttat       300
gaccaagaac tccatgcagg tccattgcta ttgatatcct cctgagcctc ccgtacaata       360
tcttttatta ggcttaaatc catatttgag gctattttga ttatattatc aaaatcagca       420
tctattacac atgtaactat atcaatcatt atacacctcc ttttctaaa cttttacatg        480 ctaaaacaaa ataaatcaaa aatagatat tattatagca atagttgatt gctgttctaa        540
ctgaacgcca cgttcaacaa cctgtttgac agcttcaact ttaaactcct caggataaag       600
cttaccatgg gaatatctac ggcagcaggc cagtaatgga ttaagtgata acaggtgtct       660
ggaaatatag gggcaaatcc accgaccccg tactgctcac gcagcttatc caactgtggt       720
atcatttttt ccagaggcgg tcgaacctcg ccttcgcaaa ataagcggaa gcctggcgaa       780
ggatatcgtt actgcggcgc agttcacgat tttcacgctc cagctctttc agacgctgac       840
gttcagcagt ggtgagcccg ccwtcaccgc ccccggtatc ccgctcatgc tggcgaaccc       900
agacacgcag agtctccggt gtacagccaa tctttggggc aatggaacaa attaccgccc       960
attgtgagtc atattcgccc tgactttcca gaaccatacg aatcgccctc tgacggactt      1020
cgggggaaaa cgagtatttt tagtcatcct gtttacctct ttctctggaa gtttagtctc      1080
caggatttcc gggatggttc agtttacgta tgttttggct ggttgatact gttttgtca      1140 tgtgagtcac ctctgactga gagtctactc atttagccgc gtgtccacta ttgctgggta      1200
agatcaaatc attaatatct ctgcataacg tgcaggagat gctccatagc attaactaca      1260
tatatttata ctaagtttag tcacacagat ttcgattatt atcataaact tatagttata      1320
tatcccttag ttattaatag ttgggtacat tatatagtgt ttccaataac tgtacatgtc      1380
tactcctgta agtgtggctg aggattcttg ggttatcatt caacatgaca actttgcact      1440
attatctaaa tgaggcgctc cttaatatca tagaaaatag aaggcagaat tttgcatttc      1500 ttgtttttt atctcttagc tttataggga taattattac tgactctttg atatacagtg      1560
tttccttaaa agccgaagaa gaactaaaag ttcatagtga caagtaata tttgtcaaat       1620 tatatcgacc taaaacggta ggatatataa cggaaaaatt cattacggtt agtaaagttc      1680
tttctttctc gaagagcgca ttcctctatg tcagcgatac accttttcc ggtgaactat       1740 tttcggtgaa cggaattgac aagctgggat taaatacgga atattcgggg gatttaaatg      1800
ataagtacaa tggcaatgtt gctattgtta atgaatctag tccgttttc agtaagaaac       1860 aaatatttat taatggtgtt ccgtttaaaa ttattggtgt ccgattaaac tcaaaaacgg      1920
attttcttga cagccttgga ttgaaagcaa gccaatcaga tgaacacatt tttattccac      1980
tggaaactat gtttaaagtg aaactcgata acagagtcaa tgctgttaaa atctttcttg      2040
ataacatagt aacaaagaga gatataaaca acgtaaagag agttttatat gacaatgata      2100
taagaaaatt cgatattgtc acatcttaa acgccaagga agctgtggac agagtgttag       2160
```

```
agaggttttc attactcact aactctgttt acgtgatatt aactctgtct gcgtccgtga    2220
catgttttat tttatcgaaa cgcagttttt attcgagacg ggtagagtta tcattaaaaa    2280
taatccatgg tacagaaaag aaagagatta cagttctaat tatcattgag tctttaataa    2340
tgctgagcgt atgtcttttt atttcagtca tctatgcagg agtaataatg catattatta    2400 agtattttt agatgtaaca ataagtatta ggacaacaat gattacaata tcacttgcca    2460
atgtcctatt ggtatttata tctgcaaata tcattttcgg caggctattt ttcagtataa    2520
accctgttaa tgcaataaaa ggaaagatcg agtgagacac atattatact catttcttgc    2580
aataaatgct tatctgtttt cgacacagac tctggcaaaa gactgtatca ttgataattt    2640
ctttcagaaa agcatccagt ttaattctta ttctcttgat atcgaagagt tggatattaa    2700
taaacataac aatataaaaa cgatgttacc agatataaat ataggggttag ggcagtatat    2760 aaacaacaat cagtggttct catctattac agacagcaat ttttatttat cattatccta    2820
taatcttcta tcggcttatg aagcaaaaat gcagaatgaa aaattggata ttgctaatta    2880
tttaaaatat attgaaatgc ttagtgagag aaacaactat ataattaatt tgttctcgga    2940
aatcattaac tataagataa aaaaatctca cctgatgttg atgctcgaga gatatagaaa    3000
gcttaataaa gaatacgaaa ttgcaaagcg taaaatgtca attggattaa tatctgttct    3060
tgatgtagag atgagatata atatattaca aaaaatcagg tttgatattg atgtacttga    3120
ggaggaggaa agtttactgt cagataaaat ctcgagagaa tatcatgttc cagagagtgc    3180
aatcccagac attacatatc ataaattaaa agagtgtaaa acagcggatt tctatacatt    3240
attagctgaa aacaaaaaac tcaagattaa ggctgctgat atagataatg atataagaaa    3300
actatcggag atcccatctt tttatttatc atttggatta acacctaaac agggaggtgc    3360
attgggtaat atgagtctca gaaaaatgga ttatagtgct agtctgggta tcagttttcc    3420
tttgatggga ttatttagtt cttcagaaaa tcaaaaagaa aagattattt ctatatctcg    3480
aaccagaaat gaattattga agaaaatat aaaactagat ctgttggaaa aagagattcg    3540
ccagaaaatt gataaattag agaaaaatct tgcgatgatg aaaaatgaac tagctctgaa    3600
aaaaaggaaa attgagtata taaattatcg cgtaaagaat ggacaagacg acgttatcac    3660
ttatttgtct agtgtagaga atttacatga aacagaaaat gaatttcaga aaattggata    3720
tgagattgaa tattatagtt tatatcatta ttttcttctg cagcacattt ccaatacagg    3780
ggaaatgtga taactactat ggtgttctac atggaaataa aaacgtaaaa tataagagtc    3840
cttttgcagg ggttgtaata cttgaggaca tgattgaagg taatgtggtc actgtggaaa    3900
ggaagctatt ttctgtcctg aatcatgagt atactgcaaa gaaagatatt gtggccatga    3960
aaagaaatat ggaagagaaa aaactatcta gattaaaagg agcaaagata catttaacct    4020
ctatgttctc aaaagggtta atttcaagag aaagcttgca tgatatagat gagaaaatca    4080
gcaatactga attgactatt atgggactgg acatagagtc aaagaatctg gaacaactat    4140
taaagttgtc atcaccattt ttgcatactc ctttcattat tcgaaatatc ttcgtaacaa    4200
atgagcagta tgtaaatgca ggcgatgata taatgtctgt agaacttctg gataattttt    4260
atatagatgt taaattcgat ccggtcagta taacaggaaa tataagagac aagagaataa    4320
ggtatcgttc tttggttaat tctctaatgg ggtctgcaac agtagtcaaa aatatccgtg    4380 ccagtgggaga atcaactcaa ggtgaagata catcaggtct gcgctctatt acgctgttaa    4440
ttgatgggga ccggaatgaa ttgtcgaatc tattagatac tgcgtttgag attataatag    4500
atgattagag taaaaataca taaaaaacct atagaaaaca gaactatcct gaataatagc    4560
```

```
actattgaga taaaagaggg atcgttcaat attattactg gcccgtctgg agttggaaag    4620
acttcactgc ttaacattat tggtctatta gataatgcct tgttggaga gtatgaactt     4680 ttcggtaaaa aagtggaaat aaaagataat agcatcacta catatatcag aagaaaatat    4740
tttggattca tctttcagga ttctctgatt aatgtaaagc aaaatgtctt aagaaatata    4800
ctatgttctg tagattctca aaacataata gccgcaaggg aaagaattaa tgaagtcttg    4860
gtgtctgttg gattgtcaaa tattaataat aatgtatcat ttctctccgg gggagaaaaa    4920
caaagactag cacttgctag ggcattgata aaaaaaccca gtactttt agcagatgaa     4980 cctactgcta gtctagatat aaagaataaa aaattagtga tgaatatact atctgaatac    5040
aataatcaag gaggaacagt cgttatggta actcatgatc ttgaactaat cgatgagaat    5100
atgactttaa tccaactatt aaatacatag gcttacagtt tatgaaattc gctattgtct    5160
tattgtattt ttttgcctat tatcttgcag caagaaaaag acgagtgagt cttttttta   5220 ctattctttt atactctatc attttctctg ggatgtattt ttctagtggt tttttagaat    5280
attatggcag ttctaattta tacctttcat ttggattact ctgctataat atgataaccc    5340
ttgtcatata tggtttcctg agttcttatg ggttacttgg agcatgtcta catgcacttt    5400
cattaacctc attatccgcc ttcgggatgt ttataccatt aaatccattg attgttttat    5460
attatgattt tcctagcatc ttaccaagaa cagatattcc tgttttaaat ttattaatat    5520
taaatcttat tcctgcagtt acatttagtc taaaaatatc attttttctc cgttctctta    5580
tattattatt gttatttccg ctaatatgga aaacgccggt taatataact catccccctc    5640
tgaacattgt gattgtacag gttggccttt attttaaaaa agtaggtgtc agaggtaatt    5700
tttatacgga tctcaatgag ttcgtcagaa ataagaaggt tgatctaatt attctctcag    5760
aaaatgtttt tttcggttac aagaatgatt atataaagga agaactaaa catctcttaa    5820 agcaattaaa agataatcga ctccactaca aatatgggat attaatgaat ctttatggat    5880
atcaagacat taataacgta gtgtctgctt tctggcataa agaagaattt cttctccacc    5940
aaaaaagcaa attgatacct tttttgaga agaaaagttt ttataactca ccagaaccat    6000
cgacatcacc ttttctatat tataaaaaga aatataatga gcaggacatc ctggatttca    6060
acaacattaa aatgagtatt catatatgtt atgagggatt attccctgag ggtgaatctc    6120
gaagaaaaga tatctccatt gttcaatccg attattcatg gttgagtgac aatcacaaat    6180
atgacaacac ccttattaat ggaagtatat tatcgaaatt ctctgtttcg ccgaacactc    6240
ctcttattaa tattcaaaat tatggtggga cagtttttat agacaataat tggaaaattg    6300
atatggactt atttaatagg tcaaaaacgg aaccttttt atttacacag atatgagtaa    6360
tgcactaact ttcagttgaa aatagaagtg ctattatatt aactaatgta tagggaaatt    6420
tttagagata attaaagtaa atattggcgt tgaacaataa cgctaatatc gaggtgaata    6480
tgatttgctg actggcaata taacgaaaga ttaaaactct ctgaaaagag agtttatcat    6540
tagtatggcc acatagaagt tatgtcatag caatataaaa tagctttat tagctttaa    6600 aataaaatcc tgatgaatat aagtaagcgg ctcgtcagaa ccgtattgat atttactgag    6660
agctcagatc aactttccaa ggcaacagat cgcgtacccg gtttgtcggc cagtcctgga    6720
tatgctcaat gacgtaacgc agtcattttt ctggctccac attgttcaga cggcatgtgc    6780
cgatcagcga gtacaacacc gccgcatgtt cgccaccgct gtcggaaccc gcgaacagcc    6840
agtttttccg gcctacagct actccccgta aggcgttctc tgtaatgttg ttgtcgattt    6900
```

```
ccacccagcc atcgttcgca tagtacgtca gtgccggcca ctggttaagt gcgtacgcga    6960
acgccttcgc caactctgag tgtcgtgaca gggtcttcat                          7000
```

<210> SEQ ID NO 4
<211> LENGTH: 376
<212> TYPE: PRT
<213> ORGANISM: Escherichia coli

<400> SEQUENCE: 4

```
Met Thr Thr Leu His Tyr Tyr Leu Asn Glu Ala Leu Leu Asn Ile Ile
1               5                   10                  15

Glu Asn Arg Arg Gln Asn Phe Ala Phe Leu Val Phe Leu Ser Leu Ser
            20                  25                  30

Phe Ile Gly Ile Ile Ile Thr Asp Ser Leu Ile Tyr Ser Val Ser Leu
        35                  40                  45

Lys Ala Glu Glu Glu Leu Lys Val His Ser Asp Lys Val Ile Phe Val
    50                  55                  60

Lys Leu Tyr Arg Pro Lys Thr Val Gly Tyr Ile Thr Glu Lys Phe Ile
65                  70                  75                  80

Thr Val Ser Lys Val Leu Ser Phe Ser Lys Ser Ala Phe Leu Tyr Val
                85                  90                  95

Ser Asp Thr Pro Phe Ser Gly Glu Leu Phe Ser Val Asn Gly Ile Asp
            100                 105                 110

Lys Leu Gly Leu Asn Thr Glu Tyr Ser Gly Asp Leu Asn Asp Lys Tyr
        115                 120                 125

Asn Gly Asn Val Ala Ile Val Asn Glu Ser Ser Pro Phe Phe Ser Lys
    130                 135                 140

Lys Gln Ile Phe Ile Asn Gly Val Pro Phe Lys Ile Ile Gly Val Arg
145                 150                 155                 160

Leu Asn Ser Lys Thr Asp Phe Leu Asp Ser Leu Gly Leu Lys Ala Ser
                165                 170                 175

Gln Ser Asp Glu His Ile Phe Ile Pro Leu Glu Thr Met Phe Lys Val
            180                 185                 190

Lys Leu Asp Asn Arg Val Asn Ala Val Lys Ile Phe Leu Asp Asn Ile
        195                 200                 205

Val Thr Lys Arg Asp Ile Asn Asn Val Lys Arg Val Leu Tyr Asp Asn
    210                 215                 220

Asp Ile Arg Lys Phe Asp Ile Val Thr Ser Leu Asn Ala Lys Glu Ala
225                 230                 235                 240

Val Asp Arg Val Leu Glu Arg Phe Ser Leu Leu Thr Asn Ser Val Tyr
                245                 250                 255

Val Ile Leu Thr Leu Ser Ala Ser Val Thr Cys Phe Ile Leu Ser Lys
            260                 265                 270

Arg Ser Phe Tyr Ser Arg Arg Val Glu Leu Ser Leu Lys Ile Ile His
        275                 280                 285

Gly Thr Glu Lys Lys Glu Ile Thr Val Leu Ile Ile Glu Ser Leu
    290                 295                 300

Ile Met Leu Ser Val Cys Leu Phe Ile Ser Val Ile Tyr Ala Gly Val
305                 310                 315                 320

Ile Met His Ile Ile Lys Tyr Phe Leu Asp Val Thr Ile Ser Ile Arg
                325                 330                 335

Thr Thr Met Ile Thr Ile Ser Leu Ala Asn Val Leu Leu Val Phe Ile
            340                 345                 350
```

Ser Ala Asn Ile Ile Phe Gly Arg Leu Phe Phe Ser Ile Asn Pro Val
            355                 360                 365

Asn Ala Ile Lys Gly Lys Ile Glu
        370                 375

<210> SEQ ID NO 5
<211> LENGTH: 412
<212> TYPE: PRT
<213> ORGANISM: Escherichia coli

<400> SEQUENCE: 5

Val Arg His Ile Leu Tyr Ser Phe Leu Ala Ile Asn Ala Tyr Leu Phe
1               5                   10                  15

Ser Thr Gln Thr Leu Ala Lys Asp Cys Ile Ile Asp Asn Phe Phe Gln
            20                  25                  30

Lys Ser Ile Gln Phe Asn Ser Tyr Ser Leu Asp Ile Glu Glu Leu Asp
        35                  40                  45

Ile Asn Lys His Asn Asn Ile Lys Thr Met Leu Pro Asp Ile Asn Ile
    50                  55                  60

Gly Leu Gly Gln Tyr Ile Asn Asn Gln Trp Phe Ser Ser Ile Thr
65                  70                  75                  80

Asp Ser Asn Phe Tyr Leu Ser Leu Ser Tyr Asn Leu Leu Ser Ala Tyr
                85                  90                  95

Glu Ala Lys Met Gln Asn Asp Lys Leu Asp Ile Ala Asn Tyr Leu Lys
            100                 105                 110

Tyr Ile Glu Met Leu Ser Glu Arg Asn Asn Tyr Ile Ile Asn Leu Phe
        115                 120                 125

Ser Glu Ile Ile Asn Tyr Lys Ile Lys Lys Ser His Leu Met Leu Met
    130                 135                 140

Leu Glu Arg Tyr Arg Lys Leu Asn Lys Glu Tyr Glu Ile Ala Lys Arg
145                 150                 155                 160

Lys Met Ser Ile Gly Leu Ile Ser Val Leu Asp Val Glu Met Arg Tyr
                165                 170                 175

Asn Ile Leu Gln Lys Ile Arg Phe Asp Ile Asp Val Leu Glu Glu Glu
            180                 185                 190

Glu Ser Leu Leu Ser Asp Lys Ile Ser Arg Glu Tyr His Val Pro Glu
        195                 200                 205

Ser Ala Ile Pro Asp Ile Thr Tyr His Lys Leu Lys Glu Cys Lys Thr
    210                 215                 220

Ala Asp Phe Tyr Thr Leu Leu Ala Glu Asn Lys Lys Leu Lys Ile Lys
225                 230                 235                 240

Ala Ala Asp Ile Asp Asn Asp Ile Arg Lys Leu Ser Glu Ile Pro Ser
                245                 250                 255

Phe Tyr Leu Ser Phe Gly Leu Thr Pro Lys Gln Gly Gly Ala Leu Gly
            260                 265                 270

Asn Met Ser Leu Arg Lys Met Asp Tyr Ser Ala Ser Leu Gly Ile Ser
        275                 280                 285

Phe Pro Leu Met Gly Leu Phe Ser Ser Ser Glu Asn Gln Lys Glu Lys
    290                 295                 300

Ile Ile Ser Ile Ser Arg Thr Arg Asn Glu Leu Leu Lys Glu Asn Ile
305                 310                 315                 320

Lys Leu Asp Leu Leu Glu Lys Glu Ile Arg Gln Lys Ile Asp Lys Leu
                325                 330                 335

Glu Lys Asn Leu Ala Met Met Lys Asn Glu Leu Ala Leu Lys Lys Arg
            340                 345                 350

```
Lys Ile Glu Tyr Ile Asn Tyr Arg Val Lys Asn Gly Gln Asp Val
            355                 360                 365

Ile Thr Tyr Leu Ser Ser Val Glu Asn Leu His Glu Thr Glu Asn Glu
370                 375                 380

Phe Gln Lys Ile Gly Tyr Glu Ile Glu Tyr Tyr Ser Leu Tyr His Tyr
385                 390                 395                 400

Phe Leu Leu Gln His Ile Ser Asn Thr Gly Glu Met
            405                 410

<210> SEQ ID NO 6
<211> LENGTH: 273
<212> TYPE: PRT
<213> ORGANISM: Escherichia coli

<400> SEQUENCE: 6

Met Lys Gln Lys Met Asn Phe Arg Lys Leu Asp Met Arg Leu Asn Ile
1               5                   10                  15

Ile Val Tyr Ile Ile Phe Phe Cys Ser Thr Phe Pro Ile Gln Gly
            20                  25                  30

Lys Cys Asp Asn Tyr Tyr Gly Val Leu His Gly Asn Lys Asn Val Lys
            35                  40                  45

Tyr Lys Ser Pro Phe Ala Gly Val Val Ile Leu Glu Asp Met Ile Glu
50                  55                  60

Gly Asn Val Val Thr Val Glu Arg Lys Leu Phe Ser Val Leu Asn His
65                  70                  75                  80

Glu Tyr Thr Ala Lys Lys Asp Ile Val Ala Met Lys Arg Asn Met Glu
                85                  90                  95

Glu Lys Lys Leu Ser Arg Leu Lys Gly Ala Lys Ile His Leu Thr Ser
            100                 105                 110

Met Phe Ser Lys Gly Leu Ile Ser Arg Glu Ser Leu His Asp Ile Asp
            115                 120                 125

Glu Lys Ile Ser Asn Thr Glu Leu Thr Ile Met Gly Leu Asp Ile Glu
            130                 135                 140

Ser Lys Asn Leu Glu Gln Leu Leu Lys Leu Ser Ser Pro Phe Leu His
145                 150                 155                 160

Thr Pro Phe Ile Ile Arg Asn Ile Phe Val Thr Asn Glu Gln Tyr Val
                165                 170                 175

Asn Ala Gly Asp Asp Ile Met Ser Val Glu Leu Leu Asp Asn Phe Tyr
            180                 185                 190

Ile Asp Val Lys Phe Asp Pro Val Ser Ile Thr Gly Asn Ile Arg Asp
            195                 200                 205

Lys Arg Ile Arg Tyr Arg Ser Leu Val Asn Ser Leu Met Gly Ser Ala
210                 215                 220

Thr Val Val Lys Asn Ile Arg Ala Ser Gly Glu Ser Thr Gln Gly Glu
225                 230                 235                 240

Asp Thr Ser Gly Leu Arg Ser Ile Thr Leu Leu Ile Asp Gly Asp Arg
                245                 250                 255

Asn Glu Leu Ser Asn Leu Leu Asp Thr Ala Phe Glu Ile Ile Ile Asp
            260                 265                 270

Asp

<210> SEQ ID NO 7
<211> LENGTH: 209
<212> TYPE: PRT
<213> ORGANISM: Escherichia coli
```

<400> SEQUENCE: 7

```
Met Ile Arg Val Lys Ile His Lys Lys Pro Ile Glu Asn Arg Thr Ile
1               5                   10                  15

Leu Asn Asn Ser Thr Ile Glu Ile Lys Glu Gly Ser Phe Asn Ile Ile
            20                  25                  30

Thr Gly Pro Ser Gly Val Gly Lys Thr Ser Leu Leu Asn Ile Ile Gly
        35                  40                  45

Leu Leu Asp Asn Ala Phe Val Gly Glu Tyr Glu Leu Phe Gly Lys Lys
    50                  55                  60

Val Glu Ile Lys Asp Asn Ser Ile Thr Thr Tyr Ile Arg Arg Lys Tyr
65                  70                  75                  80

Phe Gly Phe Ile Phe Gln Asp Ser Leu Ile Asn Val Lys Gln Asn Val
                85                  90                  95

Leu Arg Asn Ile Leu Cys Ser Val Asp Ser Gln Asn Ile Ile Ala Ala
            100                 105                 110

Arg Glu Arg Ile Asn Glu Val Leu Val Ser Val Gly Leu Ser Asn Ile
        115                 120                 125

Asn Asn Asn Val Ser Phe Leu Ser Gly Gly Glu Lys Gln Arg Leu Ala
    130                 135                 140

Leu Ala Arg Ala Leu Ile Lys Lys Pro Ser Ile Leu Leu Ala Asp Glu
145                 150                 155                 160

Pro Thr Ala Ser Leu Asp Ile Lys Asn Lys Lys Leu Val Met Asn Ile
                165                 170                 175

Leu Ser Glu Tyr Asn Asn Gln Gly Gly Thr Val Val Met Val Thr His
            180                 185                 190

Asp Leu Glu Leu Ile Asp Glu Asn Met Thr Leu Ile Gln Leu Leu Asn
        195                 200                 205

Thr
```

<210> SEQ ID NO 8
<211> LENGTH: 404
<212> TYPE: PRT
<213> ORGANISM: Escherichia coli

<400> SEQUENCE: 8

```
Met Lys Phe Ala Ile Val Leu Leu Tyr Phe Phe Ala Tyr Tyr Leu Ala
1               5                   10                  15

Ala Arg Lys Arg Arg Val Ser Leu Phe Phe Thr Ile Leu Leu Tyr Ser
            20                  25                  30

Ile Ile Phe Ser Gly Met Tyr Phe Ser Ser Gly Phe Leu Glu Tyr Tyr
        35                  40                  45

Gly Ser Ser Asn Leu Tyr Leu Ser Phe Gly Leu Leu Cys Tyr Asn Met
    50                  55                  60

Ile Thr Leu Val Ile Tyr Gly Phe Leu Ser Ser Tyr Gly Leu Leu Gly
65                  70                  75                  80

Ala Cys Leu His Ala Leu Ser Leu Thr Ser Leu Ser Ala Phe Gly Met
                85                  90                  95

Phe Ile Pro Leu Asn Pro Leu Ile Val Leu Tyr Tyr Asp Phe Pro Ser
            100                 105                 110

Ile Leu Pro Arg Thr Asp Ile Pro Val Leu Asn Leu Ile Leu Asn
        115                 120                 125

Leu Ile Pro Ala Val Thr Phe Ser Leu Lys Ile Ser Phe Phe Leu Arg
    130                 135                 140
```

```
Ser Leu Ile Leu Leu Leu Phe Pro Leu Ile Trp Lys Thr Pro Val
145                 150                 155                 160

Asn Ile Thr His Pro Pro Leu Asn Ile Val Ile Val Gln Val Gly Leu
            165                 170                 175

Tyr Phe Lys Lys Val Gly Val Arg Gly Asn Phe Tyr Thr Asp Leu Asn
            180                 185                 190

Glu Phe Val Arg Asn Lys Lys Val Asp Leu Ile Ile Leu Ser Glu Asn
        195                 200                 205

Val Phe Phe Gly Tyr Lys Asn Asp Tyr Ile Lys Glu Arg Thr Lys His
    210                 215                 220

Leu Leu Lys Gln Leu Lys Asp Asn Arg Leu His Tyr Lys Tyr Gly Ile
225                 230                 235                 240

Leu Met Asn Leu Tyr Gly Tyr Gln Asp Ile Asn Asn Val Val Ser Ala
            245                 250                 255

Phe Trp His Lys Glu Glu Phe Leu Leu His Gln Lys Ser Lys Leu Ile
            260                 265                 270

Pro Phe Phe Glu Lys Lys Ser Phe Tyr Asn Ser Pro Glu Pro Ser Thr
        275                 280                 285

Ser Pro Phe Leu Tyr Tyr Lys Lys Lys Tyr Asn Glu Gln Asp Ile Leu
    290                 295                 300

Asp Phe Asn Asn Ile Lys Met Ser Ile His Ile Cys Tyr Glu Gly Leu
305                 310                 315                 320

Phe Pro Glu Gly Glu Ser Arg Arg Lys Asp Ile Ser Ile Val Gln Ser
            325                 330                 335

Asp Tyr Ser Trp Leu Ser Asp Asn His Lys Tyr Asp Asn Thr Leu Ile
            340                 345                 350

Asn Gly Ser Ile Leu Ser Lys Phe Ser Val Ser Pro Asn Thr Pro Leu
        355                 360                 365

Ile Asn Ile Gln Asn Tyr Gly Gly Thr Val Phe Ile Asp Asn Asn Trp
    370                 375                 380

Lys Ile Asp Met Asp Leu Phe Asn Arg Ser Lys Thr Glu Pro Phe Leu
385                 390                 395                 400

Phe Thr Gln Ile

<210> SEQ ID NO 9
<211> LENGTH: 1131
<212> TYPE: DNA
<213> ORGANISM: Escherichia coli

<400> SEQUENCE: 9
atgacaactt tgcactatta tctaaatgag gcgctcctta atatcataga aaatagaagg    60
cagaattttg catttcttgt tttttatct cttagcttta tagggataat tattactgac    120
tctttgatat acagtgtttc cttaaaagcc gaagaagaac taaaagttca tagtgacaaa    180
gtaatatttg tcaaattata tcgacctaaa acggtaggat atataacgga aaaattcatt    240
acggttagta agttcttc tttctcgaag agcgcattcc tctatgtcag cgatacacct    300
ttttccggtg aactatttc ggtgaacgga attgacaagc tgggattaaa tacggaatat    360
tcgggggatt taaatgataa gtacaatggc aatgttgcta ttgttaatga atctagtccg    420
ttttcagta gaaacaaat atttattaat ggtgttccgt ttaaaattat tggtgtccga    480
ttaaactcaa aaacggattt tcttgacagc cttggattga agcaagccaa atcagatgaa    540
cacatttta ttccactgga aactatgttt aaagtgaaac tcgataacag agtcaatgct    600
gttaaaatct ttcttgataa catagtaaca aagagagata taaacaacgt aaagagagtt    660
```

```
ttatatgaca atgatataag aaaattcgat attgtcacat ctttaaacgc caaggaagct      720
gtggacagag tgttagagag gttttcatta ctcactaact ctgtttacgt gatattaact      780
ctgtctgcgt ccgtgacatg ttttatttta tcgaaacgca gttttttattc gagacgggta    840 gagttatcat taaaaataat ccatggtaca gaaaagaaag agattacagt tctaattatc     900
attgagtctt taataatgct gagcgtatgt cttttttattt cagtcatcta tgcaggagta    960
ataatgcata ttattaagta ttttttagat gtaacaataa gtattaggac aacaatgatt    1020
acaatatcac ttgccaatgt cctattggta tttatatctg caaatatcat tttcggcagg    1080 ctattttttca gtataaaccc tgttaatgca ataaaaggaa agatcgagtg a            1131
```

<210> SEQ ID NO 10
<211> LENGTH: 1239
<212> TYPE: DNA
<213> ORGANISM: Escherichia coli

<400> SEQUENCE: 10

```
gtgagacaca tattatactc atttcttgca ataaatgctt atctgttttc gacacagact     60
ctggcaaaag actgtatcat tgataatttc tttcagaaaa gcatccagtt taattcttat    120
tctcttgata tcgaagagtt ggatattaat aaacataaca atataaaaac gatgttacca    180
gatataaata taggggttagg gcagtatata acaacaatc agtggttctc atctattaca    240
gacagcaatt tttattatc attatccatat aatcttctat cggcttatga agcaaaaatg    300
cagaatgata aattggatat tgctaattat ttaaaatata ttgaaatgct tagtgagaga    360
aacaactata taattaattt gttctcggaa atcattaact ataagataaa aaaatctcac    420
ctgatgttga tgctcgagag atatagaaag cttaataaag aatacgaaat tgcaaagcgt    480
aaaatgtcaa ttggattaat atctgttctt gatgtagaga tgagatataa tatattacaa    540
aaaatcaggt ttgatattga tgtacttgag gaggaggaaa gtttactgtc agataaaatc    600
tcgagagaat atcatgttcc agagagtgca atcccagaca ttacatatca taaattaaaa    660
gagtgtaaaa cagcggattt ctatacatta ttagctgaaa acaaaaaact caagattaag    720
gctgctgata tagataatga tataagaaaa ctatcggaga tcccatcttt ttatttatca    780
tttggattaa cacctaaaca gggaggtgca ttgggtaata tgagtctcag aaaaatggat    840
tatagtgcta gtctgggtat cagttttcct ttgatgggat tatttagttc ttcagaaaat    900
caaaaagaaa agattatttc tatatctcga accagaaatg aattattgaa agaaaatata    960
aaactagatc tgttggaaaa agagattcgc cagaaaattg ataaattaga gaaaaatctt   1020
gcgatgatga aaaatgaact agctctgaaa aaaggaaaa ttgagtatat aaattatcgc    1080
gtaaagaatg gacaagacga cgttatcact tatttgtcta gtgtagagaa tttacatgaa    1140
acagaaaatg aatttcagaa aattggatat gagattgaat attatagttt atatcattat    1200
tttcttctgc agcacatttc caatacaggg gaaatgtga                           1239
```

<210> SEQ ID NO 11
<211> LENGTH: 822
<212> TYPE: DNA
<213> ORGANISM: Escherichia coli

<400> SEQUENCE: 11

```
atgaaacaga aaatgaattt cagaaaattg gatatgagat tgaatattat agtttatatc     60
attattttct ctgcagcac atttccaata caggggaaat gtgataacta ctatggtgtt    120
ctacatggaa ataaaaacgt aaaatataag agtccttttg caggggttgt aatacttgag   180
```

```
gacatgattg aaggtaatgt ggtcactgtg gaaaggaagc tatttctgt cctgaatcat      240 gagtatactg caaagaaaga tattgtggcc atgaaaagaa atatggaaga gaaaaaacta      300
tctagattaa aaggagcaaa gatacattta acctctatgt tctcaaaagg gttaatttca      360
agagaaagct tgcatgatat agatgagaaa atcagcaata ctgaattgac tattatggga      420
ctggacatag agtcaaagaa tctgaacaa ctattaaagt tgtcatcacc atttttgcat       480
actcctttca ttattcgaaa tatcttcgta acaaatgagc agtatgtaaa tgcaggcgat       540
gatataatgt ctgtagaact tctggataat ttttatatag atgttaaatt cgatccggtc      600
agtataacag gaaatataag agacaagaga ataaggtatc gttctttggt taattctcta      660
atggggtctg caacagtagt caaaaatatc cgtgccagtg gagaatcaac tcaaggtgaa      720
gatacatcag gtctgcgctc tattacgctg ttaattgatg gggaccggaa tgaattgtcg      780
aatctattag atactgcgtt tgagattata atagatgatt ag                         822

<210> SEQ ID NO 12
<211> LENGTH: 630
<212> TYPE: DNA
<213> ORGANISM: Escherichia coli

<400> SEQUENCE: 12
atgattagag taaaaataca taaaaaacct atagaaaaca gaactatcct gaataatagc       60
actattgaga taaaagaggg atcgttcaat attattactg gcccgtctgg agttggaaag      120
acttcactgc ttaacattat tggtctatta gataatgcct tgttggaga gtatgaactt       180 ttcggtaaaa aagtggaaat aaaagataat agcatcacta catatatcag aagaaaatat      240
tttggattca tctttcagga ttctctgatt aatgtaaagc aaaatgtctt aagaaatata      300
ctatgttctg tagattctca aaacataata gccgcaaggg aaagaattaa tgaagtcttg      360
gtgtctgttg gattgtcaaa tattaataat aatgtatcat ttctctccgg gggagaaaaa      420
caaagactag cacttgctag ggcattgata aaaaaaccca gtatacttt agcagatgaa       480 cctactgcta gtctagatat aaagaataaa aaattagtga tgaatatact atctgaatac      540
aataatcaag gaggaacagt cgttatggta actcatgatc ttgaactaat cgatgagaat      600
atgactttaa tccaactatt aaatacatag                                      630

<210> SEQ ID NO 13
<211> LENGTH: 1215
<212> TYPE: DNA
<213> ORGANISM: Escherichia coli

<400> SEQUENCE: 13
atgaaattcg ctattgtctt attgtatttt tttgcctatt atcttgcagc aagaaaaaga       60
cgagtgagtc ttttttttac tattcttta tactctatca ttttctctgg gatgtatttt       120
tctagtggtt tttagaata ttatggcagt tctaatttat acctttcatt tggattactc       180
tgctataata tgataaccct tgtcatatat ggtttcctga gttcttatgg gttacttgga      240
gcatgtctac atgcactttc attaacctca ttatccgcct tcgggatgtt tataccatta      300
aatccattga ttgttttata ttatgatttt cctagcatct taccaagaac agatattcct      360
gttttaaatt tattaatatt aaatcttatt cctgcagtta catttagtct aaaaatatca      420 tttttttctcc gttctcttat attattattg ttatttccgc taatatggaa aacgccggtt      480
aatataactc atcccctct gaacattgtg attgtacagg ttggccttta ttttaaaaaa       540
gtaggtgtca gaggtaattt ttatacggat ctcaatgagt tcgtcagaaa taagaaggtt      600
```

-continued

```
gatctaatta ttctctcaga aaatgttttt ttcggttaca agaatgatta tataaaggaa    660
agaactaaac atctcttaaa gcaattaaaa gataatcgac tccactacaa atatgggata    720
ttaatgaatc tttatggata tcaagacatt aataacgtag tgtctgcttt ctggcataaa    780
gaagaatttc ttctccacca aaaaagcaaa ttgatacctt tttttgagaa gaaaagtttt    840
tataactcac cagaaccatc gacatcacct tttctatatt ataaaagaa atataatgag     900 caggacatcc tggatttcaa caacattaaa atgagtattc atatatgtta tgagggatta    960
ttccctgagg gtgaatctcg aagaaaagat atctccattg ttcaatccga ttattcatgg   1020
ttgagtgaca atcacaaata tgacaacacc cttattaatg gaagtatatt atcgaaattc   1080
tctgtttcgc cgaacactcc tcttattaat attcaaaatt atggtgggac agttttata    1140 gacaataatt ggaaaattga tatggactta tttaataggt caaaaacgga accttttta    1200 tttacacaga tatga                                                    1215

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
atggtacctt gttatctttt ctggcatctt gggt                               34

<210> SEQ ID NO 15
<211> LENGTH: 35
<212> TYPE: DNA
<213> ORGANISM: Artificial Sequence
<220> FEATURE:
<223> OTHER INFORMATION: PCR primer

<400> SEQUENCE: 15
atgagctctg gagggggtaa caacccctttt gaagt                             35

<210> SEQ ID NO 16
<211> LENGTH: 30
<212> TYPE: DNA
<213> ORGANISM: Artificial Sequence
<220> FEATURE:
<223> OTHER INFORMATION: PCR primer

<400> SEQUENCE: 16
acatgcatgc aaaaaattaa gtttgttatc                                    30

<210> SEQ ID NO 17
<211> LENGTH: 26
<212> TYPE: DNA
<213> ORGANISM: Artificial Sequence
<220> FEATURE:
<223> OTHER INFORMATION: PCR primer

<400> SEQUENCE: 17
cgggatccaa cccattcggt tagagc                                        26

<210> SEQ ID NO 18
<211> LENGTH: 30
<212> TYPE: DNA
<213> ORGANISM: Artificial Sequence
<220> FEATURE:
<223> OTHER INFORMATION: PCR primer
```

```
<400> SEQUENCE: 18
acggatccat gttaccagat ataaatatag                                    30

<210> SEQ ID NO 19
<211> LENGTH: 30
<212> TYPE: DNA
<213> ORGANISM: Artificial Sequence
<220> FEATURE:
<223> OTHER INFORMATION: PCR primer

<400> SEQUENCE: 19
acgaattcca tttcccctgt attggaaatg                                    30

<210> SEQ ID NO 20
<211> LENGTH: 26
<212> TYPE: DNA
<213> ORGANISM: Artificial Sequence
<220> FEATURE:
<223> OTHER INFORMATION: PCR primer

<400> SEQUENCE: 20
actctagatg aaatgcttag tgagag                                        26

<210> SEQ ID NO 21
<211> LENGTH: 26
<212> TYPE: DNA
<213> ORGANISM: Artificial Sequence
<220> FEATURE:
<223> OTHER INFORMATION: PCR primer

<400> SEQUENCE: 21
acgaattcga tacccagact agcact                                        26

<210> SEQ ID NO 22
<211> LENGTH: 28
<212> TYPE: DNA
<213> ORGANISM: Artificial Sequence
<220> FEATURE:
<223> OTHER INFORMATION: PCR primer

<400> SEQUENCE: 22
actctagaag ttggaaagac ttcactgc                                      28

<210> SEQ ID NO 23
<211> LENGTH: 28
<212> TYPE: DNA
<213> ORGANISM: Artificial Sequence
<220> FEATURE:
<223> OTHER INFORMATION: PCR primer

<400> SEQUENCE: 23
acgaattccg gagagaaatg atacatta                                      28

<210> SEQ ID NO 24
<211> LENGTH: 28
<212> TYPE: DNA
<213> ORGANISM: Artificial Sequence
<220> FEATURE:
<223> OTHER INFORMATION: PCR primer

<400> SEQUENCE: 24
actctagaag ttcttatggg ttacttgg                                      28
```

```
<210> SEQ ID NO 25
<211> LENGTH: 28
<212> TYPE: DNA
<213> ORGANISM: Artificial Sequence
<220> FEATURE:
<223> OTHER INFORMATION: PCR primer

<400> SEQUENCE: 25
acgaattcat cccatatttg tagtggag                                   28

<210> SEQ ID NO 26
<211> LENGTH: 31
<212> TYPE: DNA
<213> ORGANISM: Artificial Sequence
<220> FEATURE:
<223> OTHER INFORMATION: PCR primer

<400> SEQUENCE: 26
acggatccgg agacgtttgg aggtgtatgg g                               31

<210> SEQ ID NO 27
<211> LENGTH: 30
<212> TYPE: DNA
<213> ORGANISM: Artificial Sequence
<220> FEATURE:
<223> OTHER INFORMATION: PCR primer

<400> SEQUENCE: 27
acgcggccgc tagcgttatt gttcaacgcc                                 30

<210> SEQ ID NO 28
<211> LENGTH: 33
<212> TYPE: DNA
<213> ORGANISM: Artificial Sequence
<220> FEATURE:
<223> OTHER INFORMATION: PCR primer

<400> SEQUENCE: 28
acgcggccgc acattacctt caatcatgtc ctc                             33

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
tcactggata taccaccgtt                                            20

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
ccactcatcg cagtactgtt                                            20

<210> SEQ ID NO 31
<211> LENGTH: 22
<212> TYPE: DNA
<213> ORGANISM: Artificial Sequence
<220> FEATURE:
<223> OTHER INFORMATION: PCR primer
```

```
<400> SEQUENCE: 31
atgttaccag atataaatat ag                                          22

<210> SEQ ID NO 32
<211> LENGTH: 22
<212> TYPE: DNA
<213> ORGANISM: Artificial Sequence
<220> FEATURE:
<223> OTHER INFORMATION: PCR primer

<400> SEQUENCE: 32
catttcccct gtattggaaa tg                                          22

<210> SEQ ID NO 33
<211> LENGTH: 23
<212> TYPE: DNA
<213> ORGANISM: Artificial Sequence
<220> FEATURE:
<223> OTHER INFORMATION: PCR primer

<400> SEQUENCE: 33
atgaaacaga aaatgaattt cag                                         23

<210> SEQ ID NO 34
<211> LENGTH: 26
<212> TYPE: DNA
<213> ORGANISM: Artificial Sequence
<220> FEATURE:
<223> OTHER INFORMATION: PCR primer

<400> SEQUENCE: 34
ctaatcatct attataatct caaacg                                      26

<210> SEQ ID NO 35
<211> LENGTH: 23
<212> TYPE: DNA
<213> ORGANISM: Artificial Sequence
<220> FEATURE:
<223> OTHER INFORMATION: PCR primer

<400> SEQUENCE: 35
atgattagag taaaaataca taa                                         23

<210> SEQ ID NO 36
<211> LENGTH: 23
<212> TYPE: DNA
<213> ORGANISM: Artificial Sequence
<220> FEATURE:
<223> OTHER INFORMATION: PCR primer

<400> SEQUENCE: 36
ctatgtattt aatagttgga tta                                         23

<210> SEQ ID NO 37
<211> LENGTH: 25
<212> TYPE: DNA
<213> ORGANISM: Artificial Sequence
<220> FEATURE:
<223> OTHER INFORMATION: PCR primer

<400> SEQUENCE: 37
atgaaattcg ctattgtctt attgt                                       25
```

```
<210> SEQ ID NO 38
<211> LENGTH: 29
<212> TYPE: DNA
<213> ORGANISM: Artificial Sequence
<220> FEATURE:
<223> OTHER INFORMATION: PCR primer

<400> SEQUENCE: 38
tcatatctgt gtaaataaaa aaggttccg                                        29

<210> SEQ ID NO 39
<211> LENGTH: 20
<212> TYPE: DNA
<213> ORGANISM: Artificial Sequence
<220> FEATURE:
<223> OTHER INFORMATION: PCR primer

<400> SEQUENCE: 39
ctcgataaca gagtcaatgc                                                  20

<210> SEQ ID NO 40
<211> LENGTH: 26
<212> TYPE: DNA
<213> ORGANISM: Artificial Sequence
<220> FEATURE:
<223> OTHER INFORMATION: PCR primer

<400> SEQUENCE: 40
ctttgcacta ttatctaaat gaggcg                                           26

<210> SEQ ID NO 41
<211> LENGTH: 27
<212> TYPE: DNA
<213> ORGANISM: Artificial Sequence
<220> FEATURE:
<223> OTHER INFORMATION: PCR primer

<400> SEQUENCE: 41 atctttccctt ttattgcatt aacaggg                                         27
```